(12) United States Patent
Pass et al.

(10) Patent No.: US 8,287,861 B2
(45) Date of Patent: Oct. 16, 2012

(54) ANTI-HUMAN INTERLEUKIN-20 ANTIBODIES

(75) Inventors: Jesper Pass, Allerød (DK); Søren Østergaard, Brønshøj (DK); Jes Thorn Clausen, Høng (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/601,164

(22) PCT Filed: Jun. 30, 2009

(86) PCT No.: PCT/EP2009/058155
§ 371 (c)(1),
(2), (4) Date: Jan. 7, 2010

(87) PCT Pub. No.: WO2010/000721
PCT Pub. Date: Jan. 7, 2010

(65) Prior Publication Data
US 2011/0091475 A1     Apr. 21, 2011

Related U.S. Application Data

(60) Provisional application No. 61/079,005, filed on Jul. 8, 2008.

(30) Foreign Application Priority Data

Jun. 30, 2008 (EP) .................... 08159344

(51) Int. Cl.
*A61K 39/395* (2006.01)
*A61K 39/00* (2006.01)
*C12N 5/07* (2010.01)

(52) U.S. Cl. .................. 424/130.1; 424/133.1; 435/335

(58) Field of Classification Search ........................ None
See application file for complete search history.

(56) References Cited

U.S. PATENT DOCUMENTS

| 7,119,191 | B2 | 10/2006 | Conklin et al. |
| 7,151,166 | B2 | 12/2006 | Conklin et al. |
| 7,393,684 | B2 | 7/2008 | Xu et al. |
| 7,435,800 | B2 * | 10/2008 | Chang ............... 530/388.23 |
| 2004/0191243 | A1 | 9/2004 | Chen et al. |
| 2006/0134756 | A1 * | 6/2006 | Xu et al. ............. 435/70.21 |
| 2006/0142550 | A1 | 6/2006 | Chang |
| 2006/0188476 | A1 | 8/2006 | Olsen et al. |
| 2007/0116700 | A1 | 5/2007 | Liu et al. |
| 2008/0247945 | A1 | 10/2008 | Xu et al. |

FOREIGN PATENT DOCUMENTS

| WO | 92/07584 | 5/1992 |
| WO | 99/27103 A1 | 6/1999 |
| WO | WO 99/27103 | 6/1999 |
| WO | WO 01/46261 | 6/2001 |
| WO | WO 03/051384 | 6/2003 |
| WO | WO 2004/085475 | 10/2004 |
| WO | WO 2005/052000 | 6/2005 |
| WO | WO 2006/086396 | 8/2006 |
| WO | WO 2007/081465 | 7/2007 |
| WO | 2008/009645 | 1/2008 |
| WO | 2008/045563 | 4/2008 |
| WO | 2008/086395 A2 | 7/2008 |
| WO | WO 2008/157161 | 12/2008 |
| WO | 2009/077483 | 6/2009 |
| WO | 2009/103113 A1 | 8/2009 |
| WO | 2010/000721 | 1/2010 |
| WO | 2010/072691 | 7/2010 |
| WO | 2011/104381 A2 | 9/2011 |
| WO | 2011/147921 A1 | 12/2011 |

OTHER PUBLICATIONS

Klimka et al., Human anti-CD30 recombinant antibodies by guided phage antibody selection using cell panning, British Journal of Cancer 83: 252-260, 2000.*

Beiboer et al., Guided Selection of a Pan Carcinoma Specific Antibody Reveals Similar Binding Characteristics yet Structural Divergence Between the Original Murine Antibody and its Human Equivalent, J. Mol. Biol. 296:833-849, 2000.*

Staelens et al., Humanization by variable domain resurfacing and grafting on a human IgG4, using a new approach for determination of non-human like surface accessible framework residues based on homology modeling of variable domains. Molec. Immunol. 43, 1243-1257, 2006.*

Lonberg et al., Human monoclonal antibodies from transgenic mice—pp. 69-97, in Therapeutic Antibodies. Handbook of Experimental Pharmacology, Y. Chernajovsky, A. Nissim (eds.), Springer-Verlag, Berlin-Heidelberg, 2008, ISBN 978-3-540-73258-7.*

Chang, C. et al., "Crystal Structure of Interleukin-19 Defines a New Subfamily of Helical Cytokines", The Journal of Biological Chemistry, 2003, vol. 278, No. 5, pp. 3308-3313.

Dumont, F. J., "IL-10-Related Cellular Cytokines and Their Receptors: New Targets for Inflammation and Cancer Therapy", Expert Opinion on Therapeutic Patents, 2004, vol. 14 No. 3, pp. 281-299.

Dumoutier, L. et al., "Cutting Edge: STAT Activation by IL-19, IL-20 and mda-7 Through IL-20 Receptor Complexes of Two Types", Journal of Immunology, 2001, vol. 167, pp. 3545-3549.

Hsu, Y. et al., "Function of Interleukin-20 as a Proinflammatory Molecule in Rheumatoid and Experimental Arthritis", Arthritis and Rheumatism, 2006, vol. 54, No. 9, pp. 2722-2733.

Hunt, D. W. C. et al., "Ultraviolet B Light Stimulates Interleukin-20 Expression by Human Epithelial Keratinocytes", Photochemistry and Photobiology, 2006, vol. 82, pp. 1292-1300.

Kragstrup, T. W. et al., "The Expression of IL-20 and IL-24 and Their Shared Receptors are Increased in Rheumatoid Arthritis and Spondyloarthropathy", Cytokine, 2008, vol. 41, pp. 16-23.

(Continued)

*Primary Examiner* — Elly-Gerald Stoica
(74) *Attorney, Agent, or Firm* — Michael J. Brignati

(57) ABSTRACT

Anti-human IL20 monoclonal antibodies that can reduce IL20 mediated activation of both IL20R1/IL20R2 and IL22R1/IL20R2 receptor complexes in one or more species, including humans, are described, as well as antigen-binding molecules such as, e.g., antigen-binding antibody fragments, antibody derivatives, and multi-specific molecules designed or derived from such antibodies, and methods or producing such antibodies or other antigen-binding molecules. Such antibodies or other antigen-binding molecules can be used for treating various diseases and disorders, including autoimmune or inflammatory diseases or disorders.

10 Claims, 24 Drawing Sheets

OTHER PUBLICATIONS

Li, H. et al., "Interleukin-20 Induced Cell Death in Renal Epithelial Cells and was Associated with Acute Renal Failure", Genes and Immunity, 2008, vol. 9, pp. 395-404.

Otkjaer, K. et al., "The Dynamics of Gene Expression of Interleukin-19 and Interleukin-20 and Their Receptors in Psoriasis", British Journal of Dermatology, 2005, vol. 153, pp. 911-918.

Parrish-Novak, J. et al., "Overlapping Ligand Specificities but Divergent Function in the IL-20 Subfamily", Journal of Interferon and Cytokine Research, 2002, vol. 22, Supplement 46.

Parrish-Novak, J. et al., "Interleukins 19, 20 and 24 Signal Through Two Distinct Receptor Complexes", The Journal of Biological Chemistry, 2002, vol. 277, No. 49, pp. 47517-47523.

Rich, B. E., "IL-20: A New Target for the Treatment of Inflammatory Skin Disease", Expert Opinion on Therapeutic Patents, 2003, vol. 7, No. 2, pp. 165-174.

Rømer, J. et al., "Epidermal Overexpression of Interleukin-19 and -20 mRNA in Psoriatic Skin Disappears After Short-Term Treatment with Cyclosporine A or Calcipotriol", The Journal of Investigative Dermatology, 2003, vol. 121, No. 6, pp. 1306-1311.

Stenderup, K. et al., "Interleukin 20 Controls Psoriasis Induction and Maintenance", 2006, vol. 154, pp. 11-35.

Stenderup, K. et al., "Interleukin-20 Plays a Critical Role in Maintenance and Development of Psoriasis in the Human Xenograft Transplantation Model", British Journal of Dermatology, 2009, vol. 160, pp. 284-296.

Wang, F. et al., "Prominent Production of IL-20 by CD68+/CD11c+ Myeloid-Derived Cells in Psoriasis: Gene Regulation and Cellular Effects", Journal of Investigative Dermatology, 2006, vol. 126, pp. 1590-1599.

Wei, C. et al., "Detection of IL-20 and its Receptors on Psoriatic Skin", Clinical Immunology, 2005, vol. 117, pp. 65-72.

Zheng, Y. et al., "Role of Cytokine therapy in the Treatment of Psoriasis", Drug Discovery Today, 2007, vol. 4, No. 1, pp. 25-31.

Wuyts et al., 1999,"Isolation of the CXC chemokines ENA-78 GROa and GROg from tumor cells and leukocytes reveals NH2—terminal heterogeneity. Functional comparison of different natural isoforms" Euro. J. Biochem., vol. 260, pp. 421-429.

Rohovsky et al., 1997, "Growth factors and angiogenesis in wound healing", Growth Factors Wound Healing, Eds: Ziegler T.R., Pierce G.F., Herndon D.N.; Springer New York N.Y., pp. 8-26.

Slavin, 1997, "Cytokines and tissue repair", Journal Immunol. Immunopharmacol, vol. 17, No. 1, pp. 25-29.

George et al. 1988, "Macromolecular Sequencing & Synthesis", pp. 127-149, Ch. 12 Alan R. Liss, Inc.

Harlow et al., 1988. "Antibodies A Laboratory Manual", p. 76, Ch. 5, Cold Springs Harbor Laboratory.

Cunningham et al. "High Resolution Epitope Mapping of hGH-Receptor Interactions by Alanine—Scanning Mutagenesis", Science, vol. 244, pp. 1081-1085, 1989.

Mikayama et al., "Molecular cloning and functional expression of a cDNA encoding glycosylation-inhibiting factor", Proc. Natl. Acad. Sci. USA, vol. 90, pp. 10056-10060, 1993 EGS.

Blumberg et al., "Interleukin 20: Discovery, Receptor Identification, and Role in Epidermal Function", Cell, 104, pp. 9-19, 2001.

D'Andrea et al., "Interleukin 10 (IL-10) Inhibits Human Lymphocyte Interferon y-Production by Surppressing Natuarl Killer Cell Stimulatory Factor/IL-12 Synthesis in Accessory Cells" Journal Exp. Med., 1993, vol. 178, pp. 1041-1048.

EST From Incyte Pharmaceuticals Inc., INC819592, 1996 1 page.

European Application No. 05020542: International Search Report dated Jun. 12, 2005, 6 pages.

Incyte Pharmaceuticals Inc., INC4304592, Jul. 8, 1998, 1 page.

Salinas et al., 2010, "Understanding and modulating opalescence and viscosity in a monoclonal antibody formulation", Journal of Pharmaceutical Sciences, vol. 99, No. 1, pp. 82-93.

International Search Report for PCT/EP2011/058648, dated Aug. 25, 2011.

International Search Report for PCT/EP2011/052914, dated Sep. 28, 2011.

* cited by examiner

Mature hIL20 (SEQ ID NO:1)

LKTLNLGSCVIATNLQEIRNGFSEIRGSVQAKDGNIDIRI
LRRTESLQDTKPANRCCLLRHLLRLYLDRVFKNYQTP
$\underline{D}_{78}$ $\underline{H}_{79}$ $Y_{80}$ $T_{81}$ $L_{82}$ $\underline{R}_{83}$ $K_{84}$ $I_{85}$ $\underline{S}_{86}$ $S_{87}$ $L_{88}$ $A_{89}$ $\underline{N}_{90}$ $S_{91}$ $\underline{F}_{92}$ $\underline{L}_{93}$
$T_{94}$ $I_{95}$ $K_{96}$ $K_{97}$ $D_{98}$ $L_{99}$ $R_{100}$ $L_{101}$ $C_{102}$ $H_{103}$
AHMTCHCGEEAMKKYSQILSHFEKLEPQAA
VVKALGELDILLQWMEETE

Figure 1A

```
hIL19  MKLQCVSLWLLGTILILCSVDNHGLRR-----CLISTDMHHIEESFQEIK
hIL20  MKASSLAFSLLSAAFYLLWTPSTGLKTLNLGSCVIATNLQEIRNGFSEIR
cIL20  MKASSLAFSLLSAAFYLLWTPSTGLKTLNLGSCVIATNLQEIRNGFSEIR
mIL20  MKGPGLAFGLFSAVGFLLWTPLTGLKTLHLGSCVITANLQAIQKEFSEIR
       **   ::: *:.:    *  .  **.      *:*:::: * : *.**.

hIL19  RAIQAMDTFPNVTILSTLETLQIIKPLDVCCVTKNLLAFYVDRVFKDHQE
hIL20  GSVQAKDGNIDIRILRRTESLQDTKPANRCCLLRHLLRLYLDRVFKNYQT
cIL20  GSVQAKDGNIDIRILRRTESLQDTKPADQCCLLRHLLRLYLDRVFKNYQT
mIL20  DSVQAEDTNIDIRILRPTESLKDIKSLDRCCFLRHLVRFYLDRVFKVYQT
       ::**:*   :: **   *:*:  *. ( **. .:*: :*;***** :* hIL19  PNFKILRKISSIANSFLYMQKTLRQCQEQRQCHCRQEATNATRVIHDNYD
hIL20  PDHYTLRKISSLANSFLTIKKDLRLCHAHMTCHCGEEAMKKYSQILSHFE
cIL20  LDHYTLRKISSLANSFLTIKKDLRLCHAHMTCHCGEEAMKKYGQILSHFE
mIL20  PDHHTLRKISSLANSFLIIKKDLSVCHSHMACSCGEEAMEKYNQILSHFI
       :  *******:***** ::* * *: ;  *** (**  :    * .::

hIL19  QLEVHAAAIKSLGELDVFLAWINKNHEVMFSA    (SEQ ID NO: 3)
hIL20  KLEPQAAVVKALGELDILLQWMEETE------   (SEQ ID NO: 2)
cIL20  ELEPQAAVVKALGELDILLQWMEETE------   (SEQ ID NO: 4)
mIL20  ELELQAAVVKALGELGILLRWMEEML------   (SEQ ID NO: 5)
```

Figure 1B

```
15D2 VH
             1         2          3          4         5          6
    12345678901234567890123456789012345AB6789012ABC34567890
    QVQLVQSGAEVKKPGASVKVSCKASGYTFTNDIIH  WVRQAPGQRLEWMGWINA  GYGNTQYS
    QVQLVQSGAEVKKPGASVKVSCKASGYTFTSYAMH  WVRQAPGQRLEWMGWINA  GNGNTKYS
                                 ****                *                *

7          8          9          10        11
    12345678901234567890123ABC4567890123456789OABCDEFGHIJK1234567890   <- Kabat
    QNFQDRVSITRDTSASTAYMELISLRSEDTAVYYCAREPLMFGESSPHDYYGM  DVWGQGTTVTVSS  15D2 VH
    QKFQGRVTITRDTSASTAYMELSSLRSEDTAVYYCAR/    LMFGELS  /YYGM  DVWGQGTTVTVSS  VH1_03/D3-10/JH6
      *                           *
```

Figure 3A

```
SB7 VH
           1          2          3            4          5            6
  1234567890123456789012345678901234567f12345AB67890123456789012ABC34567890
  QVQLVQSGAEVKRPGASVKVSCKASGYTFTSSHIMH   WVRQAPGQRLEWMGWINA    GYGNTKYS
  QVQLVQSGAEVKKPGASVKVSCKASGYTFTSYAMH    WVRQAPGQRLEWMGWINA    GNGNTKYS
               *                  ***                          *

7          8            9           10           11
  12345678901234567890123ABC456789012345678890ABCDEFGHIJK1234567890   <- Kabat
  QNFQGRVTITRDTSASTAYMELISLRSEDTAVYYCAREPLWFGELSPHDYYGM   DVWGQGTTVTVSS  SB7 VH
  QRFQGRVTTITRDTSASTAYMELSSLRSEDTAVYYCAR/  LWFGELS  /YYGM  DVWGQGTTVTVSS  VH1_03/D3-10/JH6
   *            *            *
```

```
          1         2          3                4          5         6
 123456789012345678901234567ABCDEF8901234567890123456789012345678901234567890
AIQLTQSPSSLSASVGDRVTITCRASQ      GISSALAWYQQKPGKAPKLLIYDASSLESGVPS
AIQLTQSPSSLSASVGDRVTITCRASQ      GISSALAWYQQKPGKAPKLLIYDASSLESGVPS 7         8         9        10
 12345678901234567890123456789012345AB67890123456789   <- The Kabat Scheme
RFSGSGSGTDFTLTISSLQPEDFATYYCQQFNSYP  LTFGGGTKVEIKR        15D2/5B7 VL
RFSGSGSGTDFTLTISSLQPEDFATYYCQQFNSYP  LTFGGGTKVEIKR        VKI_L18/JK4
```

Figure 3C

1SD2/5B7 VH alignment

```
              1         2          3            4          5            6
     1234567890123456789012345AB67890123456789012ABC34567890
     QVQLVQSGAEVKRPGASVKVSCKASGYTFSSHIMH    WVRQAPGQRLEWMGWINA    GYGNTKYS
     QVQLVQSGAEVKRPGASVKVSCKASGYTFTNDIH     WVRQAPGQRLEWMGWINA    GYGNTQYS
     QVQLVQSGAEVKRPGASVKVSCKASGYTFXXXIXH    WVRQAPGQRLEWMGWINA    GYGNTXYS
                          ***                                        *

7         8            9              10           11
     12345678901234567890123ABC45678901234567890ABCDEFGHIJKL1234567890  <- Kabat
     QMFQDRVTITRDTSASTAYMELISLRSEDTAVYYCAREPLWFGELSPHDYYGM DWGQGTTVTVSS  5B7 VH
     QMFQDRVSITRDTSASTAYMELISLRSEDTAVYYCAREPLWFGESSPHDYYGM DWGQGTTVTVSS  1SD2 VH
     QMFQDRVXITRDTSASTAYMELISLRSEDTAVYYCAREPLWFGEXSPHDYYGM DWGQGTTVTVSS  consensus
           *                                        *
```

Figure 3D

```
                    1                   2                    3                    4                    5                    6
         1234567890123456789012345678901234567ABCDEF890123456789012345678901234567890
2F6      VTMWTQSPSLLSASTGDRVTISCRMSQ              GISSYLAWYQQKPGKAPELLIYAASTLQSGVPS
C3       EIVLTQSPATLSLSPGERATLSCRASQ              SVSSYLAWYQQKPGQAPRLLIYDASNRATGIPA
F56_type1 AIQLTQSPSSLSASVGDRVTITCRASQ             GISSALAWYQQKPGKAPKLLIYDASSLESGVPS
F56_type2 EIVLTQSPGTLSLSPGERATLSCRASQS            VSSYLAWYQQKPGQAPRLLIYGASSRATGIPD
15D2/5B7 AIQLTQSPSSLSASVGDRVTITCRASQ              GISSALAWYQQKPGKAPKLLIYDASSLESGVPS 7                    8                    9                    10
         12345678901234567890123456789012345AB67890123456789
2F6      RFSGSGSGTDFTLTISCLQSEDFATYYC QQYSFP  LITFGQGTKVEIKRT
C3       RFSGSGSGTDFTLTISSLEPEDFAVYYC QQRSNWPP YTFGQGTKLEIKRT
F56_type1 RFSGSGSGTDFTLTISSLQPEDFATYYC QQFNSYP  LITFGQGTKVEIKRT
F56_type2 RFSGSGSGTDFTLTISRLEPEDFAVYYC QQYGSSP           FGQGTKVEIKRT
15D2/5B7 RFSGSGSGTDFTLTISSLQPEDFATYYC QQFNSYP  LITFGQGTKVEIKRT
```

ANTI-HUMAN INTERLEUKIN-20 ANTIBODIES

CROSS-REFERENCE TO RELATED APPLICATIONS

This application is a 35 U.S.C. §371 national stage application of International Patent Application PCT/EP2009/058155, filed Jun. 30, 2009, which claimed priority of European Patent Application 08159344.4, filed Jun. 30, 2008; this application further claims priority under 35 U.S.C. §119 of U.S. Provisional Application 61/079,005, filed Jul. 8, 2008.

FIELD OF THE INVENTION

The present invention relates to antibodies against human interleukin-20 (IL20), including human monoclonal anti-IL20 antibodies, as well as methods of production, compositions, and use thereof.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Nov. 20, 2009. The Sequence Listing is made up of 43 bytes, and the information contained in the attached "SEQUENCE LISTING" is identical to the information in the specification as originally filed. No new matter is added.

BACKGROUND OF THE INVENTION

Interleukin-19 (IL19), IL20, and interleukin-24 (IL24) are members of the interleukin-10 (IL10) cytokine family. All three interleukins bind and signal through the IL20R1/IL20R2 heterodimeric receptor. IL20 and IL24 (but not IL19) are also ligands for the receptor complex composed of IL20R2 and IL22R1 (Parrish-Novak et al., J Biol Chem 2002; 277: 47517-47523; Dumoutier et al., J Immunol 2001; 167: 3545-3549). It has been proposed that IL19 and IL20, along with other IL10 family members, form a distinct subfamily of helical cytokines where at least IL19 and IL20 have similar three-dimensional structures (Chang et al., J Biol Chem 2003; 278: 3308-13).

IL20 and its receptors are present in elevated levels in psoriatic lesions (Wei et al., Clin Immunol (2005) 117: 65-72; Rømer et al., J Invest Dermatol 2003; 121, 1306-1311; Wang et al., J Invest Dermatol 2006; 126: 1590-1599; Otkjæmr et al., Br J Dermatol 2005; 153: 911-918) and in synovial fluid of rheumatoid arthritis patients (Hsu et al., Arthritis Rheum 2006; 54: 2722-2733; Kragstrup et al., Cytokine 2008; 41: 16-2). Antagonizing IL20 activity using receptor fragments or monoclonal antibodies has therefore been described as a promising approach for treatment of various inflammatory conditions (e.g., WO9927103, WO0146261, WO2003051384, WO2004085475, and WO2006086396). For example, polyclonal anti-IL20 antibodies were found to be therapeutically effective in a xenograft model of psoriasis (Stenderup et al., Br J Dermatol 2006; 154: 11-35, Abstract P-12; Stenderup et al. Br J Dermatol 2009; 160(2):284-96).

Antigenic epitopes of human IL20 (hIL20), as well as rat or murine monoclonal antibodies binding huIL20, have also been described (e.g., WO2005052000, US20060142550, and WO2007081465). However, no antibodies suitable for patient treatment have so far been provided. The present invention addresses these and other needs in the art.

SUMMARY OF THE INVENTION

The present invention provides anti-hIL20 monoclonal antibodies that can reduce IL20-mediated activation of IL20R1/IL20R2 and IL22R1/IL20R2 receptor complexes in one or more species, including humans. Typically, the antibodies are fully human or humanized to minimize the risk for immune responses against the antibodies when administered to a patient. The invention also provides anti-hIL20 antibodies having improved solubility properties, making them capable of being formulated at high concentrations. As described herein, other antigen-binding molecules such as, e.g., antigen-binding antibody fragments, antibody derivatives, and multi-specific molecules, can be designed or derived from such antibodies.

Antibodies binding a specific segment of the hIL20 molecule that corresponds to Helix E in IL19 are also provided. In one embodiment, the epitope of the antibody comprise one or more amino acid residues in the segment corresponding to D78-L93, optionally excluding D78, in mature hIL20 (SEQ ID NO:1), e.g., H79, R83, S85, N90, F92, L93, or any combination thereof.

Certain anti-hIL20 antibodies of the invention may also compete with and/or bind to the same epitope or have the same binding interface on hIL20 as one or more of the specific human anti-hIL20 antibodies described herein, including 15D2 and 5B7. For example, in one embodiment, the antibodies of the invention are more capable of competing with 15D2 and/or 5B7 than with known anti-hIL20 antibodies.

In another aspect, antibodies of the invention comprise antigen-binding sequences that derive from one or more of the same human V, D, or J segments as 15D2 or 5B7. The antibodies may, for example, comprise one or more antigen-binding sequences that are identical or substantially identical to 15D2 and/or 5B7 antigen-binding sequences described herein.

In other aspects, the invention provides for nucleic acids encoding antibodies of the invention, expression vectors comprising such nucleic acids, host cells comprising such nucleic acids, host cells producing antibodies of the invention, and methods of producing anti-hIL20 antibodies by culturing such host cells under appropriate conditions. Also provided for are antibody-binding fragments of such antibodies, and molecules comprising such antibodies or antigen-binding fragments, including engineered antibody fragments, antibody derivatives, bispecific antibodies and other multi-specific molecules. Pharmaceutical compositions and kits or other articles that comprise such antibodies or molecules can also be prepared. Further provided for are methods of reducing or inhibiting IL20-mediated activation of IL20R1/IL20R2 and IL22R1/IL20R2 receptor complexes, and methods of treating or preventing autoimmune or inflammatory diseases or disorders, including, but not limited to rheumatoid arthritis, juvenile rheumatoid arthritis, psoriasis, psoriatic arthritis, ankylosing spondylitis, Sjögren's syndrome, multiple sclerosis, inflammatory bowel disease, systemic lupus erythematosus, lupus nephritis, or a combination thereof, using such antibodies.

DESCRIPTION OF THE DRAWINGS

FIG. 1 shows the amino acid sequence of mature hIL20 (A) (SEQ ID NO:1) and (B) an alignment of the precursor form of hIL20 (SEQ ID NO:2), human IL19 (SEQ ID NO:3), murine IL20 (SEQ ID NO:4), and cynomolgus IL20 (SEQ ID NO:5). In (A), the numbered residues correspond to Helix E in IL19, with bold residues representing the key epitope segment of 15D2 and 5B7. Bold underlined residues are the ones most important for 15D2 and 5B7 binding, while bold double-underlined residues were found to be critical for 15D2 and/or 5B7 binding. In (B), the underlined segment in hIL20 is the signal sequence, and other markings are the same as in (A).

FIG. 3 shows analyses of 15D2 heavy-chain variable (VH) region (SEQ ID NO:6) (A), 5B7 VH region (SEQ ID NO:7) (B), and 15D2/5B7 light-chain variable (VL) region (SEQ ID NO:9) (C), and an alignment of the 15D2 and 5B7 VH regions along with a consensus sequence (SEQ ID NO:8) (D). Each antibody sequence is aligned with the corresponding germline sequences, showing the corresponding Kabat-numbering of each amino acid position. In each sequence, the corresponding complementarity-determining region (CDR) sequences according to the Kabat scheme are shown in bold, underlined text. VH1_03, D3-10, and JH6 correspond to sequences comprising SEQ ID NOS:10, 12 and 14, respectively, and VKI_L18/JK4 correspond to sequences comprising SEQ ID NOS:15 and 17, respectively. The coding sequences of D3-10, JH6, and JK4 are provided in SEQ ID NOS: 11, 13, and 16, respectively.

FIG. 13 shows the primary sequence of hIL20 used in an amide hydrogen/deuterium exchange (HX)—mass spectrometry (MS) study to determine the 15D2 binding interface. The primary hIL20 sequence (using mature Met-1 numbering, thus differing+1 from the corresponding residue in SEQ ID NO:1) is displayed above the HX analyzed peptides (shown as horizontal bars). Peptides showing similar exchange patterns both in the presence and absence of 15D2 are indicated by grey bars whereas peptides showing reduced deuterium incorporation upon 15D2 binding are indicated by black bars.

DEFINITIONS

Figure 2:
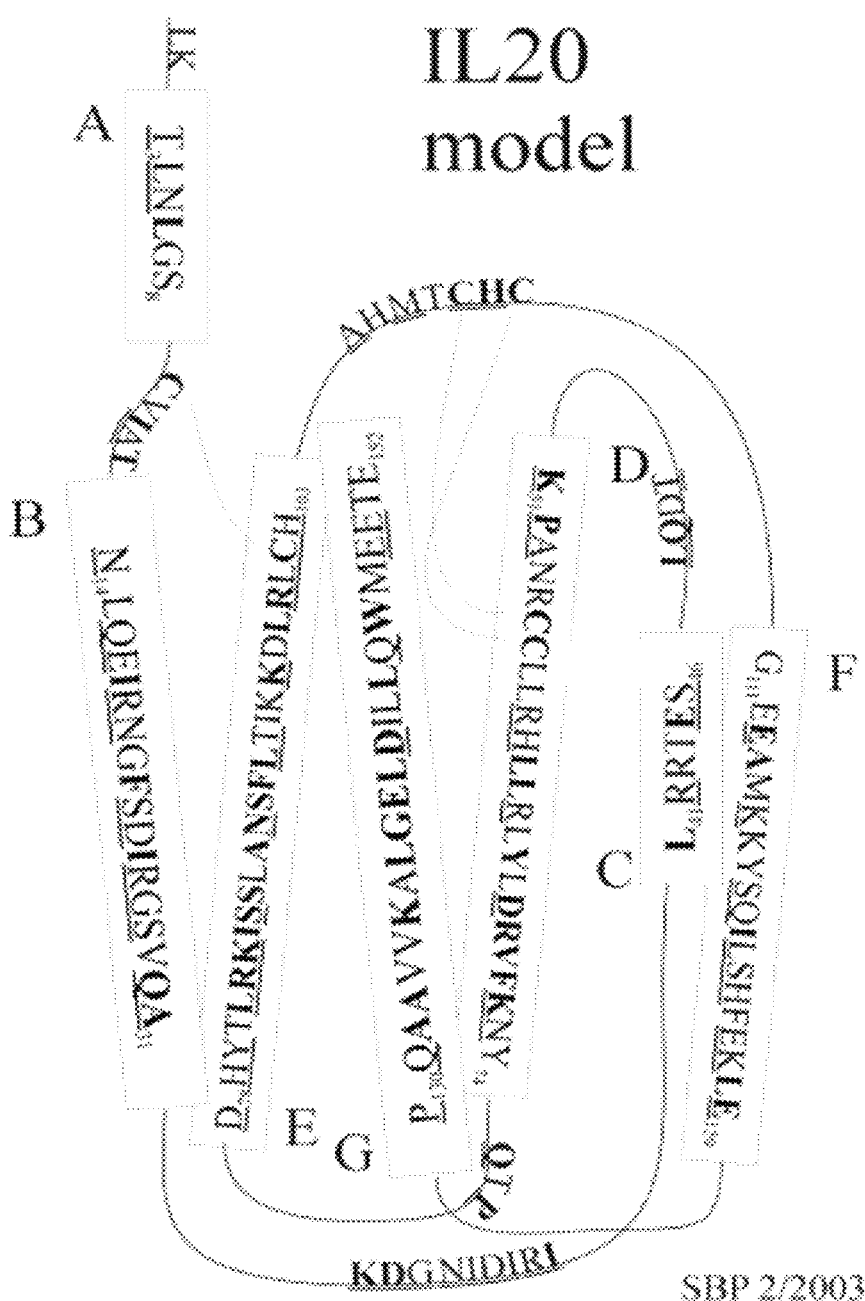
FIG. 2 shows a model of hIL20 (using IL19 nomenclature), built using the Chemical Computing Group's Molecular Operating Environment (MOE) software from the template 1N1F.pdb of hIL19. Using a hIL19/hIL20 sequence alignment and the helix assignments in 1N1F.pdb, the figure was generated using Corel Draw (Corel Corporation).

Unless otherwise stated or contradicted by context, the terms "IL20" or "IL-20" refer to human interleukin-20 (hIL20), also known as Zcyto10, including its unprocessed precursor (UniProt Q9NYY1; SEQ ID NO:2), mature form (SEQ ID NO:1, UniProt Q9NYY1 without the residues 1-24 signal sequence), and/or naturally occurring variants or orthologs thereof, such as, e.g., murine IL20 (mIL20) precursor (UniProt Q9JKV9; SEQ ID NO:4), or cynomolgous IL20 (cIL20) precursor (SEQ ID NO:5), or mature forms thereof which lack the signal sequence corresponding to residues 1-24 in precursor hIL20 (SEQ ID NO:2).

The term "antibody" herein is used in the broadest sense and specifically includes full-length monoclonal antibodies, polyclonal antibodies, and, unless otherwise stated or contradicted by context, antigen-binding fragments, antibody variants, and multispecific molecules thereof, so long as they exhibit the desired specificity and/or biological activity. Generally, a full-length antibody is a glycoprotein comprising at least two heavy (H) chains and two light (L) chains interconnected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarily determining regions (abbreviated herein as CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. Various techniques relevant to the production of antibodies are provided in, e.g., Harlow and Lane, ANTIBODIES: A LABORATORY MANUAL, Cold Spring Harbor Laboratory Press, Cold Spring Harbor, N.Y., (1988).

An "antigen-binding fragment" of an antibody is a molecule that comprises a portion of a full-length antibody which is capable of detectably binding to the antigen. Antigen-binding fragments include multivalent molecules comprising one, two, three, or more antigen-binding portions of an antibody, and single-chain constructs wherein the VL and VH regions, or selected portions thereof, are joined by synthetic linkers or by recombinant methods to form a functional, antigen-binding molecule.

The terms "antibody derivative" and immunoconjugate" are used interchangeably herein to denote molecules comprising a full-length antibody or an antigen-binding fragment thereof, wherein one or more amino acids are chemically modified, e.g., by alkylation, PEGylation, acylation, ester formation or amide formation or the like, e.g., for linking the antibody to a second molecule. Exemplary modifications include PEGylation, cysteine-PEGylation, biotinylation, radiolabelling, and conjugation with a second agent, such as a cytotoxic agent.

A "multispecific molecule" comprises an antibody, or an antigen-binding fragment thereof, which is associated with or linked to at least one other functional molecule (e.g. another peptide or protein such as another antibody or ligand for a receptor) to generate a molecule that binds to at least two different binding sites or target molecules. Exemplary multispecific molecules include bi-specific antibodies and antibodies linked to soluble receptor fragments or ligands.

The term "human antibody", as used herein, is intended to include antibodies having variable regions in which both the framework and CDR regions are derived from human germline immunoglobulin sequences. Furthermore, if the antibody contains a constant region, the constant region also is derived from human immunoglobulin sequences. Collections of human germline sequences are available at, e.g., the NCBI website. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and function. In some instances, FR residues of the human immunoglobulin are replaced by corresponding non-human residues ("back-mutations"). Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992), WO 92/02190, US Patent Application 20060073137, and U.S. Pat. Nos. 6,750,325, 6,632,927, 6,639,055, 6,548,640, 6,407,213, 6,180,370, 6,054,297, 5,929,212, 5,895,205, 5,886,152, 5,877,293, 5,869,619, 5,821,337, 5,821,123, 5,770,196, 5,777,085, 5,766,886, 5,714,350, 5,693,762, 5,693,761, 5,530,101, 5,585,089, and 5,225,539.

The term "hypervariable region" when used herein refers to the amino acid residues of an antibody that are responsible for antigen binding. The hypervariable region generally comprises amino acid residues from a "complementarity-determining region" or "CDR" (residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol. 1987; 196:901-917) and/or the specificity-determining residues (SDRs), which are the residues that are most crucial in the antibody-antigen interaction (Kashmiri et al., Methods 2005; 36:25-34). The SDRs can be determined using, e.g., 3D structural analysis of the antibody-antigen interaction or by mutational analysis using known techniques. Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence (see FIGS. 3 and 4).

A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence, but differs from the parent polypeptide in at least one respect.

The term "epitope" or "antigenic determinant" of an antibody is the part of a predetermined antigen to which the antibody binds, and usually consists of chemically active surface groupings of amino acids or sugar chains. The specific amino acids defining a protein epitope can be relatively few in number, and typically comprise the amino acids that are directly involved in binding to the antibody, though other amino acids that are not directly involved in binding to the antibody can nevertheless be blocked when the antibody binds. The amino acids in a protein epitope may be close to each other or widely dispersed along the length of antigen, being brought into the correct epitope conformation via folding. A "conformational epitope" refers to an epitope that depends on the predetermined antigen being correctly folded, while a "linear epitope" can also be recognized by the antibody when not correctly folded, e.g., in denatured form or in the form of a fragment comprising the epitope.

"Specific binding" as used herein refers to the ability of an antibody to bind a predetermined antigen, such as, e.g., IL20. Typically, the antibody binds with a dissociation constant (Kd) of $10^{-8}$ or less, and binds to the predetermined antigen with a Kd that is at least 2-fold less than its Kd for binding to a non-specific antigen (e.g., BSA) other than the predetermined antigen or a closely related molecule (e.g., an ortholog).

The term "substantially identical" in the context of two amino acid sequences means that the sequences, when optimally aligned, such as by the programs GAP or BEST-FIT using default gap weights, share at least about 50, at least about 60, at least about 70, at least about 80, at least about 90, at least about 95, at least about 98, or at least about 99 percent sequence identity.

"Corresponding" amino acid positions in two substantially identical amino acid sequences are those aligned by any of the protein analysis software referred to herein, typically using default parameters.

A nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

Unless otherwise expressly indicated or clearly contradicted by context, the term "or" herein is used in the inclusive sense of "and/or."

"Activation" of a receptor or receptor complex means an increased or decreased activity of any or all intracellular signal transduction elements associated with the receptor or receptor complex after binding of the ligand to the receptor or receptor complex under normal physiological or pathophysiological conditions, as compared to a control. In the case of the IL20R1/IL20R2 and IL22R1/IL20R2 receptor complexes, receptor activation can be analyzed using, e.g., a luciferase assay similar to the one described in Example 9. "Reducing activation" of a receptor or receptor complex means that the activation of the receptor is reduced by at least about 10%, preferably at least about 20%, more preferably at least about 30%, most preferably at least about 50%, or more, in comparison to a control (e.g., the level of activation in the absence of antibody).

Some assays for evaluating the antibodies or other antigen-binding molecules described herein employ one or more "controls." A "control" may be a standard value retrieved from a text book; a value obtained by running the same assay in the absence of ligand (e.g., IL20), receptor (e.g., IL20R1/IL20R2 and/or IL22R1/IL20R2), or antibody; or in the presence of a non-specific molecule (e.g., a non-specific antibody); or some other reference value used in the art. In the case of a receptor activation assay testing, for example, the ability of an antibody to reduce activation of a receptor complex, a suitable control value can be obtained by running the assay in the absence of the antibody or in the presence of an antibody not specifically binding to the ligand, receptor complex, or other components involved in receptor activation.

DESCRIPTION OF THE INVENTION

The present invention provides for human anti-IL20 antibodies suitable for pharmaceutical formulations, diagnostic uses, and therapeutic uses. As described in the Examples, a novel epitope was identified for two human anti-IL20 antibodies designated 15D2 and 5B7. Key epitope residues were mapped to a region of hIL20 that corresponds to Helix E in hIL19 (Chang et al., J Biol Chem 2003; 278: 3308-13). A predicted model of hIL20 using the hIL19 nomenclature is shown in FIG. 1, with Helix E corresponding to residues D78 to H103 in the mature hIL20 sequence (SEQ ID NO:1). It was found that an antibody binding to the novel hIL20 epitope reduced hIL20-mediated activation of both the IL20R1/IL20R2 and IL22R1/IL20R2 receptors, and reduced IL20-mediated, but not IL19- or IL24-mediated, receptor activation in a proliferation assay. The epitope was further found to exist in both native and denatured form of the hIL20 antigen, as well as in both murine and cynomolgous IL20. Both 15D2 and 5B7 were also soluble at concentrations of at least about 80 mg/ml, and were found to derive from the same set of human germline genes (Example 3 and FIG. 3).

The invention thus provides antibodies which combine one or more functional properties, one or more structural properties, and/or antibodies which combine one or more functional with one or more structural properties described in subsequent sections and the Examples.

In one aspect, the present invention provides an antibody, such as a monoclonal human or humanized antibody, or an antigen-binding fragment thereof, that specifically binds to hIL20, optionally also to one or more hIL20 orthologs, specifically reduces hIL20 mediated activation of both hIL20R1/hIL20R2 and hIL22R1/hIL20R2 receptor complexes and/or their orthologs, and/or has a high solubility. In one embodiment, the heavy or light chain variable region sequences of the antibody derive from one or more of the 15D2 and 5B7 germline and/or V, D, or J segments. In one embodiment, the CDR and/or variable sequences of antibodies of the invention are substantially identical to one or more antigen-binding sequence of 15D2 and/or 5B7. In one embodiment, the antibody interacts with one or more residues in the segment H79 to H103 in the hIL20 sequence (SEQ ID NO:1), and may, for example, bind to H79, R83, S85, N90, F91, L92, or a combination thereof. The antibody may be in any form suitable for therapeutic applications, e.g., a full-length antibody or a fragment thereof.

In one aspect, the invention provides for an isolated anti-hIL20 antibody, or an antigen-binding fragment thereof, comprising a heavy chain variable region that is derived from a set of human genes comprising VH1_03, D3-10, and JH6 genes. In one embodiment, the heavy chain variable region comprises the CDR2 and CDR3 sequences, and, optionally, the CDR1 sequence, of SEQ ID NO:8, respectively corresponding to Kabat residues 50-65, 95-102, and 31-35. In one embodiment, the light chain variable region comprises a sequence derived from a set of human genes comprising VKI_L18 and JK4 genes. In a specific embodiment, the light chain variable region comprises the sequence of SEQ ID NO:9 and the heavy-chain variable region comprises the sequence of SEQ ID NO:6 or SEQ ID NO:7. In another specific embodiment, the antibody is of the IgG4 isotype.

In one aspect, the invention provides for a human antibody, or an antigen-binding fragment thererof, which binds to hIL20 and has one or more functional properties selected from (a) reducing IL20-mediated activation of IL20R1/IL20R2 and IL22R1/IL20R2 receptor complexes; (b) reducing IL20-mediated proliferation of BaF-3 cells recombinantly expressing IL20R1/IL20R2; (c) not reducing IL19- or IL24-mediated proliferation of BaF-3 cells recombinantly expressing IL20R1/IL20R2; (d) binding to hIL20 with a KD of about 1 nM or less; and (e) has a solubility of at least about 80 mg/ml in an aqueous buffered solution at about pH 7.4, optionally comprising 150 mM NaCl. In one embodiment, the antibody has properties (a) to (d). In one embodiment, the antibody has all of properties (a) to (e). In one embodiment, the antibody or antigen-binding fragment competes in binding to hIL20 with an antibody comprising a light-chain variable region comprising SEQ ID NO:9 and a heavy-chain variable region comprising SEQ ID NO:6 or SEQ ID NO:7. In one embodiment, the antibody or antigen-binding fragment binds to an epitope comprising at least one residue selected from H79-H103 of mature hIL20 (SEQ ID NO:1). In one embodiment, the epitope comprises at least one residue selected from H79-L93. In one embodiment, the antibody or antigen-binding fragment comprises a heavy chain variable region comprising CDR1, CDR2, and CDR3 sequences comprising Kabat residues residues 31-35, 50-65, and 95-102, respectively, of SEQ ID NO:6 or SEQ ID NO:7. In one embodiment, the antibody further comprises a light chain variable region comprising CDR1, CDR2, and CDR3 sequences comprising Kabat residues 24-34, 50-56 and 89-97, respectively, of SEQ ID NO:9. In one embodiment, the antibody heavy and light chain variable sequences are substantially identical to the respective heavy and light chain variable sequences of 15D2 and/or 5B7, e.g., having a sequence identity of at least about 80%, at least about 90%, or at least about 95%. In a specific embodiment, the antibody is of the IgG4 isotype.

In one aspect, the invention provides such human anti-hIL20 antibodies that are sufficiently soluble for use in pharmaceutical compositions. In one embodiment, the invention provides a pharmaceutical composition comprising an effective amount, e.g., at a concentration of at least about 80 mg/ml or at least about 100 mg/ml, of an antibody of the invention, and a pharmaceutically acceptable excipient, diluent, or carrier. In one embodiment, the antibody is of an IgG4 isotype and comprises a heavy chain variable region that is derived from a set of human genes comprising VH1_03, D3-10, and JH6 genes and/or the light chain variable region comprising a sequence derived from a set of human genes comprising VKI_L18 and JK4 genes. In one specific embodiment, the light chain variable region comprises the sequence of SEQ ID NO:9 and the heavy-chain variable region comprises the sequence of SEQ ID NO:6. In one specific embodiment, the light chain variable region comprises the sequence of SEQ ID NO:9 and the heavy-chain variable region comprises the sequence of SEQ ID NO:7.

In one aspect, the invention provides for an antibody, antigen-binding fragment, or pharmaceutical composition of the invention for use as a medicament.

In one aspect, the invention provides for an antibody, antigen-binding fragment, or pharmaceutical composition of the invention for use in treating an inflammatory or autoimmune disorder.

In one aspect, the invention provides for the use of an antibody, antigen-binding fragment, or pharmaceutical composition of the invention in the preparation of a medicament for treating an inflammatory or autoimmune disorder.

In one aspect, the invention provides for a method of treating a subject suffering from or at risk for an inflammatory or autoimmune disorder by administering an antibody, antigen-binding fragment, or pharmaceutical composition of the invention.

Inflammatory or autoimmune disorders suitable for such uses include rheumatoid arthritis, juvenile rheumatoid arthritis, psoriasis, psoriatic arthritis, ankylosing spondylitis, Sjögren's syndrome, multiple sclerosis, inflammatory bowel disease, systemic lupus erythematosus, or lupus nephritis, or a combination of any thereof, as well as co-morbidities associated with these diseases, with cardiovascular disease being a non-limiting example of said co-morbidities.

In one aspect, the invention provides for a method of recombinantly producing an anti-IL20 antibody or antigen-binding fragment, comprising culturing a host cell producing the antibody or antigen-binding fragment of the invention under suitable conditions, and recovering the antibody or antigen-binding fragment. The host cell typically comprises an expression vector comprising nucleic adic(s) encoding heavy and/or light chain sequences of antibodies or antigen-binding fragments of the invention.

The production, characterization, and use of antibodies, antigen-binding fragments, or other molecules specifically binding hIL20 and having some or all of these properties are described in more detail in the following sections.

Anti-IL20 Antibodies

The antibodies of the invention are characterized by particular functional and/or structural features or properties of the antibodies. Assays to evaluate the functional activities of anti-IL20 antibodies are described in detail in separate sections and in the Examples, and structural properties such as, e.g., amino acid sequences, are described below.

Functional Properties

The antibodies of the invention bind specifically to hIL20. The antibody preferably binds to hIL20 with high affinity, for example with a KD of $10^{-7}$ M or less, a KD of $10^{-8}$ M or less, a KD of 1 nM or less, a KD of about 0.3 nM or less, or a KD of about 0.2 nM or less, or a KD of about 0.1 nM or less. A recombinantly produced anti-IL20 antibody in sodium acetate buffer may, for example, bind to recombinant hIL20 with an affinity of about 0.1 nM or less, optionally with an affinity of about 0.01-0.05 nM, in a Biacore assay (see, e.g., Example 12). Additionally, the antibodies may detectably bind to IL20 from one or more non-human mammals, including mouse (e.g, *mus musculus*) and/or cynomolgus monkey (*Macaca fascicularis*) (see, e.g., Example 2). Furthermore, the antibodies of the invention are capable of reducing IL20-mediated activation of IL20R1/IL20R2 and IL22R1/IL20R2 receptor complexes in vitro and/or in vivo. This may be tested in one or more assays described herein (see, e.g., Examples 1, 2, and 9-11) or known in the art. Using a suitable assay, an antibody of the invention can reduce hIL20-mediated activation of human IL20R1/IL20R2 and IL22R1/IL20R2 receptor complexes by at least about 10%, more preferably by at least 20%, even more preferably by at least 30%, at least 40%, at least 50%, or at least 60%, as compared to a control (e.g., in the absence of any anti-hIL20 antibody). The antibody may further be able to reduce IL20-mediated activation of IL20R1/IL20R2 and IL22R1/IL20R2 receptor complexes in other species, such as mice and cynomolgous monkeys, using the corresponding ligand and receptor complex orthologues (see Example 9).

The antibodies of the invention reduce IL20-mediated proliferation of BaF-3 cells recombinantly expressing IL20R1/IL20R2 and IL22R1/IL20R2, but typically have no significant effect on IL19- and/or IL24-induced proliferation (see, e.g., Example 2). In such assays, an antibody of the invention typically reduces proliferation with an EC50 of about 50 µM or less, about 5 µM or less, about 1 µM or less, about 0.5 µM or less, about 0.1 µM or less, about 0.05 µM or less, or about 0.02 µM or less. For example, in a proliferation assay described in Example 10, recombinantly produced human antibody 15D2 had an EC50 of less than 0.02 µM.

The anti-IL20 antibodies of the invention can inhibit hIL20-mediated receptor complex activation by any mechanism, or by a combination of different mechanisms. Typically, an anti-hIL20 antibody can reduce or prevent hIL20 binding to cell-associated hIL20 receptors or fully formed receptor complexes. Additionally or alternatively, antibodies of the invention may bind to cell-associated hIL20 single-chain receptor molecules, but prevent formation of the receptor complex. Additionally or alternatively, antibodies of the invention may bind to cell-associated hIL20 single-chain receptor molecules and fully formed receptor complexes, but reduce or inhibit structural changes necessary for receptor complex activation. Which one or more mechanisms are involved can be identified by, e.g., testing whether the antibody associates to cells expressing human IL20R1, IL20R2, IL22R1 receptor molecules, or IL20R1/IL20R2 and/or IL22R1/IL20R2 receptor complexes in the presence of hIL20. In a specific embodiment, the antibody reduces the binding of hIL20 to hIL20R2. In another specific embodiment, the antibody does not reduce binding of hIL20 to at least one of the human IL20R1/IL20R2 and IL22R1/IL20R2 receptor complexes. Particular antibodies of the invention bind a hIL20 epitope that at least partially overlaps, or includes at least one residue in, the segment corresponding to Helix E in IL19, optionally excluding D78. Without being limited to theory, this segment can comprise or be part of a helical structure in IL20 that is involved in binding to and/or activating IL20R1/IL20R2 and IL22R1/IL20R2. For a model of hIL20 built using a hIL20-hIL19 sequence alignment and structural IL19 information, see FIG. 2. In the hIL20 sequence, this segment comprises residues D78-H103 of mature hIL20 (SEQ ID NO:1). In one embodiment, the antibody or antigen-binding fragment of the invention thus binds to an epitope comprising at least one residue selected from D78-H103 of mature hIL20 (SEQ ID NO:1). In other specific and separate embodiments, the epitope includes 2, 3, 4, 5, 6, 7 or more residues in the D78-H103 segment.

In another aspect, the invention provides an antibody binding an epitope comprising 1, 2, 3, 4, 5, 6, 7 or more residues in the segment corresponding to residues D78-K96 or H79-K96 in mature hIL20. This segment contains an epitope providing a higher affinity of anti-IL20 antibody 5B7. The antibody may alternatively bind an epitope comprising 1, 2, 3, 4, 5, 6, 7 or more residues in the segment corresponding to residues D78-L93 or H79-L93, which contains the key residues of the 15D2 epitope. For example, the antibody may bind an epitope comprising at least one residue selected from H79-L93. The antibody may alternatively bind an epitope comprising 1, 2, 3, 4, 5, 6, 7 or more residues in the segment corresponding to residues H79-N90, which contains the key residues of the 5B7 epitope. In specific and separate embodiments, all key residues of the epitope is in a segment corresponding to residues D78-H103, D78-K96, D78-L93, or D78-N90, optionally excluding D78.

In another aspect, the antibody binds an epitope comprising at least one of residues H79, R83, S85, N90, F91, and L92 of mature IL20. In separate and specific embodiments, the antibody binds 2, 3, 4, 5, 6, or all of D78, H79, R83, S85, N90, F91, and L92. In another embodiment, the epitope comprises at least residues H79 and N90. In an additional embodiment, the epitope further comprises residue R83. In yet another embodiment, the epitope further comprises 1, 2, 3, or all of D78, S85, F91, and L92. In another aspect, the invention provides antibodies that compete with and/or bind to the same epitope on hIL20 as an antibody comprising the VH and VL sequences of either of 5B7 or 15D2, described below. Such antibodies thus compete in binding to hIL20 with an antibody comprising a light-chain variable region comprising SEQ ID NO:9 and a heavy-chain variable region comprising SEQ ID NO:6 or SEQ ID NO:7. Such antibodies can be identified based on their ability to compete with 15D2 and/or 5B7 in standard hIL20 binding assays as described herein (see, e.g., Example 4 or the section entitled "Binding Assays" below). The ability of a test antibody to reduce or inhibit the binding of 15D2 and/or 5B7 to hIL20 demonstrates that the test antibody can compete with 15D2 and/or 5B7 for binding to hIL20 and thus can bind to the same hIL20 segment or epitope as 5B7 and/or 15D2. In a preferred embodiment, the antibody that binds to the same segment or epitope of hIL20 as 5B7 and/or 15D2 is a human monoclonal antibody. Such human monoclonal antibodies can be prepared and isolated according to known methods in the art, as described herein.

In a particular embodiment, the antibody binds to a different hIL20 segment or epitope than those bound by any of the rat antibodies described in WO2005052000 (262.4.1.2.2.1, 262.5.1.6.4.4, and 262.7.1.3.2.4), and/or by murine antibodies (7E) described in US20060142550 and WO2007081465, and competes more with 15D2 and/or 5B7 in binding to hIL20 than with either of the listed mouse or rat antibodies. In another particular embodiment, the antibody is a human antibody which does not bind to the segment correspondding to residues 42-102 of the IL20 precursor (SEQ ID NO:2).

Any combination of the above-described functional features, other functional features described in the Examples, and/or structural features describing in the following section, may be exhibited by an antibody of the invention.

Structural Properties

In one aspect, the invention provides human anti-IL20 antibodies with suitable stability and/or solubility characteristics for being formulated in aqueous formulations at concentrations of at least about 50 mg/ml, at least about 60 mg/ml, at least about 70 mg/ml, at least about 80 mg/ml, at least about 90 mg/ml, or at least about 100 mg/ml, which aqueous formulation may further comprise a pharmaceutically acceptable excipient, diluent, or carrier, and typically has a pH near neutral or physiological pH. In one embodiment, the anti-IL20 antibody has a solubility of at least 80 mg/ml in an aqueous formulation, optionally comprising a 20 mM sodium phosphate buffer and 150 mM NaCl, and having a pH of about 7.4. In one embodiment, the anti-IL20 antibody has a solubility of at least 100 mg/ml in an aqueous formulation, optionally comprising a 20 mM sodium phosphate buffer and 150 mM NaCl, and having a pH of about 7.4. It has now been found that human anti-IL20 antibodies deriving from certain germline sequences are more soluble than others, thereby achieving higher concentrations in an aqueous solution (see, e.g., Example 3). Such embodiments are described in further detail below.

Preferred antibodies of the invention include the human monoclonal antibodies 15D2 or 5B7 characterized as described herein. Heavy and light chain variable domains and CDR sequences of these antibodies are provided below and in FIG. 3, The heavy chain variable domain of 15D2 (SEQ ID NO:6) contains the following CDRs, corresponding to Kabat residues 31-35 (CDR1), 50-65 (CDR2) and 95-102 (CDR3) of SEQ ID NO:6, respectively:

```
VH CDR1: NDIIH

VH CDR2: WINAGYGNTQYSQNFQD

VH CDR3: EPLWFGESSPHDYYGMDV
```

The heavy chain variable domain of 5B7 (SEQ ID NO:7) contains the following CDRs, corresponding to Kabat residues 31-35 (CDR1), 50-65 (CDR2) and 95-102 (CDR3) of SEQ ID NO:7, respectively:

```
VH CDR1: SHIMH

VH CDR2: WINAGYGNTKYSQNFQD

VH CDR3: EPLWFGELSPHDYYGMDV
```

The light chain variable domains of 15D2 and 5B7 (SEQ ID NO:9) contains the following CDRs, corresponding to Kabat residues 24-34 (CDR1), 50-56 (CDR2) and 89-97 (CDR3) of SEQ ID NO:9, respectively:

```
VL CDR1: RASQGISSALA

VL CDR2: DASSLES

VL CDR3: QQFNSYPLT
```

Given that 15D2 and 5B7 both bind IL20, the VH CDR sequences can be "mixed and matched" to create other anti-hIL20 binding molecules of the invention. The hIL20-binding of such "mixed and matched" antibodies can be tested using the binding assays described herein (e.g. flow cytometry, Biacore, ELISAs) and/or using a receptor-activation assay as described herein. The invention thus provides antibodies that comprise the heavy chain and light chain CDR1s, CDR2s and/or CDR3s of 15D2 or 5B7, or combinations thereof. The CDR regions are delineated using the Kabat system (FIG. 3). Given that each of these antibodies can bind to hIL20 with substantially overlapping epitopes, and that antigen-binding specificity is provided primarily by the CDR1, 2 and 3 regions, the VH CDR1, 2 and 3 sequences can be "mixed and matched" (i.e., VH CDRs from different antibodies can be mixed and matched, although each antibody can contain a VH CDR1, 2 and 3 and a VL CDR1, 2 and 3) to create other anti-hIL20 binding molecules of the invention. The 15D2 and 5B7 VH CDRs share substantial structural similarity and are therefore amenable to mixing and matching.

Accordingly, in one aspect, the invention provides an isolated monoclonal antibody comprising: (a) a VH CDR1 from 5B7 or 15D2, (b) a VH CDR2 from 5B7 or 15D2, and (c) a VH CDR3 from 5B7 or 15D2, optionally combined with a VL sequence comprising the VL CDRs of SEQ ID NO:9. This can also be illustrated using consensus VH CDRs, per below.

The consensus variable heavy domain of 5B7/15D2 contains the following CDRs, corresponding to Kabat residues 31-35 (CDR1), 50-65 (CDR2) and 95-102 (CDR3) of SEQ ID NO:8, respectively, with X representing any amino acid, preferably those listed below or conservative substitutions thereof):

```
VH CDR1: X₂X₃IX₄H
(X₂: N or S; X₃: D or H; X₄: I or M,
or conservative substitutions of any thereof)

VH CDR2: WINAGYGNTX₅YSQNFQD
(X₅ is K, Q,
or a conservative substitution of any thereof)

VH CDR3: EPLWFGEX₇SPHDYYGMDV
(X₇ is S, L,
or a conservative substitution of any thereof),
wherein X₂-X₅ and X₇ correspond to residues 31,
32, 34, 59, and 106 in SEQ ID NO: 8,
respectively.
```

Accordingly, in another aspect, the invention provides an antibody comprising the heavy-chain variable regions CDR2 and CDR3, optionally combined with the CDR1, of SEQ ID NO:8. In one embodiment, the antibody comprises the sequence of SEQ ID NO:8. In one aspect, the antibody comprises the heavy-chain variable region CDR2 and CDR3, optionally combined with the CDR1, of SEQ ID NO:6. In one embodiment, the antibody comprises the sequence of SEQ ID NO:6. In one aspect, the antibody comprises the heavy-chain variable region CDR2 and CDR3, optionally combined with the CDR1, of SEQ ID NO:7. In one embodiment, the antibody comprises the sequence of SEQ ID NO:7. In any of these aspects or embodiments, the antibody may optionally further comprise the light-chain variable regions CDR1, CDR2 and CDR3, or the full sequence, of SEQ ID NO:9.

In certain embodiments, an antibody of the invention comprises a VH region from a particular germline H chain immunoglobulin gene, or a combination of particular germline H chain immunoglobulin genes; and/or a VL region from a particular germline L chain immunoglobulin gene, or a combination of particular germline L chain immunoglobulin genes.

For example, in one embodiment, the invention provides an isolated anti-hIL20 antibody comprising a heavy chain variable region that is derived from a set of human genes comprising VH1_03, D3-10, and JH6 genes. The heavy chain variable region may, for example, comprise the CDR2 and CDR3 sequences, and optionally the CDR1 sequence, of SEQ ID NO:8, respectively corresponding to Kabat residues 50-65, 95-102, and 31-35. In another embodiment, the antibody further comprises a light chain variable region that is derived from a set of human genes comprising VKI_L18 and JK4 genes. The light-chain variable region may, for example, comprise the CDR1-CDR3 sequences of SEQ ID NO:9.

In one embodiment, the invention provides an isolated anti-hIL20 monoclonal antibody, or an antigen-binding fragment thereof, wherein the antibody: (a) comprises a VH domain derived from a human VH1_03 gene recombined with a human D3-10 gene and a JH6 gene, (b) comprises a VL domain derived from a human VKI_L18 gene recombined with a human JK4 gene, and (c) the antibody specifically binds to hIL20. For example, the antibody may comprise the light chain variable sequence of SEQ ID NO:9 and the heavy-chain variable sequence of SEQ ID NO:6 or SEQ ID NO:7. As used herein, a human antibody comprises heavy or light chain variable regions "of" or "derived from" or "the product of" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "of" or "derived from" or "the product of" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "of" or "derived from" or "the product of" a particular human germline immunoglobulin sequence may contain amino acid differences as compared to the germline sequence, due to, for example, naturally-occurring somatic mutations or intentional introduction of site-directed mutation.

However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody variable sequence may be at least 95%, or even at least 96%, 97%, 98%, or 99% identical in amino acid sequence to the amino acid sequence encoded by the recombined germline immunoglobulin gene.

Typically, a human antibody derived from a particular human germline sequence will display no more than 10 amino acid differences from the amino acid sequence encoded by the human germline immunoglobulin gene. In certain cases, the human antibody may display no more than 8, no more than 5, or even no more than 4, 3, 2, or 1 amino acid difference, or no amino acid difference, from the amino acid sequence encoded by the recombined germline immunoglobulin gene.

In yet another aspect, an antibody of the invention comprises heavy and light chain variable regions comprising amino acid sequences that are homologous or identical to the amino acid sequences of the preferred 15D2 and 5B7 antibodies described herein, and wherein the antibodies retain the desired functional properties of the anti-hIL20 antibodies of the invention. For example, the invention provides an isolated monoclonal antibody comprising a heavy chain variable domain and a light chain variable domain, wherein: (a) the VH domain comprises an amino acid sequence that is at least 80% identical to an amino acid sequence selected from the group consisting of SEQ ID NOs: 6, 7, and 8; (b) the VL region comprises an amino acid sequence that is at least 80% identical to SEQ ID NO:9; and (c) the antibody specifically binds to hIL20 and exhibits at least one of the functional properties described herein, preferably several of the functional properties described herein.

In other embodiments, the VH and/or VL amino acid sequences may be 85%, 90%, 95%, 96%, 97%, 98%, 99% or 100% identical to the sequences set forth above. An antibody having VH and VL regions having high (i.e., 80% or greater) identity to the VH and VL regions of the sequences set forth above, can be obtained by mutagenesis (e.g., site-directed or PCR-mediated mutagenesis) of nucleic acid molecules encoding SEQ ID NOs:6-9, followed by testing of the encoded altered antibody for retained function (e.g., hIL20 binding affinity or reduction of hIL20-mediated activation of its receptor complexes) using the functional assays described herein.

The percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm in sequence analysis software. Protein analysis software matches similar sequences using measures of similarity assigned to various substitutions, deletions and other modifications, including conservative amino acid substitutions.

The percent identity between two amino acid sequences can be determined, e.g., using the Needleman and Wunsch (J. Mol. Biol. 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Polypeptide sequences can also be compared using FASTA, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183: 63-98; Pearson, Methods Mol. Biol. 2000; 132:185-219).

The sequence identity between two amino acid sequences can also be determined using the algorithm of E. Meyers and W. Miller (Comput. Appl. Biosci., 1988; 11-17) which has been incorporated into the ALIGN program (version 2.0), using a PAM120 weight residue table, a gap length penalty of 12 and a gap penalty of 4.

Another algorithm for comparing a sequence to another sequence contained in a database is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. The protein sequences of the present invention can there be used as a "query sequence" to perform a search against public databases to, for example, identify related sequences. Such searches can be performed using the XBLAST program (version 2.0) of Altschul, et al. 1990 (supra). BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 (supra). When utilizing BLAST and Gapped BLAST programs, default parameters of the respective programs (e.g., XBLAST and NBLAST) can be used. See http://www ncbi.nlm.nih.gov.

In certain embodiments, an antibody of the invention comprises a VH region comprising CDR1, CDR2 and CDR3 sequences and a VL region comprising CDR1, CDR2 and CDR3 sequences, wherein one or more of these CDR sequences comprise specified amino acid sequences based on the preferred antibodies described herein; 15D2 and 5B7, or conservative modifications thereof, and wherein the antibodies retain the desired functional properties of the anti-hIL20 antibodies of the invention. Accordingly, the invention provides an isolated monoclonal antibody, or antigen-binding fragment thereof, comprising a heavy chain variable region comprising CDR1, CDR2, and CDR3 sequences and a light chain variable region comprising CDR1, CDR2, and CDR3 sequences, wherein: (a) the VH region CDR3 sequence comprises an amino acid sequence selected from the group consisting of the CDR3 of SEQ ID NOs:6 and 7, and conservative modifications thereof; (b) the VL region CDR3 sequence comprises the amino acid sequence of the CDR3 of SEQ ID NO:9 or conservative modifications thereof; and (c) the antibody specifically binds to hIL20 and exhibits at least one of the functional properties described herein, more preferably several of the functional properties described herein.

In a further embodiment, the VH region CDR2 sequence comprises an amino acid sequence selected from the group consisting of the CDR2 of SEQ ID NOS: 6 or 7, and conservative modifications thereof; and the VL region CDR2 sequence comprises the CDR2 of SEQ ID NO:9 or conservative modifications thereof.

In a further embodiment, the VH region CDR1 sequence comprises an amino acid sequence selected from the group consisting of the CDR1 of SEQ ID NOS: 6 or 7, and conservative modifications thereof; and the VL region CDR1 sequence comprises the CDR1 of SEQ ID NO:9 or conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

"Conservative" amino acid substitutions are typically those in which an amino acid residue is replaced with an amino acid residue having a side chain with similar physicochemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine).

Thus, one or more amino acid residues within the CDR regions of an antibody of the invention can be replaced with other amino acid residues from the same side chain family and the altered antibody can be tested for retained function (i.e., the functions set forth in (c), (d) and (e) above) using the functional assays described herein.

Antigen-Binding Fragments

The anti-hIL20 antibodies of the invention as described herein may be prepared as full-length antibodies or antigen-binding fragments thereof. Full-length antibodies can be of any suitable class including, e.g., IgG and IgM. The specific class and/or isotype of an antibody can be chosen according to the intended therapeutic use. For example, the IgG1, IgG2, IgG3, and IgG4 isotypes have different affinities for Fc-receptors expressed on, e.g., leukocytes, with IgG4 and IgG2 having lower affinities than IgG1 and IgG3.

Examples of antigen-binding fragments include Fab, Fab', F(ab)2, F(ab')2, F(ab)3, Fv (typically the VL and VH domains of a single arm of an antibody), single-chain Fv (scFv; see e.g., Bird et al., Science 1988; 242:423-426; and Huston et al. PNAS 1988; 85:5879-5883), dsFv, Fd (typically the VH and CH1 domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., III et al., Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23:1126-1136; WO2005040219, and published U.S. Patent Applications 20050238646 and 20020161201.

Antibody fragments can be obtained using conventional recombinant or protein engineering techniques, and the fragments can be screened for antigen-binding or other function in the same manner as are intact antibodies.

Various techniques have been developed for the production of antibody fragments. Traditionally, these fragments were derived via proteolytic digestion of full-length antibodies (see, e.g., Morimoto et al., Journal of Biochemical and Biophysical Methods, 24:107-117 (1992); and Brennan et al., Science, 229:81 (1985)). However, these fragments can now be produced directly by recombinant host cells. Alternatively, Fab'-SH fragments can be directly recovered from E. coli and chemically coupled to form F(ab')2 fragments (Carter et al., Bio/Technology, 10:163-167 (1992)). According to another approach, F(ab')2 fragments can be isolated directly from recombinant host cell culture. In other embodiments, the antibody of choice is a single-chain Fv fragment (scFv). See WO 1993/16185; U.S. Pat. No. 5,571,894; and U.S. Pat. No. 5,587,458. The antibody fragment may also be a "linear antibody", e.g., as described in U.S. Pat. No. 5,641,870, for example. Such linear antibody fragments may be monospecific or bispecific.

Multispecific Molecules

In another aspect, the present invention features multispecific molecules comprising an anti-hIL20 antibody, or an antigen-fragment thereof, of the invention. Such multispecific molecules include bispecific molecules comprising at least one first binding specificity for hIL20 and a second binding specificity for a second target epitope.

One type of bispecific molecules are bispecific antibodies. Bispecific antibodies are antibodies that have binding specificities for at least two different epitopes. Methods for making bispecific antibodies are known in the art, and traditional production of full-length bispecific antibodies is usually based on the coexpression of two immunoglobulin heavy-chain-light-chain pairs, where the two chains have different specificities (Millstein et al., Nature, 305: 537-539 (1983)). Bispecific antibodies can be prepared as full-length antibodies or antibody fragments (e.g. F(ab')2 bispecific antibodies) or any other antigen-binding fragments described herein.

Other multispecific molecules include those produced from the fusion of a hIL20-binding antibody moiety to one or more other non-antibody proteins. Such multispecific proteins and how to construct them have been described in the art. See, e.g., Dreier et al. (Bioconjug. Chem. 9(4): 482-489 (1998)); U.S. Pat. No. 6,046,310; U.S. Patent Publication No. 20030103984; European Patent Application 1 413 316; US Patent Publication No. 20040038339; von Strandmann et al., Blood (2006; 107:1955-1962.), and WO 2004056873.

Multispecific molecules with more than two valencies are also contemplated. For example, trispecific antibodies can be prepared. Tutt et al., J. Immunol, 147: 60 (1991).

The multispecific molecules of the present invention can be prepared by conjugating the constituent binding specificities using methods known in the art. For example, each binding specificity of the multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) J. Exp. Med. 160: 1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulthydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described or reviewed in, for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; U.S. Pat. No. 5,482,858; U.S. Patent application publication 20030078385, Kontermann et al., (2005) Acta Pharmacological Sinica 26(1):1-9; Kostelny et al., (1992) J. Immunol. 148(5):1547-1553; Hollinger et al., (1993) PNAS (USA) 90:6444-6448; and Gruber et al. (1994) J. Immunol. 152: 5368.

Antibody Variants

An antibody of the invention further can be prepared using an antibody having one or more of the VH and/or VL sequences disclosed herein as starting material to engineer a modified antibody or antibody "variant", which modified antibody may have altered properties from the parent antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody. Additionally, from antigen-binding portions of an antibody, other constructs such as antigen-binding fragments, antibody derivatives, immunoconjugates, and multispecific molecules can be prepared.

Standard molecular biology techniques can be used to prepare and express the altered antibody sequence.

Though an antibody variant or derivative typically has at least one altered property as compared to the "parent" antibody, the antibody variant or derivative can retain one, some or most of the functional properties of the anti-hIL20 antibodies described herein, which functional properties include, but are not limited to: (a) reduces hIL20-mediated activation of human IL20R1/IL20R2 and IL22R1/IL20R2 receptor complexes, (b) binds to murine and cynomolgous IL20 orthologs, preferably with substantially similar efficacy or affinity; (c) competes with one or more of 15D2 and 5B7 in binding to hIL20, and (d) binds to an epitope in the segment corresponding to Helix E (FIG. 2). Any combination of the above-described functional features, and/or the functional features as described in the Examples, may be exhibited by an antibody of the invention.

The functional properties of the antibody variants and derivatives can be assessed using standard assays available in the art and/or described herein. For example, the ability of the antibody to bind hIL20 can be determined using standard binding assays, such as those set forth in the Examples (e.g., Biacore, flow cytometry, or ELISAs).

Variable Region Modifications

One type of variable region engineering that can be performed is CDR grafting. Antibodies interact with target antigens predominantly through amino acid residues that are located in the six heavy and light chain complementarily determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. Sci. U.S.A. 86:10029-10033;U.S. Pat. No. 5,225,539 to Winter, and U.S. Pat. Nos. 5,530,101; 5,585,089; 5,693,762 and 6,180,370 to Queen et al.) Accordingly, another embodiment of the invention pertains to an isolated monoclonal antibody, or antigen binding portion thereof, comprising the VH and/or VL CDR sequences of monoclonal antibodies 15D2 or 5B7, but framework sequences different from these antibodies.

Framework sequences can be obtained from public DNA databases or published references that include germline antibody gene sequences. For example, germline DNA sequences for human heavy and light chain variable region genes can be found in the "dBase" human germline sequence database (available on the Internet at www.mrccpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germ-line VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J. Immunol. 24:827-836; the contents of each of which are expressly incorporated herein by reference.

Preferred framework sequences for use in the antibodies of the invention are those that are structurally similar to the framework sequences used by selected antibodies of the invention, e.g., similar to the VH1_03, D3-10, JH6, VKI_L18, and/or JK4 sequences of 15D2 or 5B7. The VH CDR1, 2 and 3 sequences of 15D2 or 5B7 can be grafted onto framework regions that have the same sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

In another aspect of the invention, the structural features of anti-hIL20 antibodies of the invention, e.g., 15D2 and 5B7, are used to create structurally related anti-hIL20 antibodies that retain at least one functional property of the antibodies of the invention, such as binding to hIL20. For example, one or more CDR regions of 5B7 or 15D2, or variants thereof, can be combined recombinantly with known framework regions and/or other CDRs to create additional, recombinantly-engineered, anti-hIL20 antibodies of the invention. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-hIL20 antibody comprising: (a) providing: (i) a heavy chain variable region antibody sequence comprising CDR1, CDR2, and CDR3 sequences from SEQ ID NOS:6 or 7, and (ii) a light chain variable region antibody sequence comprising CDR sequences from SEQ ID NO:9; (b) altering at least one amino acid residue within the first antibody sequence and/or the second antibody sequence to create at least one altered antibody sequence; and (c) preparing the altered antibody sequence; and (d) expressing the altered antibody sequence as a protein.

Another type of variable region modification is to mutate amino acid residues within the VH and/or VL CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions. Moreover, typically no more than 8, more typically no more than 5 residues are altered within a single CDR region.

Accordingly, in another embodiment, the invention provides isolated anti-hIL20 monoclonal antibodies, or antigen-binding fragments thereof, comprising a heavy chain variable region comprising VH CDR1, CDR2, and CDR3 sequences of SEQ ID NO:6 or 7, or amino acid sequences having one, two, three, four, five, six, seven, or eight amino acid substitutions, deletions or additions in one or more of these CDRs; and a light chain variable region comprising VL CDR1, CDR2, and CDR3 sequences from SEQ ID NO:9, or amino acid sequences having one, two, three, four, five, six, seven, or eight amino acid substitutions, deletions or additions in one or more of these CDRs.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, for 15D2 and 5B7, the VH residues that are different from the corresponding germline sequence are indicated by "*" in FIG. 3. To return, e.g., the framework region sequences to their germline configuration, the somatic mutations outside the CDRs can be "backmutated" to the germline sequence by, for example, site-directed mutagenesis or PCR-mediated mutagenesis (e.g., residues 13, 68, and/or 82A of the 15D2 VH domain or residues 13, 30 and/or 82A of the 5B7 VH domain can be "backmutated" from the VH amino acid to the germline amino acid. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Fc Modifications

In addition or as an alternative to modifications made within the framework or CDR regions, antibodies of the invention may be engineered to include modifications within the Fc region, typically to alter one or more functional properties of the antibody, such as serum half-life, complement fixation, Fc receptor binding, protein stability and/or antigen-dependent cellular cytotoxicity, or lack thereof. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The residues in the Fc region are numbered according to Kabat.

If desired, the class of an antibody may be "switched" by known techniques. Such techniques include, e.g., the use of direct recombinant techniques (see e.g., U.S. Pat. No. 4,816,397) and cell-cell fusion techniques (see e.g., U.S. Pat. No. 5,916,771). For example, an antibody that was originally produced as an IgM molecule may be class switched to an IgG antibody. Class switching techniques also may be used to convert one IgG subclass to another, e.g., from IgG1 to IgG2. Thus, the effector function of the antibodies of the invention may be changed by isotype switching to, e.g., an IgG1, IgG2, IgG3, IgG4, IgD, IgA, IgE, or IgM antibody for various therapeutic uses. Exemplary cDNA sequences for constant regions are available via, e.g., GenBank, each of which incorporated by reference in its entirety, are as follows:

Human IgG1 constant heavy chain region: GenBank accession No.: J00228;

Human IgG2 constant heavy chain region: GenBank accession No.: J00230;

Human IgG3 constant heavy chain region: GenBank accession No.: X04646;

Human IgG4 constant heavy chain region: GenBank accession No.: K01316; and

Human kappa light chain constant region: GenBank accession No.: J00241.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al. In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In yet other embodiments, the Fc region is altered by replacing at least one amino acid residue with a different amino acid residue to alter the effecter function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both to Winter et al. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 and 239 are altered to thereby alter the ability of the antibody to fix complement. This approach is described further in PCT Publication WO 94/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. (2001) J. Biol. Chem. 276:6591-6604). Specific mutations at positions 256, 290, 298, 333, 334 and 339 were shown to improve binding to FcRIII. Additionally, the following combination mutants were shown to improve FcγRIII binding: T256A/S298A, S298A/E333A, S298A/K224A and S298A/E333A/K334A.

The constant region may further be modified to stabilize the antibody, e.g., to reduce the risk of a bivalent antibody separating into two monovalent VH-VL fragments. For example, in an IgG4 constant region, the Serine (S, Ser) residue at position 241 according to the Kabat numbering system may be mutated to a proline (P, Pro) residue to allow complete disulphide bridge formation at the hinge (see, e.g., Angal et al., Mol Immunol. 1993; 30:105-8). According to the EU index numbering system, Kabat residue 241, corresponds to residue 228.

Glycosylation Modifications

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP1176195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(I,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 7:176 180).

In certain embodiments of the methods of engineering antibodies of the invention, mutations can be introduced randomly or selectively along all or part of an anti-hIL20 antibody coding sequence (e.g., a 15D2 or 5B7 coding sequence) and the resulting modified antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof.

Alternatively, PCT Publication WO 03/074679 by Lazar et al. describes methods of using computational screening methods to optimize physiochemical properties of antibodies.

Antibody Derivatives

Antibody derivatives (or immunoconjugates) within the scope of this invention include anti-hIL20 antibodies conjugated or covalently bound to a second agent.

For example, in one aspect, the invention provides immunoconjugates comprising an antibody conjugated or covalently bonded to a cytotoxic agent. The term "cytotoxic agent" as used herein is a molecule that is capable of killing a cell to which it becomes associated, e.g., via IL20-binding to cell-surface hIL20 receptors. Any type of moiety with a cytotoxic or cytoinhibitory effect can be conjugated to the present antibodies to form a cytotoxic conjugate of the present invention, including therapeutic radioisotopes, toxic proteins, toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, anthracyclines, epidophyllotoxins, taxanes, antimetabolites, alkylating agents, antibiotics, COX-2 inhibitors, SN-38, antimitotics, antiangiogenic and apoptotoic agents, particularly doxorubicin, methotrexate, taxol, CPT-11, campto thecans, nitrogen mustards, gemcitabine, alkyl sulfonates, nitrosoureas, triazenes, folic acid analogs, pyrimidine analogs, purine analogs, platinum coordination complexes, *Pseudomonas* exotoxin, ricin, abrin, 5-fluorouridine, ribonuclease (RNase), DNase I, Staphylococcal enterotoxin-A, pokeweed antiviral protein, gelonin, diphtherin toxin, *Pseudomonas* exotoxin, and *Pseudomonas* endotoxin and others (see, e.g., Remington's Pharmaceutical Sciences, 19th Ed. (Mack Publishing Co. 1995); Goodman and Gilman's The Pharmacological Basis of Therapeutics (McGraw Hill, 2001); Pastan et al. (1986) Cell 47:641; Goldenberg (1994) Cancer Journal for Clinicians 44:43; U.S. Pat. No. 6,077,499; the entire disclosures of which are herein incorporated by reference). It will be appreciated that a toxin can be of animal, plant, fungal, or microbial origin, or can be created de novo by chemical synthesis.

In another embodiment, the antibody is derivatized with a radioactive isotope, such as a therapeutic radionuclide or a radionuclide suitable for detection purposes. Any of a number of suitable radioactive isotopes can be used, including, but not limited to, 1-131, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Also preferred are radionuclides that substantially decay with generation of alpha-particles.

The antibody conjugates of the invention can be used to modify a given biological response, where the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-I ("IL1"), interleukin-2 ("1 L2"), interleukin-6 ("IL-6"), granulocyte macrophage colony stimulating factor ("GM-CSF"), granulocyte colony stimulating factor ("G-CSF"), or other growth factors.

The second agent can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (see, e.g., Yu et al. (1994) Int. J. Cancer 56: 244; Wong, Chemistry of Protein Conjugation and Cross-linking (CRC Press 1991); Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995), Cattel et al. (1989) Chemistry today 7:51-58, Delprino et al. (1993) J. Pharm. Sci 82:699-704; Arpicco et al. (1997) Bioconjugate Chemistry 8:3; Reisfeld et al. (1989) Antihody, Immunicon. Radiopharm. 2:217, the entire disclosure of each of which is herein incorporated by reference). See, also, e.g. Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al., (eds.), pp. 303-16 (Academic Press 1985), and Thorpe et al., "The Preparation And Cytotoxic Properties Of Antibody-Toxin Conjugates", Immunol. Rev., 62:119-58 (1982).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T.M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

In other embodiments, the second agent is a detectable moiety, which can be any molecule that can be quantitatively or qualitatively observed or measured. Examples of detectable markers useful in the conjugated antibodies of this invention are radioisotopes, fluorescent dyes, or a member of a complementary binding pair, such as a member of any one of: and antigen/antibody (other than an antibody to IL20), lectin/carbohydrate; avidin/biotin; receptor/ligand; or molecularly imprinted polymer/print molecule systems.

The second agent may also or alternatively be a polymer, intended to, e.g., increase the circulating half-life of the antibody or antigen-binding fragment thereof. Exemplary polymers and methods to attach such polymers to peptides are illustrated in, e.g., U.S. Pat. Nos. 4,766,106; 4,179,337; 4,495,285; and 4,609,546. Additional illustrative polymers include polyoxyethylated polyols and polyethylene glycol (PEG) moieties. As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. For example, a full-length antibody or antibody fragment can be conjugated to one or more PEG molecules with a molecular weight of between about 1,000 and about 40,000, such as between about 2000 and about 20,000, e.g., about 3,000-12,000. To pegylate an antibody or fragment thereof, the antibody or fragment typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). In certain embodiments, the antibody to be pegylated is an a glycosylated antibody. Methods for pegylating proteins are known in the art and can be applied to the antibodies of the invention. See for example, WO2004099231, WO2003031464, EP154316 (by Nishimura et al.) and EP401384 (by Ishikawa et al.).

Nucleic Acids

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from trans-genic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acids encoding the antibody can be recovered from the library. Preferred nucleic acids molecules of the invention are those encoding heavy and light chain sequences of 15D2 or 5B7 monoclonal antibodies of the IgG2 or IgG4 isotype, more preferably IgG4.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (I 991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Antibody Production

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

One preferred animal system for preparing hybridomas is the murine system. Immunization protocols and techniques for isolation of immunized splenocytes for fusion are known in the art, as are fusion partners (e.g., murine myeloma cells) and fusion procedures. Chimeric or humanized antibodies of the present invention can also be prepared based on the sequence of a murine monoclonal antibody using established techniques. For example, DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against hIL20 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice." The HuMAb mouse (Medarex, Inc.) contains human immunoglobulin gene miniloci that encode unrearranged human heavy (p and y) and K light chain immunoglobulin sequences, together with targeted mutations that inactivate the endogenous, u and K chain loci (see e.g., Lonberg, et al. (1994) Nature 368: 856-859). Accordingly, the mice exhibit reduced expression of mouse IgM or K, and, in response to immunization, the introduced human heavy and light chain transgenes undergo class switching and somatic mutation to generate high affinity human IgGK monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4: 117-123; Chen, J. et al. (1993) EMBO J. 12: 821-830; Tuaillon et al. (1994) J. Immunol. 152:2912 2920; Taylor, L. et al. (1994) International immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569, 825; 5,625,126; 5,633,425; 5,789,650; 5, 877,397; 5,661, 016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al. In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al. Still further, alternative transgenic animal systems expressing human immunoglobulin genes are available in the art and can be used to raise anti-hIL20 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al. Moreover, alternative transchromosomic animal systems expressing human immunoglobulin genes are available in the art and can be used to raise anti-hIL20 antibodies of the invention. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-hIL20 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al. When human Ig mice are used to raise human antibodies of the invention, such mice can be immunized with a purified or enriched preparation of hIL20 antigen, as described by Lonberg, N. et al. (1994) Nature 368(6474): 856-859; Fishwild, D. et al. (1996) NatureBiotechnology 14: 845-851; and PCT Publication WO 98/24884 and WO 01/14424. Preferably, the mice will be 6-16 weeks of age upon the first infusion. For example, a purified or enriched preparation (5-50 µg) of hIL20 antigen can be used to immunize the human Ig mice intraperitoneally.

The form and amount of antigen administered (e.g., hIL20 polypeptide), as well as administration schedules and the possible use of adjuvants such as, e.g., complete Freund's adjuvant or incomplete Freund's adjuvant, are typically optimized for each antigen-mouse system according to established methods in the art.

The immune response can be monitored over the course of the immunization protocol with plasma samples being obtained by retroorbital bleeds, and the plasma or serum can be screened by ELISA (as described below), and mice with sufficient titers of anti-hIL20 human immunoglobulin can be used for fusions. Mice can be boosted intravenously with antigen 3 days before sacrifice and removal of the spleen. It is expected that 2-3 fusions for each immunization may need to be performed.

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Alternatively, the cells can be fused by electrofusion. Cells are plated at approximately $2 \times 10^5$ in a flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization. To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by spectroscopy. The monoclonal antibodies can be aliquoted and stored at −80°

Antibodies of the invention can also be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g. PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene.

The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g. polyadenylation signals) that control the transcription or translation of the antibody chain genes. Such regulatory sequences are described, for example, in Goeddel (Gene Expression Technology, Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or p-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors of the invention may carry additional sequences, such as sequences that regulate replication of the vector in host cells (e.g. origins of replication) and selectable marker genes. The selectable marker gene facilitates selection of host cells into which the vector has been introduced (see, e.g. U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies of the invention include Chinese Hamster Ovary (CHO cells) (including dhfr-CHO cells, described in Urlaub and Chasin, (1980) Proc. Nail. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibody Characterization

After production or purification, or as part of a screening or selection procedure, the functional characteristics of an anti-hIL20 antibody of the invention can be investigated. Functional properties of interest include, e.g., antibody binding specificity for hIL20, antibody binding to hIL20 orthologs, antibody competition with reference antibodies (such as, e.g., 5B7 and 15D2), the epitope to which the antibody binds, the affinity of the antibody-antigen interaction, antagonistic properties of the antibody, and solubility.

The following are brief descriptions of exemplary assays for antibody characterization. Some are further described in other sections and/or the Examples.

Binding Assays

The present invention provides for antibodies, and antigen-binding fragments, variants, and immunoconjugates thereof, that bind hIL20. Any of a wide variety of assays can be used to assess binding of an antibody to hIL20. Protocols based upon ELISAs, radioimmunoassays, Western blotting, BIA-CORE, and other competition assays, inter alia, are suitable for use and are well known in the art. Further, several binding assays, including competition assays, are described in the Examples.

For example, simple binding assays can be used, in which a test antibody is incubated in the presence of a target protein or epitope (e.g., IL20 or a portion thereof), unbound antibodies are washed off, and the presence of bound antibodies is assessed using, e.g., radiolabels, physical methods such as mass spectrometry, or direct or indirect fluorescent labels detected using, e.g., cytofluorometric analysis (e.g. FACS-can). Such methods are well known to those of skill in the art. Any amount of binding above the amount seen with a control, non-specific antibody indicates that the antibody binds specifically to the target.

In such assays, the ability of the test antibody to bind to the target cell or protein can be compared with the ability of a (negative) control protein, e.g. an antibody raised against a structurally unrelated antigen, or a non-Ig peptide or protein, to bind to the same target. Antibodies or fragments that bind to the target cells or IL20 using any suitable assay with 25%, 50%, 100%, 200%, 1000%, or higher increased affinity relative to the control protein, are said to "specifically bind to" or "specifically interact with" the target, and are preferred for use in the therapeutic methods described below. The ability of a test antibody to affect the binding of a (positive) control antibody against IL20, e.g. 15D2 or 5B7, may also be assessed.

In one aspect, the invention provides for anti-hIL20 antibodies sharing biological characteristics and/or substantial VH and/or VL sequence identity with 15D2 or 5B7. One exemplary biological characteristic is the binding to the 15D2 or 5B7 epitope, or the respective regions in the extracellular domain of hIL20 to which the 15D2 or 5B7 antibodies bind. To screen for antibodies that bind to the 15D2 or 5B7 epitope, a routine cross-blocking assay, such as that described in Antibodies, A Laboratory Manual, Cold Spring Harbor Laboratory, Ed Harlow and David Lane (1988), can be performed.

In an exemplary cross-blocking or competition assay, 15D2 or 5B7 (control) antibody and a test antibody are admixed (or pre-adsorbed) and applied to a sample containing IL20. In certain embodiments, one would pre-mix the control antibodies with varying amounts of the test antibody (e.g., 1:10 or 1:100) for a period of time prior to applying to the IL20-containing sample. In other embodiments, the control and varying amounts of test antibody can simply be admixed during exposure to the antigen/target sample. As long as one can distinguish bound from free antibodies (e.g., by using separation or washing techniques to eliminate unbound antibodies) and the control antibody from test antibody (e.g., by using species- or isotype-specific secondary antibodies, by specifically labeling the control antibody with a detectable label, or by using physical methods such as mass spectrometry to distinguish between different compounds) one will be able to determine if the test antibody reduces the binding of the control antibody to the antigen, indicating that the test antibody recognizes substantially the same epitope as the control. In this assay, the binding of the (labeled) control antibody in the presence of a completely irrelevant antibody is the control high value. The control low value is be obtained by incubating the labeled (positive) control antibody with unlabeled control antibody, where competition would occur and reduce binding of the labeled antibody.

In a test assay, a significant reduction in labeled antibody reactivity in the presence of a test antibody is indicative of a test antibody that competes with, or substantially binds to the same epitope, as the control antibody. Any test antibody or compound that reduces the binding of the labeled control to the antigen/target by at least 50% or more preferably 70%, at any ratio of control:test antibody or compound between about 1:10 and about 1:100 is considered to be an antibody or compound that competes with or binds to substantially the same epitope or determinant as the control. Preferably, such test antibody or compound will reduce the binding of the control to the antigen/target by at least 90%. Nevertheless, any compound or antibody that reduces the binding of a control antibody or compound to any measurable extent can be used in the present invention.

In one embodiment, competition can be assessed by a flow cytometry test. Cells bearing hIL20 are incubated first with a control antibody that is known to specifically bind to hIL20 receptor, and then with the test antibody which may be labelled with, e.g., a fluorochrome or biotin. The test antibody is said to compete with the control if the binding obtained with preincubation with saturating amounts of control antibody is 80%, preferably, 50, 40 or less of the binding (mean of fluorescence) obtained by the antibody without preincubation with the control. Alternatively, a test antibody is said to compete with the control if the binding obtained with a labeled control (by a fluorochrome or biotin) on cells preincubated with saturating amount of antibody to test is 80%, preferably 50%, 40%, or less of the binding obtained without preincubation with the antibody. See Example 4 for an exemplary antibody competition assay.

Functional Assays

The antibodies of the invention are capable of reducing IL20-mediated activation of IL20R1/IL20R2 and IL22R1/IL20R2 receptor complexes in vitro and/or in vivo. Various suitable assays are known in the art.

For example, the Examples describe a luciferase assay that detects receptor complex activation based on the following principles. Briefly, upon IL20 binding and receptor complex formation, the associated JAK kinases are autophosphorylated and can phosphorylate STAT3 protein. Phosphorylated STAT3 can enter the nucleus and bind a specific DNA element of the promoter that has been placed next to a gene encoding luciferase. Luciferase is then expressed, and can transform the substrate luciferin to light, which can then be detected and quantified.

Another type of in vitro assay for testing of IL20R1/IL20R2 and IL22R1/IL20R2 receptor activation is based on proliferation of, e.g., BaF-3 cells transfected with IL20 receptor complexes from humans or other species. Such an assay can test for a neutralizing effect of IL20-induced proliferation of BaF-3 cells transfected with, e.g., hIL20R1/hIL20R2 or hIL22R1/hIL20R2. The BaF-3 cells are IL3 dependent, and proliferate in vitro after the addition of IL3 in their growth medium. If IL3 is not available, the cells will die within a few days, showing signs of apoptosis already after a few hours of IL3 starvation. When the transfected BaF-3 cells are stimulated through their IL20 receptor complex, they will start to divide and do not need IL3. Specific assays for inhibition of proliferation are described in the Examples, Solubility Assays Suitable assays for testing the solubility, i.e., the concentration of antibody that can be achieved in a solution, are described in Example 3 and in Harris, E.L.V. (1989) In Harris, E.L.V. and Angal, S. (eds), *Protein Purification Methods. A Practical Approach*. IRL Press, New York, see, e.g., pp. 131-133.

Pharmaceutical Formulations

In one embodiment, the present invention provides pharmaceutical composition comprising anti-hIL20 antibodies as described herein together with one or more carriers. The human antibodies of the invention, including 15D2 and 5B7, are suitable for pharmaceutical formulations, where a high concentration is often advantageous or necessary, e.g., when used for subcutaneous administration.

The pharmaceutical formulations and administration modes described in WO2006003179, hereby incorporated by reference in their entireties, can also be used for the antibodies and applications of the present invention.

One object of the invention is to provide a pharmaceutical formulation comprising an antibody of the invention which is present in a concentration from 1 mg/ml to 150 mg/ml, from 1 mg/ml to 200 mg/ml, or from 1 mg/ml to 500 mg/ml, typically in an aqueous or freeze-dried formulation (for reconstitution), and wherein said formulation has a pH from 2.0 to 10.0, typically around neutral pH. Preferably, in an aqueous formulation, the antibody is present in soluble form at concentrations of least about 50 mg/ml, at least about 60 mg/ml, at least about 70 mg/ml, at least about 80 mg/ml, at least about 90 mg/ml, or at least about 100 mg/ml. The formulation may further comprise one or more pharmaceutically acceptable excipients, diluents, and/or carriers. These may include, e.g., a buffer system, as well as one or more preservatives, tonicity agents, chelating agents, stabilizers and/or surfactants. Suitable carriers are known in the art and described in, e.g., Remington: *The Science and Practice of Pharmacy*, 19$^{th}$ edition, 1995.

Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym, Humira and similar formulations may be used with the antibodies of this invention. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and sterile water for injection. The pH is adjusted to 6.5. Alternatively, the antibody can be formulated in a solution comprising a phosphate buffer, or histidine, sucrose, and Polysorbate 80.

Diagnostic Applications

The hIL20-antibodies of the invention also have non-therapeutic applications. For example, anti-hIL20 antibodies may also be useful in diagnostic assays for IL20 protein, e.g. detecting its presence in specific tissues, tissue samples (e.g., synovial fluid) or in serum.

For diagnostic applications, the antibody typically will be labelled with a detectable moiety. Numerous labels are available that can be generally grouped into the following categories:

(a) Radioisotopes, such as $^{35}$S, $^{14}$C, $^{125}$I, $^{3}$H, and $^{131}$I. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare-earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al, "Methods for the Preparation of Enzyme-Antibody Conjugates for use in Enzyme Immunoassay," in Methods in Enzymology (Ed., J. Langone & H. Van Vunakis), Academic Press, New York, 73:147-166 (1981).

The antibodies may also be used for in vivo diagnostic assays. Generally, the antibody is labeled with a radionuclide or a non-radioactive indicator detectable by, e.g., nuclear magnetic resonance, or other means known in the art. Preferably, the label is a radiolabel, such as, e.g., $^{125}$I, $^{131}$I, $^{67}$Cu, $^{99m}$Tc, or $^{111}$In. The labelled antibody is administered to a host, preferably via the bloodstream, and the presence and location of the labelled antibody in the host is assayed. This imaging technique is suitably used in the detection, staging, or treatment of the diseases or disorders in question, for example, rheumatoid arthritis, juvenile rheumatoid arthritis, psoriasis, psoriatic arthritis, ankylosing spondylitis, Sjögren's syndrome, multiple sclerosis, inflammatory bowel disease, systemic lupus erythematosus and/or lupus nephritis, by visualisation of IL20 in synovial fluids and -membranes. The radioisotope is conjugated to the protein by any means, including metal-chelating compounds iodogen techniques for iodination.

As a matter of convenience, the antibodies of the present invention can be provided in a kit, i.e., a packaged combination of reagents in predetermined amounts with instructions for performing the diagnostic assay. Where the antibody is labelled with an enzyme, the kit will include substrates and cofactors required by the enzyme (e.g., a substrate precursor that provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents that substantially optimize the sensitivity of the assay. Particularly, the reagents may be provided as dry powders, usually lyophilized, including excipients that on dissolution will provide a reagent solution having the appropriate concentration.

Therapeutic Applications

Methods of treating a patient using a human or humanized anti-hIL20 antibody as described herein are also provided for by the present invention. In one embodiment, the invention provides for the use of a human or humanized antibody as described herein in the preparation of a pharmaceutical composition for administration to a human patient. Typically, the patient suffers from, or is at risk for, an autoimmune or inflammatory disease or disorder.

In one aspect, the conditions or disorders to be treated with the antibodies and other compounds of the invention are rheumatoid arthritis, juvenile rheumatoid arthritis, psoriasis, psoriatic arthritis, ankylosing spondylitis, Sjögren's syndrome, multiple sclerosis, inflammatory bowel diseases such as ulcerative colitis and Crohn's disease, systemic lupus erythematosus, or lupus nephritis, and any combination thereof, as well as co-morbidities associated with these diseases, with cardiovascular disease being a non-limiting example of said co-morbidities. In a further aspect, other exemplary conditions include, but are not limited to, juvenile chronic arthritis, osteoarthritis, other spondyloarthropathies than ankylosing spondylitis, systemic sclerosis (scleroderma), idiopathic inflammatory myopathies (dermatomyositis, polymyositis), vasculitis, systemic vasculitis, temporal arteritis, atherosclerosis, sarcoidosis, myasthenia gravis, autoimmune hemolytic anemia (immune pancytopenia, paroxysmal nocturnal hemoglobinuria), pernicious anemia, autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, Type 2 diabetes, immune-mediated renal disease (glomerulonephritis, tubulointerstitial nephritis, autoimmune oophiritis), pancreatitis, autoimmune orchitis, autoimmune uveitis, anti-phospholipid syndrome, demyelinating diseases of the central and peripheral nervous systems in addition to multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B. C, D, E and other non-hepatotropic viruses), autoimmune chronic active hepatitis, viral hepatitis, primary biliary cirrhosis, granulomatous hepatitis, Wegener's granulomatosis, Behcet's disease, and sclerosing cholangitis, inflammatory bowel diseases such as celiac disease, gluten-sensitive enteropathy, and Whipple's disease, autoimmune or immune-mediated skin diseases including bullous skin diseases, erythema multiforme and contact dermatitis, atopic dermatitis, dermitis herpetiformis, pemphigus vulgaris, vitiligo (leukoderma), allergic diseases such as asthma, allergic rhinitis, atopic dermatitis, food hypersensitivity and urticaria, sepsis, endotoxemia, immunologic diseases of the lung such as eosinophilic pneumonias, idiopathic pulmonary fibrosis and hypersensitivity pneumonitis, chronic obstructive pulmonary disease, and organ or bone marrow transplantation associated diseases including graft rejection and graft-versus-hostdisease.

For example, in one aspect, the anti-IL20 antibody is used in combination with one or more other anti-inflammatory agents, including, but not limited to, analgesic agents, immunosuppressive agents (e.g., B- or T-cell antagonists such as B-cell depletion agents and T cell inhibiting agents; complement inhibiting agents), corticosteroids, and anti-TNFalpha agents or other anti-cytokine or anti-cytokine receptor agents, and anti-angiogenic agents. Specific examples include metothrexate, TSG-6, Rituxan® or other B-cell therapies, anti-IL12 antibodies, CTLA4-Fc fusion proteins, IL1-receptor antagonists, IL1 antibodies, IL15 antibodies, IL18 antibodies, and anti-IL6R antibodies. Further examples of combination therapies are provided below.

When one or more other agents or approaches are used in combination with the present therapy, there is no requirement for the combined results to be additive of the effects observed when each treatment is conducted separately. Although at least additive effects are generally desirable, any decrease in IL20 activity or other beneficial effect above one of the single therapies would be of benefit. Also, there is no particular requirement for the combined treatment to exhibit synergistic effects, although this is certainly possible and advantageous. The IL20-based treatment may precede, or follow, the other treatment by, e.g., intervals ranging from minutes to weeks and months. It also is envisioned that more than one administration of either the anti-IL20 composition or the other agent will be utilized. The agents may be administered interchangeably, on alternate days or weeks; or a cycle of anti-IL20 treatment may be given, followed by a cycle of the other agent therapy. In any event, all that is required is to deliver both agents in a combined amount effective to exert a therapeutically beneficial effect, irrespective of the times for administration.

Rheumatoid Arthritis

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space is infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, intestitial pneumonitis with pulmonary fibrosis, keratoconjunctivitis sicca, and rheumatoid nodules. IL20 has been demonstrated in rheumatoid arthritis synovial fluid (Hsu et al. (2006) Arthritis Rheum. 54, 2722-2733; Kragstrup et al., (2008) Cytokine 41, 16-23), and IL20 receptor expression has been demonstrated in rheumatoid arthritis synovium (Hsu et al., (2006) Arthritis Rheum. 54, 2722-2733; Sakurai et al., (2008) Rheumatology (Oxford) 47, 815-820).

Accordingly, in one aspect, the invention provides a method for treating and/or preventing rheumatoid arthritis (RA). The method comprises delivering an effective amount of an anti-hIL20 antibody to a patient having RA or being identified/diagnosed as being at substantial risk of developing RA, such that RA is treated or prevented. In a further aspect, the antibody that is capable of detectably reducing IL20-mediated activation of IL20R1/IL20R2 and IL22R1/IL20R2 receptor complexes. In one aspect, the method results in a modulation of one or more biomarkers in a manner consistent with the treatment or prevention (as applicable) of RA (e.g., serum IL-6, TNF-α, IL1, VEGF, TIFF R, IL2R, shed CD4, shed CD8, and/or C reactive protein). In vivo models of RA in which the antibodies of the invention can optionally be tested are described in U.S. Pat. No. 6,414,218 and US Patent Publication No. 20030005469 (related principles and models are described in, e.g., Wooley, P. H., Animal Models of Arthritis, eds. J. H. Klippel and P. A. Dieppe, Mosby Publishers (London), 1998; Erning et al., Arthritis Res, 4 Suppl 3:S133-40, 2002; Holmdahl et al., Ageing Res Rev, 1(1): 135-47, 2002; Anthony et al., Clin Exp Rheumatol, 17(2):240-4,1999; Durie et al., Clin Immuno) Immunopath, 73(1):11-8, 1994; and Muller-Ladner et al., Drugs Today (Bare), 35(4-5):379-88, 1999).

In another aspect, the practice of the method results in a detectable reduction of synovial inflammation in the peripheral joints of the patient/host. In one aspect, the method results in preventing radiographic deterioration and improving physical function in the patient or host as exhibited by, e.g., a reduction in radiographic progression in the patient or host, reduction in swollen and tender joints (as determined by acceptable analytical criteria), and/or significantly improved quality of life (e.g., as determined by a reduction in disability scores on the RA Health Assessment Questionnaire). The antibody can be used alone or in combination with one or more other anti-RA agent, such as a non-steroidal anti-inflammatory drug (NSAID), a COX-2 inhibitor, an analgesic, a corticosteroid (e.g., predinisone, hydrocortisone), gold, an immunosuppressant (e.g., methotrexate), a B-cell depletion agent (e.g., R1-tuxan®), a B-cell agonist (e.g., LymphoStat-B®) and an anti-TNFalpha agent (e.g., Embrel®, Humira® and Remicade®), an anti-IL1 receptor antagonist (e.g., Kineret®), an anti-IL15 antibody, or a disease-modifying anti-rheumatic drug (DMARD).

Demyelinating Diseases

Demyelinating diseases of the central and peripheral nervous systems, including Multiple Sclerosis (MS); idiopathic demyelinating polyneuropathy or Guillain-Barre syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. MS is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions.

Thus, in another aspect, the invention provides a method for treating and/or preventing MS. The method comprises delivering an effective amount of an anti-hIL20 antibody to a human patient having MS or being identified/diagnosed as being at substantial risk of developing MS, such that MS is treated or prevented in the patient or host. The antibody can be used alone or in combination with other anti-MS agents such as Tyzabri®.

Inflammatory Bowel Disease

In another aspect, the invention provides a method for treating and/or preventing inflammatory bowel disease (IBD), such as Crohn's disease or ulcerative colitis.

The method of treating an inflammatory bowel disease comprises delivering an effective amount of an anti-IL20 antibody to a human patient having IBD or being identified/diagnosed as being at substantial risk of developing IBD, such that IBD is treated or prevented in the patient. The antibody can be used alone or in combination with other anti-IBD agents, such as drugs containing mesalamine (including sulfasalazine and other agents containing 5-aminosalicylic acid (5-ASA), such as olsalazine and balsalazide), non-steroidal anti-inflammatory drugs (NSAIDs), analgesics, corticosteroids (e.g., predinisone, hydrocortisone), TNF-inhibitors (including adilimumab (Humira®, etanercept (Enbrel® and infliximab (Remicade®), anti-IL12 antibodies, immunosuppressants (such as 6-mercaptopurine, azathioprine and cyclosporine A), and antibiotics.

Psoriasis

Psoriasis is a T lymphocyte-mediated inflammatory disease. Lesions contain infiltrates of T lymphocytes, macrophages and antigen processing cells, and some neutrophils. IL20 and its receptors are present in elevated levels in psoriatic lesions (Wei et al., Clin Immuno) (2005) 117: 65-72; Rømer et al., J Invest Dermatol 2003; 121, 1306-1311; Wang et al., J Invest Dermatol 2006; 126: 1590-1599; Otkjær et al., Br J Dermatol 2005; 153: 911-918).

Thus, in another aspect, the invention provides a method for treating and/or preventing psoriasis. The method comprises delivering an effective amount of an anti-hIL20 antibody to a human patient having psoriasis or being identified/diagnosed as being at substantial risk of developing psoriasis, such that psoriasis is treated or prevented in the patient. The antibody can be used alone or in combination with one or more other anti-psoriasis treatments such as phototherapy, topical therapy (e.g., tar, topical glucocorticoids), or systemic therapy (e.g., methotrexate, a synthetic retinoid, cyclosporine), an anti-TNFalpha agent (e.g., Embrel®, Humira®, Remicade®), a T-cell inhibitor (e.g., Raptiva®), vitamin D analogs, p38 mltogen-activated protein kinase (MAPK) inhibitors, as well as a biologic agent such as R1-tuxan®.

Psoriatic Arthritis

Psoriatic arthritis is a chronic inflammatory arthritic condition affecting the skin, the joints, the insertion sites of tendons, ligaments, and fascia, and is commonly associated with psoriasis. (Approximately 7% of patients with psoriasis develop psoriatic arthritis). Much evidence suggests that a T-cell-mediated process drives the pathophysiology of psoriatic arthritis. Monocytes also play a role in psoriatic arthritis and are responsible for the production of matrix metalloproteinases, which may mediate the destructive changes in the joints of patients with psoriatic arthritis.

Thus, in another aspect, the invention provides a method for treating and/or preventing psoriatic arthritis. The method comprises delivering an effective amount of an anti-hIL20 antibody to a human patient having psoriatic arthritis or being identified/diagnosed as being at substantial risk of developing psoriatic arthritis, such that the psoriatic arthritis is treated or prevented in the patient. The antibody can be used alone or in combination with one or more other anti-psoriatic arthritis treatments such as nonsteroidal anti-inflammatory drugs (aspirin, ibuprofen), methotrexate, a synthetic retinoid, cyclosporine, a corticosteroid, an anti-TNFalpha agent (e.g., Embrel®, Humira®, Remicade®).

Systemic Lupus Erythematosus

In systemic lupus erythematosus (SLE), the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Thus, in another aspect, the invention provides a method for treating and/or preventing SLE. The method comprises delivering an effective amount of an anti-hIL20 antibody to a human patient having SLE or being identified/diagnosed as being at substantial risk of developing SLE, such that the SLE is treated or prevented in the patient. The antibody can be used alone or in combination with other anti-SLE agents, such as non-steroidal anti-inflammatory drugs (NSAIDs), analgesics, corticosteroids (e.g., predinisone, hydrocortisone), immunosuppressants (such as cyclophosphamide, azathioprine, and methotrexate), antimalarials (such as hydroxychloroquine) and biologic drugs that inhibit the production of dsDNA antibodies (e.g. LIP 394).

Diabetes

Type I diabetes mellitus or insulin-dependent diabetes is the autoimmune destruction of pancreatic islet B cells; this destruction is mediated by auto-antibodies and autoreactive T cells. Antibodies to insulin or the insulin receptor can also produce the phenotype of insulin-non-responsiveness.

Thus, in another aspect, an anti-IL20 antibody is delivered to a patient suffering from or at substantial risk of developing type I diabetes mellitus in an amount and under conditions sufficient to treat or prevent the condition in the patient. The antibody can be used alone or in combination with other anti-diabetic agents, such as insulin, or beta cell growth or survival factors, or immunomodulatory antibodies such as anti-CD3 antibodies.

Transplantation

Transplantation associated diseases, including graft rejection and Graft-VersusHost-Disease (GVHD), is T lymphocyte-dependent; inhibition of T lymphocyte function is ameliorative.

Thus, in another aspect, the invention provides methods of reducing the likelihood of transplant rejection (or reducing the severity or prolonging the time to onset of a transplant rejection-related condition, i.e., to prolong allograft survival). The method comprises delivering an effective amount of an anti-hIL20 antibody to a human patient that is about to be, is, or recently was the recipient of a tissue/organ transplant, such that the likelihood of rejection is detectably reduced (e.g., as compared to a control). Examples of tissue transplants that can be treated include, but are not limited to, liver, lung, kidney, heart, small bowel, and pancreatic islet cells, as well as in bone marrow-transplantation and in the treatment of graft versus host disease (GVHD). The antibody can be used alone or in combination with other agents for inhibiting transplant rejection, such as immunosuppressive agents (e.g. cyclosporine, azathioprine, methylprednisolone, prednisolone, prednisone, mycophenolate mofetil, sirilimus, rapamycin, tacrolimus), anti-infective agents (e.g., acyclovir, clotrimazole, ganciclovir, nystatin, trimethoprimsulfarnethoxazole), diuretics (e.g. bumetanide, furosemide, metolazone) and ulcer medications (e.g., cimetidine, farnotidine, lansoprazole, omeprazole, ranitidine, sucralfate). For hematopoietic transplantation, hematopoietic growth factor(s) (e.g., erythropoietin, G-CSF, GM-CSF, IL3, IL11, thrombopoietin, etc.) or antimicrobial(s) (e.g., antibiotic, antiviral, antifungal) may be administered as an adjunct therapy.

Other Autoimmune or Inflammatory Diseases

In other separate aspects, the invention provides methods for treating and/or preventing other autoimmune or inflammatory diseases or disorders, comprising delivering an effective amount of an anti-hIL20 antibody to a human patient having the disease or disorder or being identified/diagnosed as being at substantial risk of developing the disease or disorder, such that it is treated or prevented in the patient, where the disease or disorder is one described below. The antibody can be used alone or in combination with one or more other therapeutic agents used for treating the disease or disorder.

Juvenile chronic arthritis is a chronic idiopathic inflammatory disease which begins often at less than 16 years of age. Its phenotype has some similarities to RA; some patients which are rhematoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing spondylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA B27 as if it were a foreign peptide expressed by MHC class I molecules. It has been hypothesized that an epitope of HLA-B27 may mimic a bacterial or other microbial antigenic epitope and thus induces a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often unregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjogren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or Fc-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of such a response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte dependent.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

It will be understood that the effective amount of the IL20 antibody, as well as the overall dosage regimen, may vary according to the disease and the patient's clinical status, which, in turn, may be reflected in one or more clinical parameters such as clinically accepted disease scores. For example, for rheumatoid arthritis, the severity of disease and/or outcome of treatment may be evaluated by monitoring number of swollen joints; pain; mobility; and/or the official disease score ACR 20/50 or 70. For Type 1 diabetes, severity of disease and/or outcome of treatment may be evaluated by measuring blood glucose levels or variations thereof, HbIC levels, the amount of insulin needed, and the like. For multiple sclerosis, brain inflammation can be assessed through scanning the brain. For hematopoietic transplant rejection, severity of the disease (failure to engraft) and/or outcome of treatment may be evaluated by evidence of prolonged neutropenia, thrombocytopenia, and red-cell transfusion dependence in patients that have undergone myeloablative conditioning, and by failure to observe chimerism in patients that have undergone non-myeloablative conditioning. In general, detectable effects on treatment outcome using the methods and compositions of the present invention include a decrease in the necessity for other treatments (including, e.g., a decrease in the amount and/or duration of other drugs or treatments), a decrease in number and/or duration of hospital stays, a decrease in lost work days due to illness, and the like. It will be further understood that the effective amount may be determined by those of ordinary skill in the art by routine experimentation, by constructing a matrix of values and testing different points in the matrix.

Dosages

For administration of the antibody, the dosage ranges from about 0.0001 to 100 mg/kg, and more usually 0.01 to 5 mg/kg, of the host body weight. For example, dosages can be about 0.3 mg/kg body weight, about 1 mg/kg body weight, about 3 mg/kg body weight, about 5 mg/kg body weight or about 10 mg/kg body weight or within the range of 1-10 mg/kg. An exemplary treatment regime entails administration twice per week, once per week, once every two weeks, once every three weeks, once every four weeks, once a month, once every 3 months or once every three to 6 months. Exemplary dosage regimens for an anti-hIL20 antibody of the invention include about 1, 3 or 10 mg/kg body weight body weight via intravenous administration or subcutaneous injection, with the antibody being given using one of the following dosing schedules: (i) loading doses every 1-3 weeks for 2-4 dosages, then every two months; (ii) every four weeks; (iii) every week, or any other optimal dosing. In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml. The antibody can alternatively be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

As will be understood by those of ordinary skill in the art, the appropriate doses of anti-cancer agents will approximate those already employed in clinical therapies wherein the anti-cancer agents are administered alone or in combination with other agents. Variation in dosage will likely occur depending on the condition being treated. The physician administering treatment will be able to determine the appropriate dose for the individual subject.

Articles of Manufacture

In another embodiment of the invention, an article of manufacture containing materials useful for the treatment of the disorders described above is provided. For example, the article of manufacture can comprise a container containing a human or humanized anti-hIL20 antibody as described herein together with instructions directing a user to treat a disorder such as an autoimmune or inflammatory disease or disorder in a human with the antibody in an effective amount. The article of manufacture typically comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example, the container may be an intravenous solution bag or a vial having a stopper pierceable by a hypodermic injection needle). At least one active agent in the composition is the human or humanized anti-hIL20 antibody herein, or an antigen-binding fragment or antibody derivative (e.g., an immunoconjugate) comprising such an antibody. The label or package insert indicates that the composition is used for treating the condition of choice, such as, e.g., rheumatoid arthritis, juvenile rheumatoid arthritis, psoriasis, psoriatic arthritis, ankylosing spondylitis, Sjögren's syndrome, multiple sclerosis, inflammatory bowel disease, systemic lupus erythematosus, lupus nephritis, or a combination thereof.

Moreover, the article of manufacture may comprise (a) a first container with a composition contained therein, wherein the composition comprises the human or humanized antibody herein, and (b) a second container with a composition contained therein, wherein the composition comprises a therapeutic agent other than the human or humanized antibody. The article of manufacture in this embodiment of the invention may further comprise a package insert indicating that the first and second compositions can be used in combination to treat an autoimmune or inflammatory disease or disorder. Such therapeutic agents may be any of the adjunct therapies described in the preceding section. Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Further details of the invention are illustrated by the following non-limiting Examples.

Example 1

Inhibition of IL20-Induced Proliferation by Human Anti-hIL20 Antibodies

A series of tests were performed to investigate the ability of human anti-hIL20 monoclonal antibodies to neutralize the effect of hIL20 induced proliferation of BaF-3 cells transfected with IL20R1+hIL20R2 (herein "hIL20R").

Material & Methods
Media and Buffers.

Culture medium: Roswell Park Memorial Institute (RPMI 1640) with Glutamax, 10% heat inactivated foetal bovine serum (FBS), 1% penicillin/streptomycin (P/S) (BioWhitaker Cat.No. DE17-602E), 1 mg/ml Geneticin (GIBCO Cat.No. 10131-019), 200 µg/ml Zeocin (Invitrogen 45-0430), 1 ng/ml murine IL-3 (TriChem ApS Cat.No. 213-13), 50 µM 2-Mercapto-ethanol (Gibco Cat.No. 31350-010). Assay medium: RPMI 1640 with Glutamax, 10% heat inactivated FBS, 1% P/S (BioWhitaker Cat.No. DE17-602E), 1 mg/ml Geneticin (GIBCO Cat.No. 10131-019), 200 µg/ml Zeocin (Invitrogen 45-0430), 50 µM 2-Mercapto-ethanol (Gibco Cat. No. 31350-010). AlamarBlue dye: (BioScource, Dal1100) was used to assess proliferation. The fluorescence intensity was measured on a spectrofluorometer (bmg POLARstar+ Galaxy) at excitation 555-12 nm and emission 590 nm.

Antibodies, Cells and Cytokines.

Mice were immunized by injecting subcutaneously 20 µg of human IL-20 in FCA followed by two injections with 20 µg of hIL20 in FIA. Highresponder mice were boosted intravenuosly with 25 µg of hIL20 and the spleens were harvested after 3 days. Spleen cells were fused with the myeloma cell line (Köhler, G & Milstein C. (1976), European J. Immunology, 6:511-19). Supernatants were screened for human IL-20 antibody production in an indirect hIL20-specific ELISA, and purified. Rabbit anti-hIL20 polyclonal antibody (pAb) was produced by immunizing rabbits four times with 50 µg hIL20 at 14 days intervals and five times with 10 µg/ml hIL20 once monthly. The serum was purified (2313B). BaF-3 (hIL20R) cells were from a BaF-3 cell line transfected with the genes for hIL20R1 (Zcytor7) and hIL20R2 (Dirs1) and the plasmid KZ134 that bears luciferase under control of the signal transduction and transcription protein (STAT)-promotor elements. The BaF-3 cell line was generated by selection in pyromycin (Zcytor7) and zeozin (Dirs1) and received from Zymogenetics Institute.

Stimulation Assay.

An initial stimulation assay was made to assess the level of hIL20 to be used in the inhibition assay. BaF-3(hIL20R) cells were washed thoroughly in assay medium to get rid of residual IL-3. The cells were then seeded into 96-well microtiter plates (flat-well view plate Packard cat.S00190) at $10^4$–$5 \times 10^4$ cells/well. Serial dilutions of hIL20 ($10^{-7}$M to $10^{-13}$M) were added to the wells and additional wells with cells but no hIL20 served as negative control. The cells were cultured for three days in 5% $CO_2$ at 37° C. For the last 6 hours of the culture period, 10 µl alamarBlue was added to each well. The cells were analyzed for fluorescence intensity on a spectrofluorometer (bmg POLARstar+ Galaxy) at excitation 555-12 nm and emission 590 nm. For inhibition analysis, a constant concentration of IL20 was used to stimulate the cells. This concentration was chosen on basis of approximately 90% of max stimulation in the proliferation assay which in most of our assays corresponded to $10^{-9}$M hIL20.

Inhibition Assay.

$1 \times 10^4$–$5 \times 10^4$ cells/well of washed BaF-3(hIL20R) cells were added to microtiter wells in assay medium and $10^{-9}$M hIL20 (final concentration) was added to each well except for wells used as negative control containing only cells. This concentration corresponded to approx. 90% of maximum stimulation with the hIL20 cytokine. Serial dilutions of antibody (i.e., 100 µg and 2-fold dilutions) were added to the wells already containing cells and cytokines (except wells used for positive controls containing only cells+hIL20). The mixture of cells, cytokine and antibody were incubated in 100 µl/well for 72 hours in 5% $CO_2$ at 37° C. The last 6 hours of incubation included 10 µl/well of alamarBlue. The plates were analysed for fluorescence intensity on a spectrofluorometer (bmg POLARstar+ Galaxy) at excitation 555-12 nm and emission 590 nm. The curves were drawn and the potency (half maximal inhibition ($IC_{50}$)) was calculated using Prism 4 (GraphPad PRISM software Inc.). Efficacy was calculated as 1−(max inhibition of antibody/(initial stimulation of cytokine−no stimulation of cytokine))*100%.

Results

An initial stimulation of BaF-3(hIL20R) at $10^{-9}$M hIL20 was chosen from dose response curves. The results from a series of inhibition assays are shown in Table 1. The potency ($IC_{50}$) varied among the different inhibitory antibodies. 15D2 was one of the most potent inhibitors, and had the lowest interassay variation. 15D2 also had a high affinity compared to the polyclonal rabbit anti-hIL20 antibody preparation.

TABLE 1

Inhibition of hIL20 induced proliferation

| Anti-IL20 | Inhibition of IL20 induced proliferation at 1e−9M hIL20, IC50 (uM) | | | | | | |
|---|---|---|---|---|---|---|---|
| | 1 | 2 | 3 | 4 | 5 | 6 | 7 |
| 2F6 | 15.4 | 13.88 | 1.67 | 0.36 | 1.8 | 0.32 | 15.38 |
| F56 (LC: F56Type1; HC: F56) | | | | 0.04 | 0.73 | | |
| F18 (LC: F56Type1; HC: F18) | | | | | 0.05 | | |
| C3 | — | — | — | | | — | |
| 5B7 | 0.26 | 4.54 | 0.76 | | | 0.2 | |
| 15D2 | 0.18 | 0.42 | 0.34 | | | 0.12 | 0.4358 |
| C11 | 0.26 | 2.0 | 0.37 | | | | 0.1860 |
| F18 (from hybridoma) | | | | 0.12 | 0.09 | | |
| F56 (from hybrodima) | 4.97 | | | | | | |
| 41A6 | | 5.36 | 3.12 | 1.32 | | | 3.118 |
| 41F10 | | 5 | 4.7 | 2.55 | | | |
| 42A5 | | 0.66 | 0.21 | | | | |
| 54F10 | | | | | | | 2.560 |
| 24 | | | | | | | 4.971 |

Example 2

Comparative Inhibition of IL20-, IL19- or IL24-Induced Proliferation

Human antibody 15D2 was tested for its ability to neutralize cynomolgus IL20 and mouse IL20. Both mouse and cynomolgus IL20 are able to induce proliferation in BaF-3 (hIL20R) cells. 15D2 was also tested for inhibition of proliferation induced by hIL19 or hiL24 on BaF-3(hIL20R). Both hiL24 and hIL19 bind the hIL20R1+hIL20R2 receptor.

Material & Methods
Media and Buffers.
See Example 1.
Antibodies, Cells and Cytokines.
See Example 1. Human and cynomolgous IL20 were produced in *E. coli*. Mouse IL20 was from BioSource International Inc. Human IL19 and IL24 were from R&D systems.
Stimulation Assay.
An initial stimulation assay was made to asses the initial concentration of hIL20, cynomolgus IL20 and mouse IL20 to be used in the inhibition assay, using the same initial stimulation assay described in Example 1. Initial stimulation with hIL19 and hiL24 was assessed by the same method. It was decided to use three different initial concentrations of IL19 and hiL24 in the inhibition assay.

Inhibition Assay.

(1) Effect on anti-hIL20 mAb on cynomolgus IL20 and mouse IL20 induced proliferation: $1\times10^4$–$5\times10^4$ cells/well of washed BaF-3(hIL20R) cells were added to microtiter wells in assay medium and, $10^{-9}$M hIL20, cynomolgus IL20 or mouse IL20 (final concentration) was added to each well except for wells used as negative controls containing only cells. This concentration corresponded to approx. 90% of maximum stimulation with the cytokines. Serial dilutions of antibody 1400-250-15D2 (100 µg and 2-fold dilutions) were added to the wells already containing cells and cytokines (except wells used for positive controls containing only cells+cytokines).

(2) Effect on anti-hIL20 mAb on hIL19 and hiL24 induced proliferation:$1\times10^4$–$5\times10^4$ cells/well of washed BaF-3 (hIL20R) cells were added to microtiter wells in assay medium and three different concentrations of cytokine ($10^8$M, $10^{-9}$M and $10^{-10}$M final concentration) of either hIL20, hIL19 or hiL24 was added to each well, except for wells used as negative controls and containing only cells. This concentration corresponded to approximately 90% of maximum stimulation with the cytokines. Serial dilutions of antibody 15D2 (100 µg and 2-fold dilutions) were added to the wells already containing cells and cytokines (except wells used for positive controls containing only cells+cytokines).

For both assays, the mixture of cells, cytokine and antibody were incubated in 100 µl/well for 72 hours in 5% $CO_2$ at 37° C. The last 6 hours of incubation included 10 µl/well of alamarBlue. The plates were analysed for fluorescence intensity on a spectrofluorometer (bmg POLARstar+ Galaxy) at excitation 555-12 nm and emission 590 nm. The curves were drawn and the potency (half maximal inhibition ($IC_{50}$)) was calculated using Prism 4 (GraphPad PRISM software Inc.).

The efficacy (the percentage inhibition by antibodies) was calculated as 1–(max inhibition of antibody/(initial stimulation of cytokine–no stimulation of cytokine))*100%.

Results

Effect of Anti-hiL20 mAb on Cynomolgus IL20 and Mouse Il20 Induced Proliferation.

When BaF-3(hIL20R) cells were stimulated with human, cynomolgus or mouse IL20, the cells proliferated and this proliferation could be inhibited by anti-hIL20 mAb 15D2 in a dose dependent manner. The efficacy of 15D2 was near 100% at 66 mM IL20 for all three cytokines. The potencies of the antibody could not be directly compared since the affinity for the hIL20R was different for the three cytokines.

Effect of Anti-hIL20 mAb on hIL19 and hiL24 Induced Proliferation.

Figure 5A:
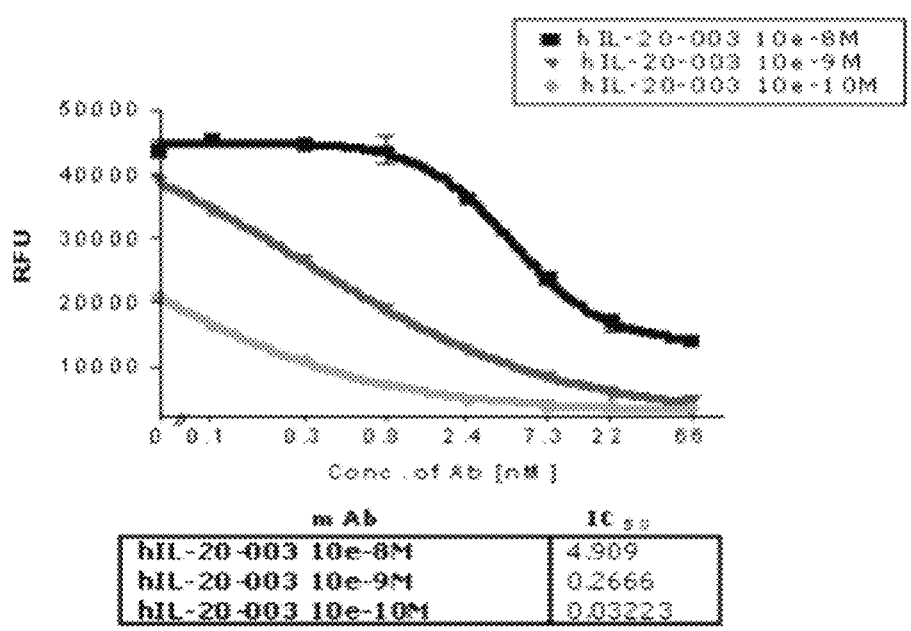
FIG. 5 shows the ability of 15D2 to inhibit hIL20—(A), hIL19—(B), and hIL24—(C) induced proliferation of BaF-3 cells transfected with hIL20R1/hIL20R2 at three different cytokine concentrations. (A) A dose-dependent response was detected for inhibition of hIL20-induced proliferation. No inhibition of hIL19—(B) or hIL24—(C) induced proliferation was observed in 15D2-concentration range used (up to 66 nM).
Figure 5B:
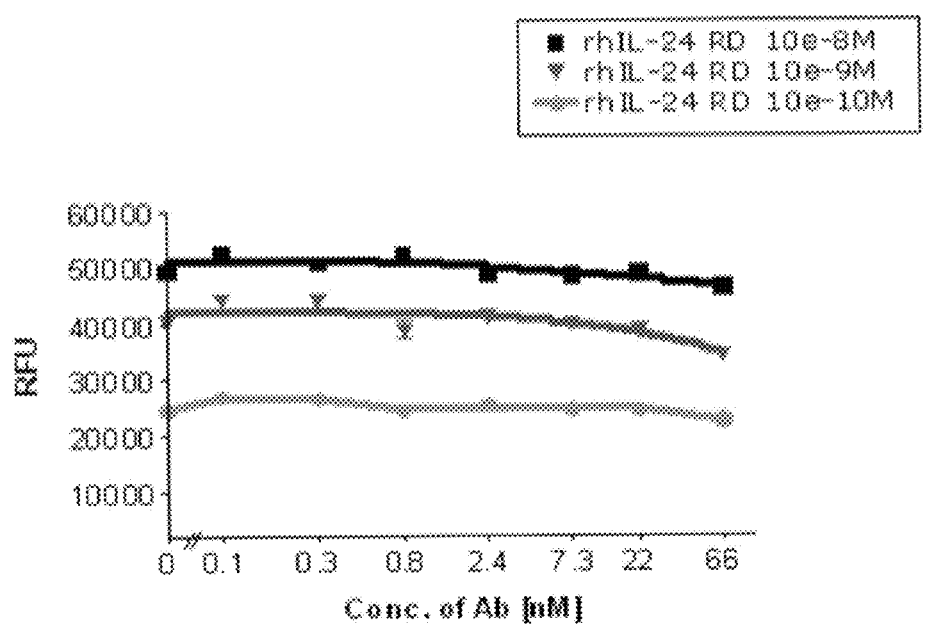
Figure 5C:
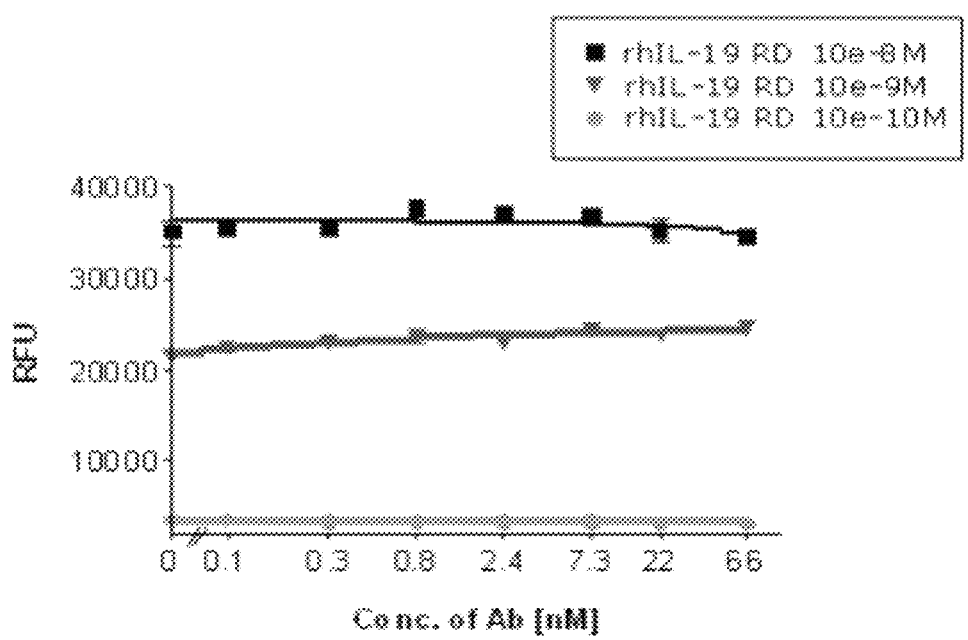

BaF-3(hIL20R) cells were stimulated with three different concentrations of hIL20, hIL19 or hiL24 (FIG. 5). A dose-dependent response was detected for inhibition of hIL20 induced proliferation (FIG. 5A). This experiment served as positive control for the subsequent hIL19 and hiL24 experiments. When the BaF-3(hIL20R) cells initially were stimulated with hIL19, 15D2 was not able to inhibit the proliferation regardless of which of the three initial concentrations of hIL19 were used (FIG. 5B). The same results were obtained when the cells initially were stimulated with hiL24 (FIG. 5C).

Accordingly, 15D2 inhibited cynomolgus IL20-induced as well as mouse IL20-induced proliferation of the BaF-3 (hIL20R) cells, while hIL19 or hIL24-induced proliferation of BaF-3(hIL20R) was not inhibited by 15D2.

Example 3

Solubility

Figure 4A:
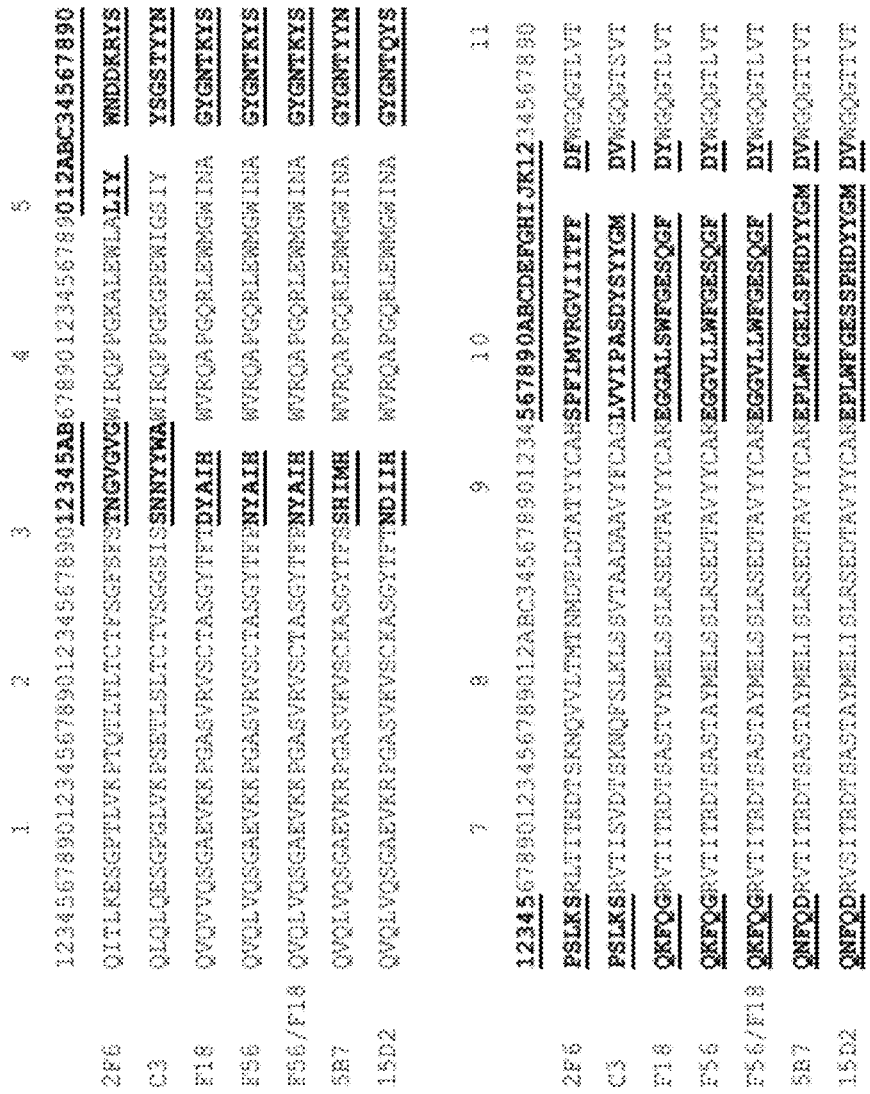
FIG. 4 shows an alignment of VH (A) and VL (B) region sequences of several human anti-IL20 antibodies of IgG4 isotype with the corresponding Kabat-numbering of each amino acid position. In each sequence, the corresponding CDR sequences according to the Kabat scheme are shown in bold, underlined text. (A) Heavy chain variable sequences for 2F6 (SEQ ID NO:18), C3 (SEQ ID NO:20), F18 (SEQ ID NO:22), F56 and F56/F18 (SEQ ID NO:23), 5B7 (SEQ ID NO:7), and 15D2 (SEQ ID NO:6), (B) Light chain variable sequences for 2F6 (SEQ ID NO:19), C3 (SEQ ID NO:21), F56_type 1, 15D2, and 5B7 (SEQ ID NO:9), and F56_type 2 (SEQ ID NO:24).

Seven different human IgG4 antibodies against IL20, produced in HEK293 cells and purified by the same process, were compared for their ability to reach high concentration in solution, by using centrifuge filters of the type Amicon Ultra (Millipore Corp, MA) with a cut-off weight of 50 kD. All samples were centrifuged according to manufacturer instructions for 1 hour. The initial concentration of the antibodies ranged from 0.5 to 1.8 mg/ml, and all antibodies were formulated in 20 mM Na-Phosphate, 150 mM NaCl at pH 7.4. The VH and VL sequences of the tested antibodies are shown in FIGS. 4A and 4B, respectively.

Table 2 shows the concentrations and recoveries obtained after concentrating human anti-IL20 IgG4 antibodies using Amicon Ultra 50 kD centrifuge filters. The highest concentration (above 100 mg/ml) was reached for 15D2, followed by 5B7 at above 80 mg/ml, both of which also had a high recovery. All antibodies retained its monomeric structure at the higher concentration as seen with dynamic light scattering analysis, except 2F6, which showed signs of increased dimerization.

TABLE 2

Solubility and recovery of human anti-hIL20 antibodies

| Anti-IL20 | Concentration (mg/ml) | Recovery (%) |
|---|---|---|
| 2F6 | 50 | 80 |
| F56 (HC: F56; LC: F56type1) | 14 | 48 |
| F18 (HC: F18; LC: F56type1) | 31 | 64 |
| F56/F18 (HC: F56/F18; LC: F56Type1) | 24 | 42 |
| C3 | 53 | 80 |
| 5B7 | 84 | 79 |
| 15D2 | 109 | 81 |

Analysis of the variable region amino acid and/or nucleic acid sequences of the antibody heavy and light chain variable regions revealed the germline sequences shown in Table 3. An additional antibody, C11 (see Example 1) was also sequenced, revealing a HC having the sequence of SEQ ID NO:25 and the same VL as F56Type1.

TABLE 3

VL, VH, and germline sequences of human anti-IL20 antibodies

| | Germline |
|---|---|
| Light Chain | |
| 2F6 (SEQ ID NO: 19) | VKI_L24/JK4 |
| C3 (SEQ ID NO: 21) | VKIII_L6/JK2 |
| F56type1, 15D2, and 5B7 (SEQ ID NO: 9) | VKI_L18/JK4 |
| F56type2 (SEQ ID NO: 24) | VKIII_A27/JK1 |
| Heavy chain | |
| 2F6 (SEQ ID NO: 18) | VH2_05/D3_10/JH4 |
| C3 (SEQ ID NO: 20) | VH4_39/D_/JH6 |
| F18 (SEQ ID NO: 22) | VH1_03/D_/JH4 |
| F56 and F56/F18 (SEQ ID NO: 23) | VH1_03/D_/JH4 |
| 5B7 (SEQ ID NO: 7) | VH1_03/D3_10/JH6 |
| 15D2 (SEQ ID NO: 6) | VH1_03/D3_10/JH6 |

Example 4

Binding of Antibodies to hiL20

A Surface Plasmon Resonance (SPR) experiment was performed on a BiacoreT100, in order to determine whether individual human anti-hIL20 antibodies were able to bind simultaneously to recombinant hIL20. For comparison, three IL20R1/IL20R2-neutralizing rat anti-hIL20 mAbs, designated 262.4.1.2.2.1, 262.5.1.6.4.4 and 262.7.1.3.2.4 and described in WO2005/052000, were included. An inability to bind simultaneously indicates common or overlapping epitopes, though factors such as steric hindrance and conformational changes may contribute.

Materials & Methods

The experiment was performed on a CM5 chip with immobilized anti-hIL20 antibodies. Each antibody was immobilized on separate chips to a level of ~1000 RU by standard amine coupling. All samples were diluted in running-buffer, HBS-EP pH 7.4 (10 mM HEPES, 150 mM NaCl, 3 mM EDTA and 0.005% Polysorbat P20). Recombinant hIL20 (10 µg/ml) was injected for 180 s, followed by injection of 15D2 (10 µg/ml) for 180 s.

Results

The human antibodies 15D2 and 5B7 were not able to bind simultaneously to recombinant hIL20, indicating a common or overlapping epitope. In contrast, 15D2 was able to bind simultaneously with each of 262.4.1.2.2.1, 262.5.1.6.4.4 or 262.7.1.3.2.4 mAbs, indicating that the epitope of 15D2 was different from that of 262.4.1.2.2.1, 262.5.1.6.4.4 and 262.7.1.3.2.4.

Example 5

Binding of Antibodies to Denatured Hil20

This experiment was conducted to determine whether the human anti-IL20 antibodies also bound fully denatured antigen. If no binding activity could be detected, then peptide arrays would not be appropriate for epitope mapping (see below). In order to test for binding to the denatured antigen, native and denatured hIL20 preparations were subjected to SDS-PAGE, followed by Western-blot using 15D2 and 5B7 for detection.

Materials & Methods

Recombinant hIL20 was denatured by boiling for 10 min. in sample buffer (NuPage, Invitrogen) containing 50 mM DTT. The samples were run in SDS-PAGE (20 ul/well including sample-buffer) and blotted to a nitrocellulose membrane. The membrane was incubated with the primary mAb (10 µg/ml in blotting buffer (Novex, Invitrogen)), followed by incubation with HRP-conjugated Rabbit anti-human IgG polyclonal Ab (DAKO). Bands were visualized using TMB-substrate (Kem-En-Tech).

Results

Both 15D2 and 5B7 recognized the native- and denatured form of the antigen, indicating that the epitope is continuous (linear).

Example 6

Surface Plasmon Resonance Analysis of Peptide Binding

An SPR experiment was performed in order to determine whether the anti-hIL20 antibodies 15D2, 262.4.1.2.2.1, 262.5.1.6.4.4 or 262.7.1.3.2.4 bound to the region corresponding to residues 42-102 of the unprocessed precursor of hIL20 (SEQ ID NO:2), corresponding to residues 18-78 of mature hIL20 (SEQ ID NO:1). The antibodies were shown to recognize both the native and denatured form of hIL20 (for 15D2, see above).

Materials & Methods

Five 20mer peptides with a frame shift of 10 residues were synthesized:

```
                    (residues 18-37 of SEQ ID NO: 1)
1) IRNGFSEIRGSVQAKDGNID (residues 28-47 of SEQ ID NO: 1)
2) SVQAKDGNIDIRILRRTESL (residues 38-57 of SEQ ID NO: 1)
3) IRILRRTESLQDTKPANRSS (residues 48-67 of SEQ ID NO: 1)
4) QDTKPANRSSLLRHLLRLYL (residues 58-78 of SEQ ID NO: 1)
5) LLRHLLRLYLDRVFKNYQTPD
```

The peptides, containing N-terminal biotin, were immobilized (500 RU) in individual flow cells on streptavidin coated (SA) chips. The individual antibodies (5 µg/ml) were injected across all flow cells for 120 s, followed by a 180 s dissociation phase. Experiments were performed on Biacore3000 and BiacoreT100 instruments. The results were evaluated using Scrubber2 software (BioLogic Software Pty Ltd).

Results

No 15D2, 262.5.1.6.4.4 or 262.7.1.3.2.4 binding to the peptides was detected. The rat anti-hIL20 mAb 262.4.1.2.2.1 demonstrated binding to peptide 4 and 5, indicating binding to their shared sequence LLRHLLRLY. All mAbs demonstrated binding to immobilized intact biotinylated IL20.

Example 7

Primary Peptide Array ("Peptide Walk")

A peptide array consisting of 18mer hIL20 peptides with a frame shift of 4 residues was made and screened against fluorescence-labelled anti-hIL20 antibodies 15D2 or 5B7.

Materials and Methods

Synthesis of Epitope Arrays.

The epitope mapping arrays were synthesized on cellulose sheets (Aims-Scientific, Germany) on an array synthesizer (Multipep Spot, Intavis, Germany) essentially using the protocols provided from the manufacturer. Fmoc-amino acids were purchased from Novabiochem (Germany) and dissolved in N-methylpyrrolidinone (NMP) containing 0.3 M Hydrobenzotriazole (HOBt) to a final concentration of 0.3M. Coupling was done by activating with diisopropylcarbodiimide (DIC), and deprotection of the Fmoc group was done by 20% piperidine in NMP. The individual sequences were designed by the software accompanying the array synthesiser. After synthesis the protecting groups were removed by treating the sheets with trifluoroacetic acid (TFA) 95% containing triisopropylsilane (TIPS) for 60 min. Then washed with dichloromethane (DCM) and N-methylpyrrolidinone (NMP) and finally with water.

Labelling of Antibodies.

The screenings were done using fluorescence labelled antibodies. The labelling was done by gel-filtering the antibody stock against 1% NaHCO3, using NAPS column (GE Healthcare according the manual from manufacturer. This was followed by adding 25 mole equivalents of 5(6)-carboxyfluorescein N-hydroxysuccinimide ester (Sigma, C1609) dissolved in DMSO. The coupling was allowed to continue for 2 hours followed by a gelfiltration against TRIS washing buffer (50 mM TRIS, pH=7.4, 0.15M NaCl, 0.1 M ArgHCl, 0.05% Tween 20) in order to removed uncoupled fluorescein.

Screening and Analyzing Arrays.

Screening of arrays were done by adding 10 µl of antibody to 30 ml incubation buffer (0.5% BSA, 50 mM TRIS, pH=7.4, 0.15M NaCl, 0.1 M ArgHCl, 0.05% Tween 20). The sheets were incubated for 1-2 hours, followed by washing five times with washing buffer. Then the sheets were scanned using a laser scanner (Typhoon 9410, GE Healthcare) and the image file (.gel format) was analysed using dedicated array software ArrayPro Analyzer (Media Cypernetics, USA). The fluorescence intensity were measured and transformed into digits that were exported to Prism 5 (GraphPad Software, USA) for further analysis.

Results

Figure 6A:
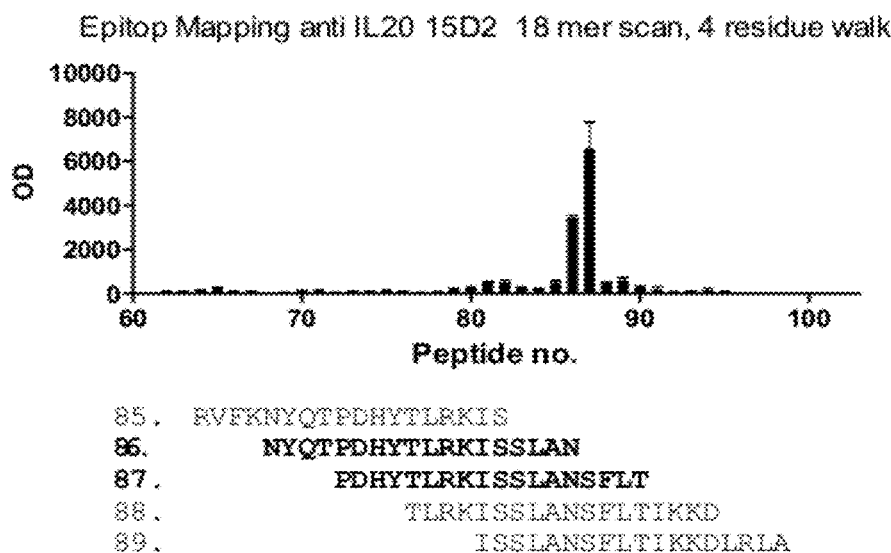
FIG. 6 shows the results of a primary peptide array of hIL20 against 15D2 (A) or 5B7 (B). The Y axis indicates the optical density (OD, a measure of fluorescence intensity). Note that not all peptides are present in figure, since some OD values were below detection limit. In (A), peptides corresponding to residues 69-86 (85), 73-90 (86), 77-94 (87), 81-98 (88), and 85-102 (89) of SEQ ID NO:1 are shown. Peptide 87 came out as the peptide with highest binding activity. In (B), peptides corresponding to residues 49-66 (19), 53-70 (20), 57-74 (21), 69-86 (24), 73-90 (25), and 77-94 (26) are shown.
Figure 6B:
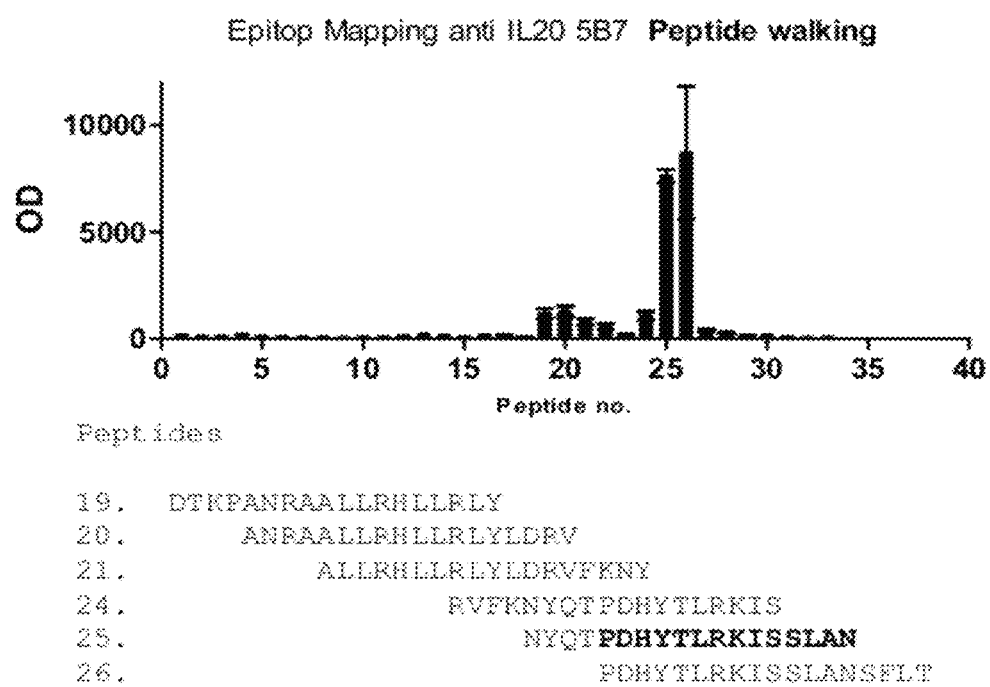

The results from the primary peptide array analysis, shown in FIG. 6, clearly identified that 15D2 and 5B7 both bind a linear epitope located in the region corresponding to residues 73-96 in mature hIL20 (SEQ ID NO:1), corresponding to residues 97-120 of the precursor (SEQ ID NO:2).

Example 8

Secondary Peptide Array Analysis—Terminal Deletions

In order to narrow down the length of the epitope and to evaluate which residues were important for the binding of anti-IL20 antibodies 15D2 and 5B7, an array of various truncations was made. An ala-scan was also included (section 5).

For Materials and Methods, see Example 7.

Results

Figure 7A:
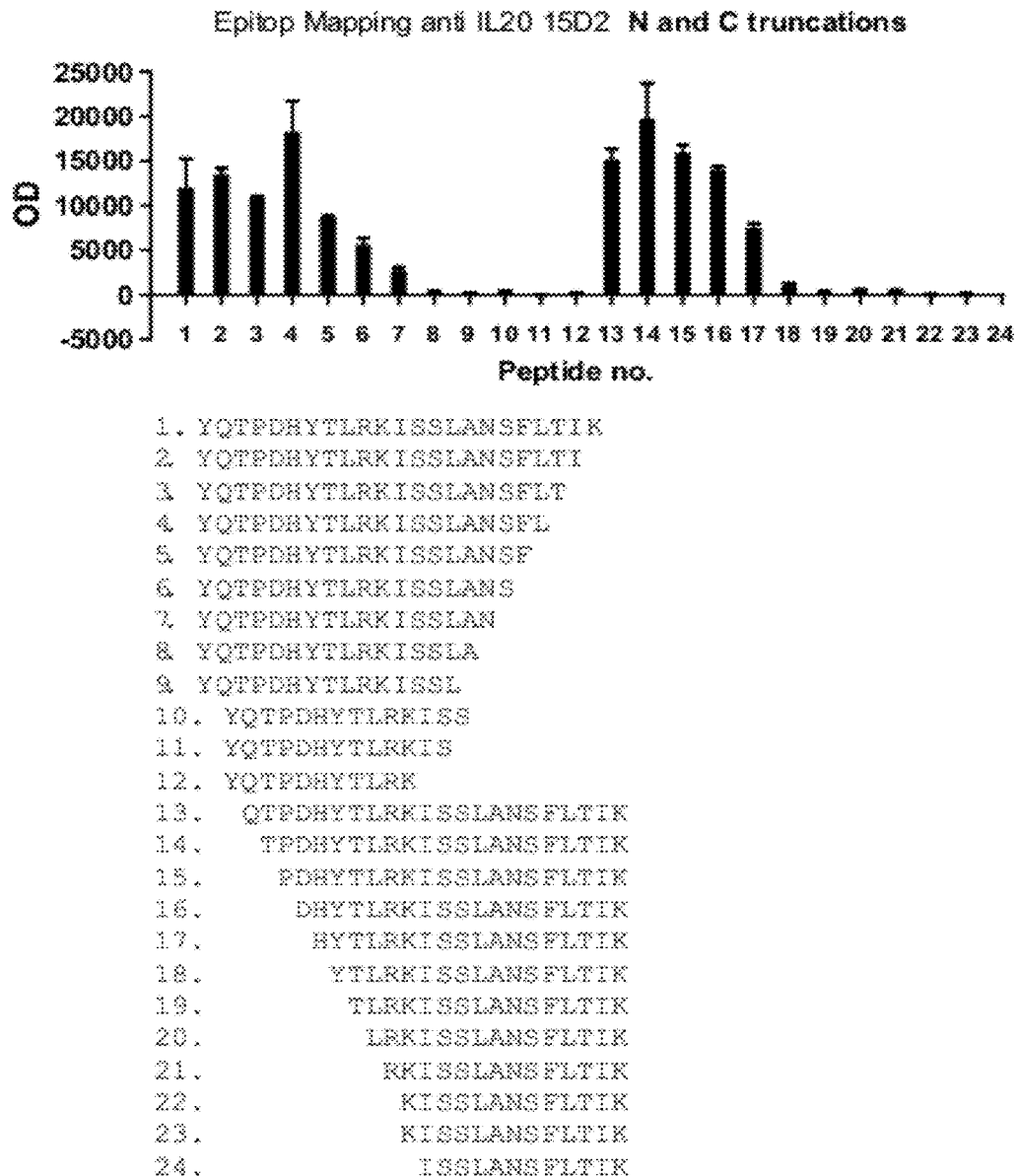
FIG. 7 shows a secondary peptide array analysis of hIL20 against 15D2 (A) or 5B7 (B). The antibodies were tested against constructs with truncations from the C- and N-terminal. The peptides were all acylated in order to avoid the positive charge arising from the N-terminal. In (A), peptides corresponding to Y74 to K96→S86 and K84 of SEQ ID NO:1 (peptides 1-12, respectively) are shown on the left-hand column, and peptides corresponding to Q75→I85 to K96 of SEQ ID NO:1 (peptides 13-24, respectively, where peptides 22 and 23 are identical) are shown in the right-hand column. In (B), peptides corresponding to Y74 to K96→S86 and K84 of SEQ ID NO:1 (peptides 1-12, respectively) are shown on the left-hand column, and peptides corresponding to Q75→S84 to K96 (peptides 13-24, respectively, where peptides 22 and 23 are identical) are shown in the right-hand column.

The truncations from the hIL20 C-terminal revealed a gradual reduction in 15D2 binding from peptides 4 to 7 (FIG. 7A). A more sudden decline in binding activity was seen for the N-terminal truncations, where removal of D (Asp) and H(His) dramatically reduced the affinity. Overall, the results showed that the minimum epitope had the sequence DHYTL-RKISSLANSFL, corresponding to residues 78 to 93 of SEQ ID NO:1.

Figure 7B:
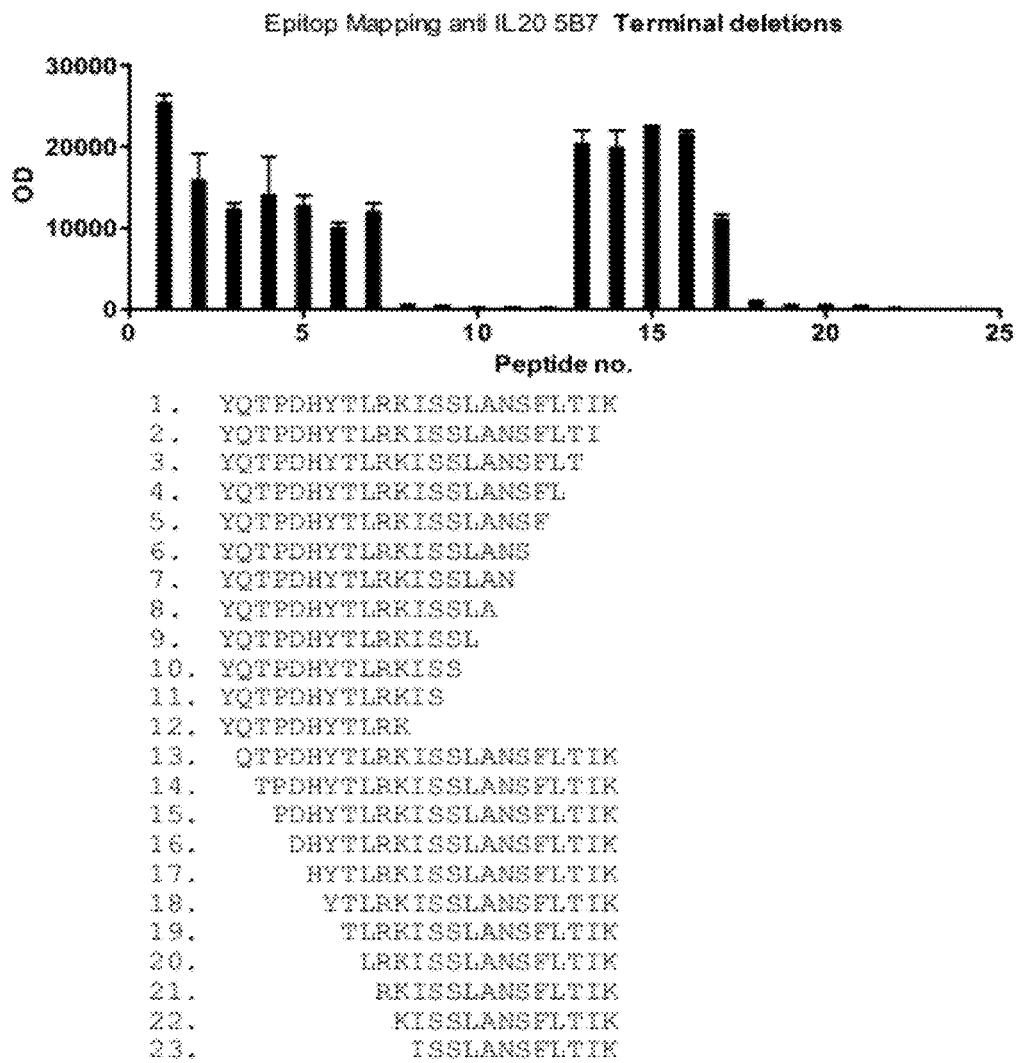

For 5B7, the truncations revealed a sudden reduction in binding when deleting from the N-terminal (FIG. 7B). A decline of about 50% in binding activity was seen for the N-terminal truncations when removing D (Asp), and removing H(His) dramatically reduced the affinity to no detectable binding. Removing from the C-terminal resulted in a less sudden decline in affinity until removing N (Asn). Overall, the results indicate that the minimum 5B7 epitope had the sequence DHYTLRKISSLAN (residues 78-90 of SEQ ID NO:1), although a longer epitope, DHYTLRKISSLANSFL-TIK (residues 78-96 of SEQ ID NO:1), did present a higher affinity. This indicated the presence of some structural requirements, e.g., α-helix dependence.

Figure 8A:
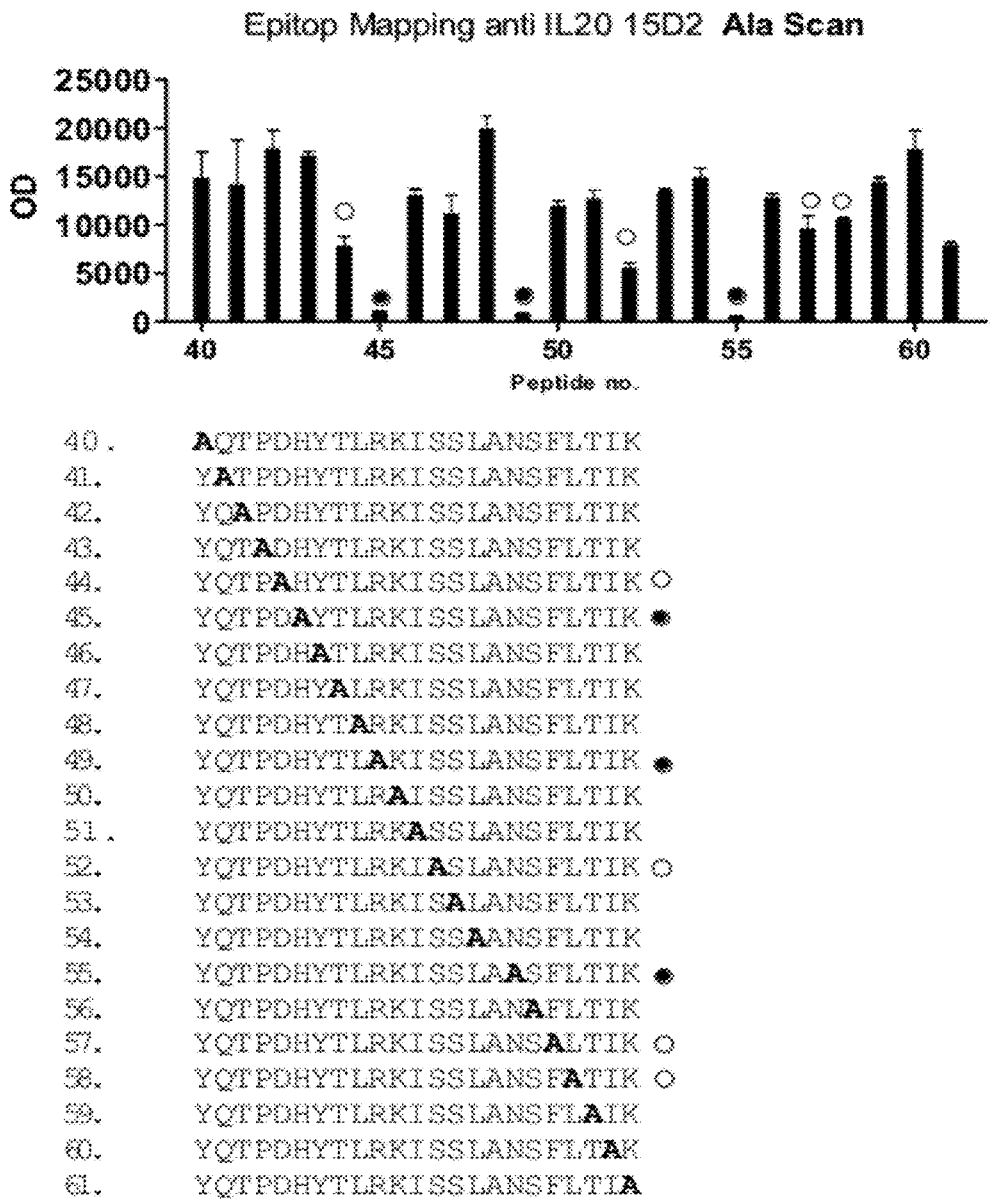
FIG. 8 shows an Ala-scan of the long epitope YQTP-DHYTLRKISSLANSFLTIK, corresponding to residues Y74 to K96 of SEQ ID NO:1, against (A) 15D2 and (B) 5B7. In (A), the peptides shown correspond to residues 78-96 of SEQ ID NO:1 with an alanine substitution at positions 78-96, peptides 40-61, respectively. In (B), the peptides shown correspond to residues 78-96 of SEQ ID NO:1 with an alanine substitution at positions 78-96, peptides 1-22, respectively.
Figure 8B:
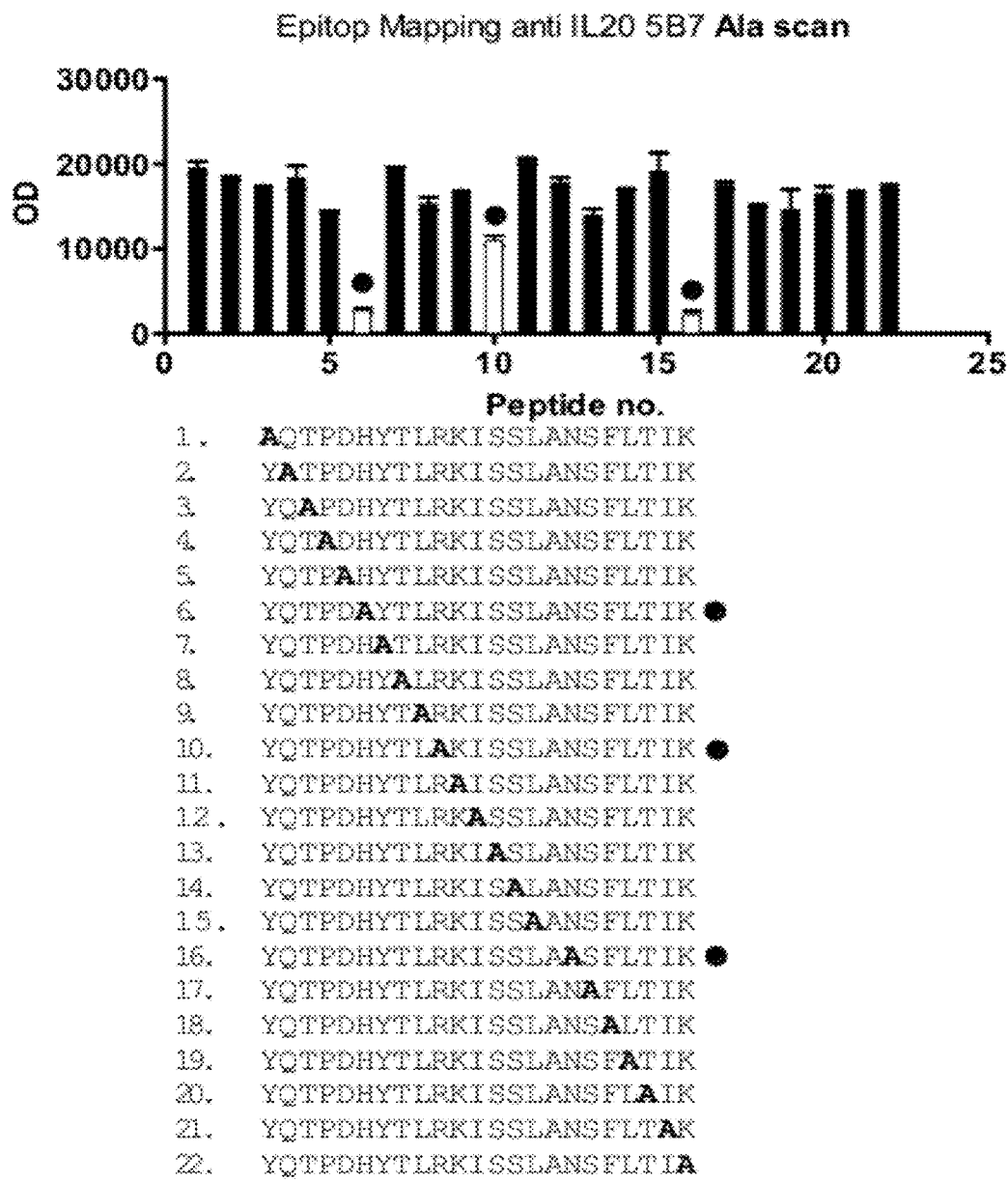

The result of the Ala scan clearly indicated that, for 15D2, three residues, H79 (His-79), R83 (Arg-83) and N90 (Asn-90) of SEQ ID NO:1 were most critical for binding (FIG. 8A). Also sensitive, but to a lesser extent, were residues D78 (Asp-78), S86 (Ser-86), F92 (Phe-92) and L93 (Leu-93). The residues H79 and N90 were most critical also for 5B7 binding, while R83 (Arg) appeared fairly critical (FIG. 8B).

In conclusion, the human anti-hIL20 antibodies 15D2 and 5B7 both bind a linear epitope (functional) of similar length and specificity, shown in FIG. 1. Residues H79, R83 and N90 (bold and single-underlined) of mature hIL20 (SEQ ID NO:1); corresponding to H103, R107, and N114 in hIL20 precursor (SEQ ID NO:2), were found the most critical, with residues D78, S86, F92 and L93 (bold and double-underlined) being moderately critical. The main difference between the two antibodies was that R83 was slightly less critical for 5B7 binding as compared to 15D2 binding.

The position of the 15D2/5B7 epitope and the location of the most critical residues were revealed using the crystal structure of the homologous protein IL19 (Chang et al. J Biol Chem 2003; 278: 3308). It was found that the location of the epitope corresponded to helix E in IL19, and that the most critical residues in hIL20; H79, R83, and N90 of SEQ ID NO:1, are exposed to the solvent. Note that the hIL20 residue H79 is a proline in hIL19.

Example 9

Neutralization of IL20 Activation of IL20R1/IL20R2 and IL22R1/IL20R2 Receptor Complexes This Example shows that human antibody 15D2 is capable of neutralizing murine, cynomolgous, and hIL20 activation of recombinantly expressed IL20R1/IL20R2 and IL22R1/IL20R2 receptor complexes.

Materials and Methods

Cloning of IL20 Receptors.

Human IL20 receptors, IL22R1 (EMBL BC029273), IL20R1 (EMBL AF184971) and IL20R2 (EMBL AY358305) were PCR-amplified from NHEK (Normal Human Epidermal Keratinocyte) cDNA and cloned into pcDNA3.1+(zeocin) (IL22R1 and IL20R1) and pcDNA3.1+(hygro)(IL20R2). Mouse IL20 receptors, mIL22R1 (EMBL AY103454), mIL20R1 (EMBL AK054215) and mIL20R2 (EMBL BC107264) were cloned by PCR using mouse liver, testis and skin cDNA, respectively, as templates. Each of these IL20R sequences is incorporated by reference, in its entirety. The mIL22R1 and mIL20R1 PCR-product were cloned into pcDNA3.1+(zeo) and mIL20R2 into pcDNA3.1+(hygro). Cynomolgus IL20 receptors, cynoIL22R1 (SEQ ID NO:28), cynoIL20R1 (SEQ ID NO:26) and cynoIL20R2 (SEQ ID NO:27) were cloned by PCR using cynomolgus skin cDNA. The cynoIL20R1 and cynoIL22R1 receptors were inserted into pcDNA3.1+(zeocin) and cynoIL20R2 was inserted into pcDNA3.1+(neomycin).

The following 5' and 3' primers were used for PCR-amplification of coding cDNA.

```
Human IL22R1:
                      (SEQ ID NOS: 29 and 30)
agaattccaccatgaggacgctgctgacca
and
gctcgagacagggaggaagcaccaag Human IL20R1:
                      (SEQ ID NOS: 31 and 32)
cgaattcccttggtttctggggaag
and
gctcgagcacaggaaacaaaaggcaaa Human IL20R2:
                      (SEQ ID NOS: 33 and 34)
agaattctggaaagaaacaatgttctaggtcaa
and
gctcgagcttcacctgggcccttcc Murine IL22R1:
                      (SEQ ID NOS: 35 and 36)
ccgaattcgccaccatgaagacactactgaccatc
and
cttgcggccgctcaggattcccactgcacagtc
```

-continued

```
Murine IL20R1:
                        (SEQ ID NOS: 37 and 38)
ttgaattcgccaccatgcacactcccggga
and
ttgcggccgcctagctttccatttgtacatgtaacc Murine IL20R2:
                        (SEQ ID NO: 39 and 30)
ttggatccgccaccatgatttcccagggagtctg
and
ttgcggccgctcaagtctgtgagatccagac Cynomolgus IL22R1:
                        (SEQ ID NO: 41 and 42)
agaattccaccatgaggacgctgctgacca
and
gctcgagacagggaggaagcaccaag Cynomolgus IL20R1:
                        (SEQ ID NOS: 43 and 44)
gtgggactgagcagtctgctg
and
aggcaaaaggaagtgttggca Cynomolgus IL20R2:
                        (SEQ ID NOS: 45 and 46)
agaattctggaaagaaacaatgttctaggtcaa
and
gctcgagcttcacctgggcccttcc
```

STAT-reporter KZ136 is a luciferase reporter containing STAT-elements and a Serum Response Element (SRE) (Poulsen-L K et al. J Biol Chem 1998; 273:6228-6232).

Luciferase Assay in Transient Transfection.

Day 0: BHK cells were seeded in T80 flask to a confluency of 40%. Day 1: 7.5 micrograms DNA was transfected using 36 microliters FuGene (Roche Applied Science) according to manufacturers manual, 2.5 micrograms of receptor chain 1 (IL20R1 or IL22R1) and 2.5 micrograms of chain 2 (IL20R2) and 2.5 mlcrograms of luciferase reporter (KZ136). Day 2: The cells were detached using Versene and 20,000 cells per well were seeded in a black view plate. After the cells have reattached the well surface the media was exchanged with serum-free media. Day 3: either 20 microliter of 10 mM IL20 or 20 microliter of serum-free medium was added to the wells. Four hours later the luciferase activity was determined; media was removed and 100 microliter 1xPBS was added to each well followed by the addition of 100 microliter Luclite substrate (PerkinElmer). The plate was incubated for 30 minutes. The luminescence was detected by a Topcount NXT (PerkinElmer). IL20 used here are either recombinantly produced hIL20 produced in E. coli, murine IL20 purchased from Biosource, #PMC0201, or cynomolgus IL20 produced by transient expression in HEK293 6E cells and purified.

Results

Neutralization of Murine IL20.

Figure 9:
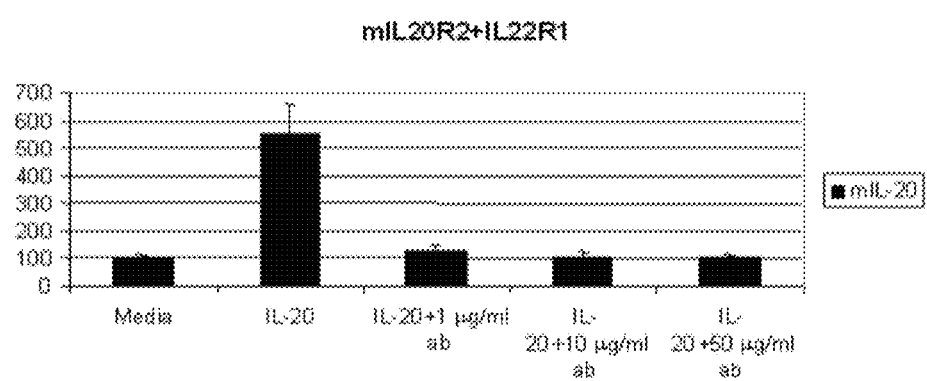
FIG. 9 shows 15D2 neutralization of murine IL20 activation of murine IL22R1/IL20R2 receptor, as revealed by a luciferase assay. Murine IL20 receptor complex mIL20R1/mIL22R1 was transfected into BHK cells and stimulated with 10 nM murine IL20. Neutralization of stimulation was investigated using 1 microgram/ml, 10 microgram/ml or 50 microgram/ml of 15D2.

The murine IL20 receptors were cloned and a transient luciferase reporter assay was set up in BHK cells. Both the two human receptor complexes and the two murine receptor complexes were stimulated with 1 nM murine IL20. Murine IL20 could activate both human and murine IL20R1/IL20R2 and IL22R1/IL20R2 receptor complexes. Neutralization by 15D2 was tested on one of the receptor complexes. The murine IL20R2/IL22R1 complex was transfected into BHK cells together with the STAT3 reporter construct. The receptor complex was stimulated with 1 nM murine IL20 and exposed to 15D2 antibody in 1, 10 and 50 microgram/ml doses (FIG. 9). The lowest dose, 1 microgram/ml, neutralized the effect almost totally.

Neutralization of Cynomolgus IL20.

Figure 10A:
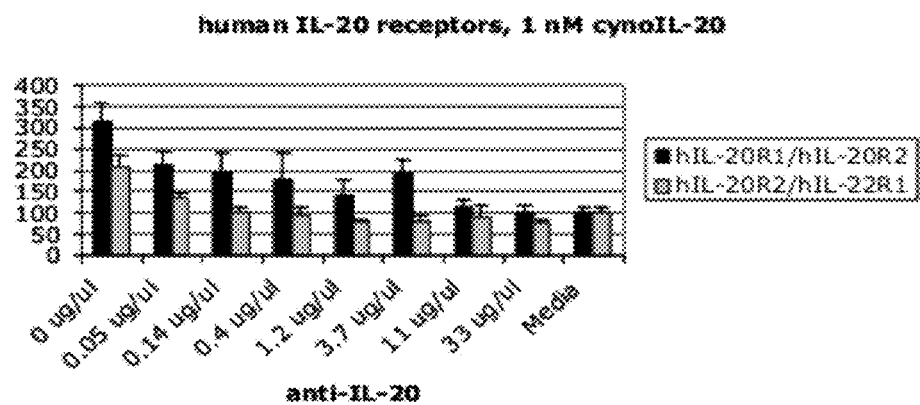
FIG. 10 shows 15D2 neutralization of cynomolgus IL20 activation of human IL20R1/IL20R2 and IL22R1/IL20R2 receptors (A) or cynomolgous IL20R1/IL20R2 and IL22R1/IL20R2 (B), as revealed by a luciferase assay.
Figure 10B:
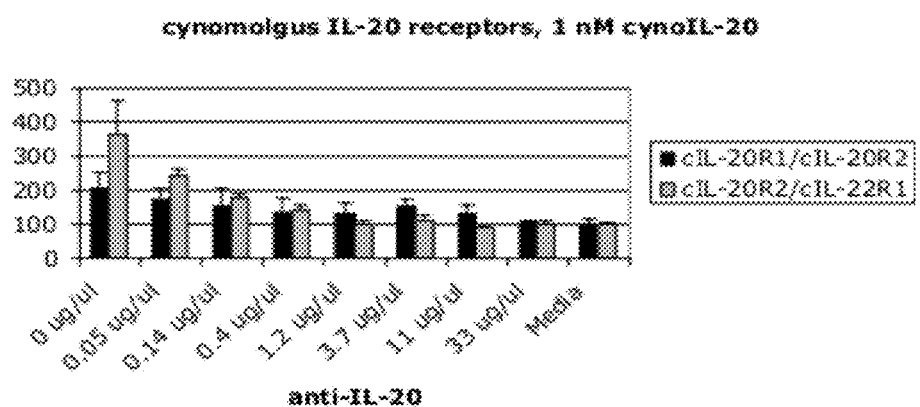

Cynomolgus IL20 receptor sequences IL20R1, IL20R2 and IL22R1 were cloned from cynomolgus skin tissue cDNA, using oligonucleotide primers based on human sequence. The respective sequence identities between cynomolgus and human receptor sequences were 96.8% for IL20R1, 98.9% for IL20R2, and 95.5% for IL22R1. BHK cells were transfected with the two receptor complexes, IL20R1/IL20R2 or IL22R1/IL20R2 together with the KZ136 (the STAT3 luciferase reporter) plasmid. The cynomolgus IL20R2/IL22R1 complex was induced 3-4 fold using 1 nM cynoIL20. The IL20R1/IL20R2 complex from cynomolgus was stimulated about 2-fold. Increasing the amount of 15D2 decreased the IL20 activity, showing that 15D2 could neutralize cynomolgous IL20 (FIG. 10).

Neutralization of hIL20.

Figure 11:
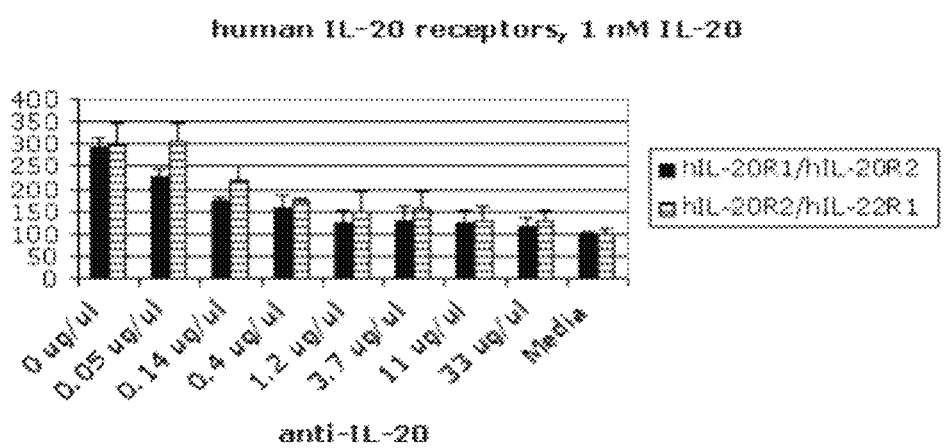
FIG. 11 shows 15D2 neutralization of human IL20-mediated activation of human IL20R1/IL20R2 and IL22R1/IL20R2, as revealed by a luciferase assay.

Human IL20 receptors IL20R1, IL20R2 and IL22R1, were cloned from NHEK (Normal Human Epidermal Keratinocyte) cDNA. Expression plasmids encoding the IL20 receptors were transiently transfected into BHK cells together with the luciferase reporter vector, KZ136. The stimulation was done using 1 nM hIL20 and an induction of about 3 fold was seen. Increasing the amount of 15D2 antibody decreased the IL20 activity (FIG. 11).

Example 10

Inhibition of hIL20-Induced Proliferation

This Example evaluates the inhibitory effects of 15D2 and rat anti-hIL20 mAbs on IL20-induced proliferation of BaF-3 cells expressing IL20R1 and IL20R2 (herein "hIL20R"), and the form of IL20 bound by 15D2.

Materials & Methods

Three independent experiments ("148", "149" and "150") compared EC50 values of the four tested abs. First, antibodies were added in a 3-fold serial dilution with 50 ul/well in media. At the same time 10 µl hIL20 was added to every well and at last 40 µl of cell-suspension. Antibodies were diluted to a 3-fold serial dilution (100+200), with the first dilution in the assay at 20 µg/ml. hIL20 preparation was diluted to $10^{-7}$M, with dilution in assay to $10^{-8}$M. As a control, the following stimulation curve was made: hIL20 was diluted to $10^{-6}$M and from this a 10-fold dilution row. First dilution in the assay was 10–7M.

BaF-3 cells recombinantly expressing human IL20R1/IL20R2 were centrifuged, resuspended in media without IL3, and counted. They were then washed twice in media without IL3, and added into 96-wells flat-bottomed view plates at a concentration of $10^4$ c/well and 40 µl. Dilution of cells: $10^4$ c/40 µl, $2.5 \times 10^6$ c/10 ml (enough for 2 plates). Incubation of plates for 3 days in a $CO_2$ incubator (5% $CO_2$, 37° C.). AlamarBlue 10 µl/w was added, and after 6 hours incubation plates were measured on a Polarstar fluorometer, exitation 550-12 nm and emission 590 nm.

In order to investigate whether 15D2 bound the soluble form of IL20 or the receptor-bound form of IL20, an experimental setup was designed where 15D2 was added in a 3-fold serial dilution. At the same time, 10 µl hIL20 was added to the wells and subsequently 40 µl of BaF3(hIL20R=hIL20R1 and hIL20R2) cell-suspension. Finally, hIL19 was added simultaneously (t=0) or after 1 minute (t=1).

Results

From the initial experiment testing proliferation as a function of concentration of hIL20 shown, it was chosen to measure the EC50 values of antibodies at 10 M hIL20.

Three independent experiments tested the inhibitory effects of antibodies on IL20 induced proliferation. EC50 values were calculated both with and without defined top and bottom. The latter gave the best correlation between the three independent experiments and was used for comparison of inhibitory effects (curves were fitted by "sigmoidal doseresponse with variable slope" in Prism). Table 4 below shows the EC50 values of the three experiments, comparing EC50 values for inhibition of IL20-induced proliferation of BaF-3 cells expressing IL20R1 and IL20R2.

TABLE 4

Inhibition of hIL20-induced proliferation of BaF-3 (hIL20R1/hIL20R2) cells

| Anti-IL20 ab | EC50 (nM) | | | |
|---|---|---|---|---|
| 15D2 | 6.5, 6.7, 6.8* | 6.6 | | 13.07 |
| 262.4.1.2.2.1 | 3.4 | 4.0 | | 2.77 |
| 262.5.1.6.4.4 | 17.0 | 25.6 | | 14.53 |
| 262.7.1.3.2.4 | 4.3 | 4.2 | | 4.16 |

*Included on three plates

Figure 12:
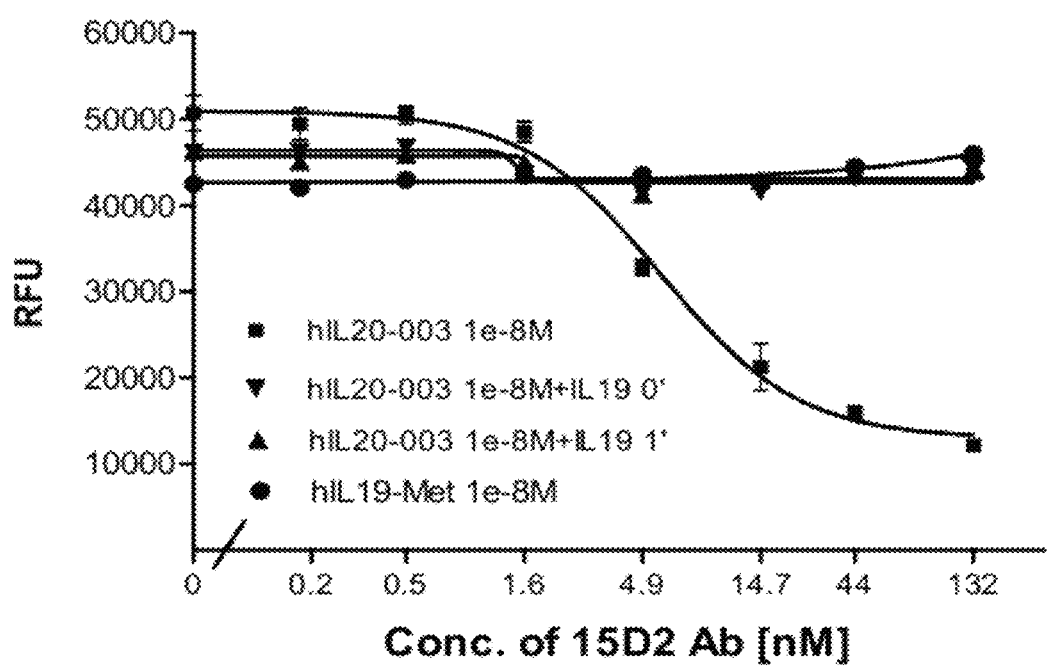
FIG. 12 shows that IL19 reverted the 15D2 blocking of IL20-induced proliferation, revealing that 15D2 bound the soluble form of IL20 and not the receptor-bound form, which would otherwise block access of IL19 to the receptor.

The EC50 values were analyzed by one-way ANOVA with Tukey post test. All of 15D2, 262.4.1.2.2.1 and 262.7.1.3.2.4 inhibited IL20 induced proliferation in IL20R transfected BaF-3 cells significantly better than 262.5.1.6.4.4. While the average EC50 values for 262.4.1.2.2.1 and 262.7.1.3.2.4 were lower than those of 15D2, the differences were not statistically significant (P<0.05). With respect to the assay investigating whether 15D2 bound the soluble or receptor-bound form of IL20, the results showed that addition of IL19 reverted the 15D2 blocking of IL20-induced proliferation (FIG. 12). This meant that 15D2 prevented binding of IL20 to the hIL20R, but that 15D2 did not prevent binding of IL19 to the receptor. Thus, 15D2 bound the soluble form of IL20 and not the receptor-bound form, which would otherwise block access of IL19 to the receptor.

Example 11

Neutralization of IL20 Activation of IL22R1/IL20R2

This example shows the inhibitory effect of human antibody 15D2 and rat anti-hIL20 mAbs on IL20-induced signalling via human IL22R1/IL20R2 receptor complex in a Luciferase reporter assay.

Materials and Methods

Generation a Human IL20 Reporter Cell Line.

The human IL20R2 in pcDNA3.1+(hygro) plasmid, IL22R1 in pcDNA3.1+(zeocin)plasmid and the STAT3 reporter plasmid KZ136 (neomycin) were transfected into BHK cells and selected by 200 ug/ml hygromycin, 400 ug/ml zeocin and 600 ug/ml geneticin. Clones were picked and the most IL20 responsive clone was selected, "BHK 1-B4". The BHK 1-B4 cell line responds approximately 10-fold in luciferase read-out to 10 nM IL20 compared to basal level (no stimulation).

Luciferase Assay in Stable BHK 1-B4 Cells.

The BHK 1-B4 were seeded in 96 well plates, 20,000 cells/well. Sixteen hours after seeding the cells were stimulated with 10 nM IL20 or mixtures with 10 nM IL20 and antibodies or plain media. The cells were stimulated for 4 hours, media was removed, 100 ul PBS (including Ca++ and Mg++) and 100 ul luciferase substrate (Steady-GLO) was added to the wells. The plate was incubated for 30 minutes. The luminescence was detected by a Topcount NXT (PerkinElmer).

Results

Neutralization of hIL20 by Anti-IL20 Antibodies.

The stable cell line BHK 1-B4 was generated by stably transfection of plasmids expressing IL20R2 and IL22R and the STAT3 Luciferase reporter plasmid, KZ136. Antibodies were mixed with IL20 prior to addition to the cells. The IL20 concentration was kept at 10 nM whereas the antibodies were added in range from 133 nM to 0.19 nM in 3-fold dilutions. Dose-response curves were obtained for the four antibodies, and EC50 values were calculated based on the curves fitted by "sigmoidal doseresponse with variable slope" in GraphPad Prism (Table 4). 15D2 neutralized signalling via hIL22R1/hIL20R2 as efficiently as 262.4.1.2.2.1 and better than 262.5.1.6.4.4 and 262.7.1.3.2.4.

TABLE 5

Neutralization of IL20 activation of IL22R1/IL20R2 receptor complex

| Anti-IL20 antibody | EC50 (nM) |
|---|---|
| 15D2 (NN) | 4.98 |
| 262.4.1.2.2.1 (ZGI) | 4.92 |
| 262.5.1.6.4.4 (ZGI) | 18.33 |
| 262.7.1.3.2.4 (ZGI) | 11.17 |

Example 12

Determination of Kinetic Parameters

Protein interactions can be monitored in real time using surface plasmon resonance (SPR) analyses. This Example describes SRP analysis on Biacore 3000 and Biacore T100 instruments, in order to characterize hybidoma-produced and/or recombinantly expressed human anti-IL20 antibodies 15D2 and 5B7 with respect to affinity towards recombinant hIL20.

Affinity studies were performed using a direct binding procedure, with the monoclonal antibody covalently coupled via free amine groups to the carboxymethylated dextrane membrane (CM5) on the sensor chip surface. Recombinant hIL20 was injected in various concentrations, followed by a dissociation period with constant buffer flow over the sensor chip surface. Using this experimental design, the binding of hIL20 to the immobilized monoclonal antibody could be regarded as a 1:1 binding, with one hIL20 molecule binding to one antibody binding site. The kinetic parameters for the interaction could be calculated using a 1:1 interaction Langmuir fitting model.

Materials & Methods 15D2 wild-type (wt) expressed by hybridoma cells, 15D2-wt expressed in HEK293 cells, 15D2 with an S241P mutation expressed in HEK293 cells, 15D2-S241P expressed in CHO cells, and 5B7-wt expressed by hybridoma cells, were analyzed. The purified monoclonal antibodies were immobilized in individual flow cells on a CM5 type sensor chip. Immobilizations were performed using a standard amine coupling procedure, aiming for an immobilization level of 1000 Resonance Units (RU). The antibodies were diluted to 5 µg/ml in 10 mM NaAc pH 5.0. HPS-EP pH 7.4 (10 mM HEPES, 150 mM NaCl, 3 mM EDTA and 0.005% Polysorbate P20) was used as running buffer, and diluent for the recombinant hIL20. Re combinant purified hIL20 was diluted to 100, 50, 25, 12.5, 6.25 and 3.125 nM. Association (injection) was 3 min., followed by a 30 min. dissociation (wash) period. Flow rate was 30 µl/min. Experiments were performed at 25° C. Regeneration of the surface following each cycle, was accomplished by injection of 30 sec. pulse of 10 mM Glycin-HCl pH 1.8, at a 30 μl/min flow rate. Detection in all flow cells simultaneously. Flow cell No. 1 contained no immobilized antibody, and was used for subtraction of background and bulk. The kinetic parameters were calculated by local fitting of the data for a given antibody-antigen combination using a 1:1 Langmuir binding model. Data was inspected for mass-transport limitations prior to calculation of the kinetic parameters. Experiments were performed on Biacore 3000 and T100 instruments. Data was evaluated using Biaeval 4.1 and Biacore T100 evaluation software.

Results.

The calculated affinities for the binding of recombinant hIL20 to the individual antibodies are listed in Table 6 below, showing rate constants and affinities of the individual anti-IL20 monoclonal antibodies. The affinities are listed in molar units (M), the on-rates in (1/Ms) and the off-rates in (1/s). The rate constants are listed in brackets below the affinity, as (onrate/off-rate).

The affinity determination, valid for the buffer used and with the recombinant form of the antigen, demonstrated KD values of both 15D2-wt HEK293 and 15D2-S241P CHO in the lower pM range. Furthermore, the affinities of the hybridoma expressed antibodies demonstrated affinities of about 0.5 nM KD of the 15D2-wt and 5B7-wt.

TABLE 6 kinetic parameters for 15D2 and 5B7 interactions with recombinant hIL20

| Antibody | KD (M) Hybridoma | KD (M) HEK293 | KD (M) CHO |
|---|---|---|---|
| 15D2-wt | 5.5E−10 (1.9E+05/1.1E−04) | 3.2E−11 (1.9E+06/6.3E−05) | — |
| 15D2-S241P | — | 3.6E−11 (1.7E+06/6.8E−05) | 3.1E−11 (2.3E+06/7.1E−05) |
| 5B7 | 7.5E−10 (1.4E+05/1.0E−04) | — | — |

Example 13

15D2 Binding Interface on IL20

This Example identifies the 15D2 binding interface on hIL20 using HX-MS technology. Unless otherwise indicated, the numbering of hIL20 amino acid residues in this Example refers to SEQ ID NO:1 with an N-terminal Met (M) residue (i.e., residue Y67 in this Example corresponds to residue Y66 in SEQ ID NO:1).

HXMS provides the possibility for mimicking in vivo conditions (see, e.g., Wales and Engen, Mass Spectrom. Rev. 25, 158 (2006), and Coales et al, Rapid Commun. Mass Spectrom. 23, 639 (2009)). The HX-MS technology used here provided information on which surface exposed amide hydrogens in IL20 became shielded from exchange with solvent upon 15D2 antibody binding, thereby facilitating a mapping of the binding interface. Furthermore, the methodology can also reveal more indirect structural effects in 1 L20. Here observed as a slight stabilization of the structure upon 15D2 binding as seen in some regions.

Amide hydrogen/deuterium exchange (HX) was initiated by a 23-fold dilution of IL20 in the presence or absence of 15D2 (Fab fragment) into the corresponding deuterated buffer (i.e. 25 mM MES, 80 mM NaCl, 96% $D_2O$, pH 6.4 (uncorrected value)). Non-deuterated controls were prepared by dilution into an identical protiated buffer. All HX reactions were carried out at 20° C. and contained 4 μM IL20 in the absence or presence of 5 μM 15D2. Preliminary data had demonstrated full saturation of IL20 binding at these protein concentrations.

At appropriate time intervals, aliquots of the HX reaction were quenched by an equal volume of ice-cold quenching buffer (1.35M Tris(2-carboxyethyl)phosphine hydrochloride, adjusted to pH 2.5 using NaOH) resulting in a final pH of 2.6 (uncorrected value). Quenched samples were immediately injected onto a cooled ultra high pressure liquid chromatography (UPLC)-mass spectrometry system (described in detail below) for pepsin digestion, rapid desalting and mass analysis.

All sample preparation, handling and injections were performed by a HD-x PAL auto-sampler (LEAP Technologies Inc.). The protein and quench solutions were held at 2° C. and deuterated buffer and labelling reactions were held at 20° C. A cooling box, temperature controlled at 1.5° C., contained the injection and switching valves, tubing, plumbing and columns. Pepsin column (Applied Biosystems), VanGuard C18 trapping column (Waters) and Acquity HPLC BEH C18 1.7 um, 2.1×100 mm analytical column (Waters Inc) were used. The LC flow was delivered from an Acquity UPLC pump using 0.1% Formic acid in H2O and 0.1% Formic acid in acetonitrile. A Q-ToF premier was used for mass analysis (Waters Inc).

Peptic peptides were identified in separate experiments using standard MS/MS methods. Average masses of peptide isotopic envelopes were determined from lockmasscorrected centroided data (processed using MassLynx software, Waters Inc.) using the software HXExpress (Weis et al., J. Am. Soc. Mass Spectrom. 17, 1700 (2006)).

Figure 14:
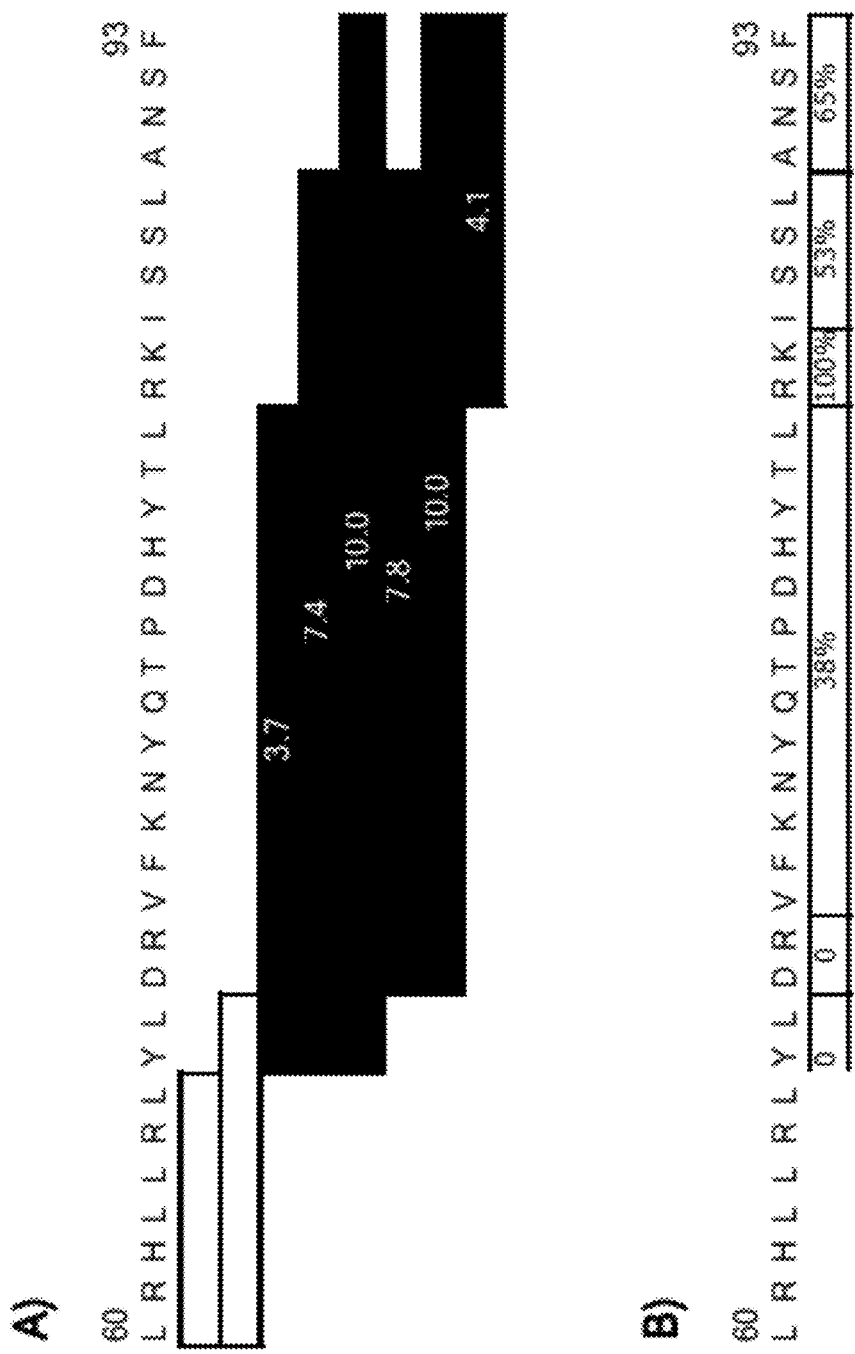
FIG. 14 shows sub-localization of the deuterium label from individual peptides in the HX-MS study. (A) Close-up of region 60-93 of the IL20 primary structure. Peptides showing similar exchange patterns both in the presence and absence of 15D2 are coloured grey whereas peptides showing reduced deuterium incorporation upon 15D2 binding are coloured black. The numbers indicate the difference in deuterium level observed in the individual IL20 regions upon 15D2 binding. (B) The information from the peptides have been sub-localized to smaller residue stretches by simple subtraction assuming complete off-exchange of the N-terminus and first peptide bond amide. The deuterium level was then corrected for the labelling reaction only containing 91% deuterium and reported as percent of total residues.

The HX time-course of 22 peptides, covering 93% of the primary sequence of IL20, were monitored in the presence and absence 15D2 (FIG. 13). The IL20 exchange pattern observed could be divided into two different groups. One group of peptides displayed an exchange pattern that was largely unaffected by the binding of 15D2. For example, Peptide 127-145 represented a region of IL20 that was unaffected by 15D2 binding. Some, however, showed a slight decrease in exchange at 30 sec due to slight stabilization of the protein structure upon 15D2 binding. For example, Peptides 17-38, 60-66 and 146-153 represented regions of IL20 that were outside the binding epitope but might show a slight structural stabilization upon 15D2 binding. In contrast, another group of peptides IL20 show strong protection, here more than 3 deuterons, from exchange upon 15D2 binding. Peptides 67-83, 67-93, 69-89, 69-93 and 84-93 represented peptides that were part of the binding epitope of 15D2. Thus, the region displaying protection upon 15D2 binding encompassed peptides from residues 67-93. For example at 30 sec exchange with $D_2O$, approximately 10 amides were protected from exchange in the region 69-93 upon 15D2 binding. The specific peptides and number of deuterons shielded from exchange upon 15D2 binding are depicted in FIG. 14 where the information gained after 30 sec exchange in $D_2O$ was sub-localized to few residues.

The 15D2 binding interface could thus be localized to residues 71-93, containing the sequence VFKNYQTP-DHYTLRKISSLANSF and corresponding to residues 70-92 of SEQ ID NO:1. The region containing residues 71-83, however, was protected to a lesser extent from deuterium exchange upon 15D2 binding. This indicates that the overall 15D2 binding in this region was less tight and, most likely, that only a fraction of these residues were involved in 15D2 binding. The residues 84-85 showed complete protection from exchange upon 15D2 binding and the region 86-93 was also highly affected by 15D2 binding, together corresponding to residues 83-92 of SEQ ID NO:1.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

EXEMPLARY EMBODIMENTS

The following are exemplary and non-limiting embodiments of the invention.

1. An isolated anti-human IL20 antibody or an antigen-binding fragment thereof, which reduces IL20 mediated activation of IL20R1/IL20R2 and IL22R1/IL20R2 receptor complexes.
2. The antibody or antigen-binding fragment of embodiment 1, which reduces human IL20 mediated activation of human IL20R1/IL20R2 and IL22R1/IL20R2 receptor complexes.
3. The antibody or antigen-binding fragment of any of the preceding embodiments, which reduces cynomolgus IL20 mediated activation of cynomolgus IL20R1/IL20R2 and IL22R1/IL20R2 receptor complexes.
4. The antibody or antigen-binding fragment of any of the preceding embodiments, which reduces murine IL20 mediated activation of murine IL20R1/IL20R2 and IL22R1/IL20R2 receptor complexes.
5. The antibody or antigen-binding fragment of any of the preceding embodiments, which reduces the binding of IL20 to the IL20R1/IL20R2 and/or IL22R1/IL20R2 receptor complexes.
6. The antibody or antigen-binding fragment of any of the preceding embodiments, which reduces the binding of IL20 to IL20R2.
7. The antibody or antigen-binding fragment of any of embodiments 1-4, which does not reduce binding of IL19 or IL24 to IL20R1/IL20R2 or IL22R1/IL20R2 receptor complexes.
8. The antibody or antigen-binding fragment of any of the preceding embodiments, which binds to an epitope comprising at least one residue selected from D78-H103 of mature human IL20 (SEQ ID NO:1), optionally excluding D78.
9. The antibody or antigen-binding fragment of embodiment 8, wherein the epitope comprises at least one residue selected from D78-K96.
10. The antibody or antigen-binding fragment of embodiment 9, wherein the epitope comprises at least one residue selected from D78-L93 or R83-F92.
11. The antibody or antigen-binding fragment of embodiment 10, wherein the epitope comprises at least one residue selected from H79-N90.
12. The antibody or antigen-binding fragment of embodiment 8, wherein the epitope comprises at least 3 residues selected from D78-H103.
13. The antibody or antigen-binding fragment of embodiment 12, wherein the epitope comprises at least 3 residues selected from D78-K96.
14. The antibody or antigen-binding fragment of embodiment 13, wherein the epitope comprises at least 3 residues selected from D78-L93 or R83-F92.
15. The antibody or antigen-binding fragment of embodiment 14, wherein the epitope comprises at least 3 residues selected from H79-N90.
16. The antibody or antigen-binding fragment of embodiment 8, wherein the epitope comprises at least 5 residues selected from D78-H103.
17. The antibody or antigen-binding fragment of embodiment 16, wherein the epitope comprises at least 5 residues selected from D78-K96 or R83-F92.
18. The antibody or antigen-binding fragment of embodiment 17, wherein the epitope comprises at least 5 residues selected from D78-L93.
19. The antibody or antigen-binding fragment of embodiment 18, wherein the epitope comprises at least 5 residues selected from H79-N90.

20. The antibody or antigen-binding fragment of embodiment 8, wherein the epitope is in the segment corresponding to residues D78-H103.
21. The antibody or antigen-binding fragment of embodiment 20, wherein the epitope is in the segment corresponding to residues D78-K96.
22. The antibody or antigen-binding fragment of embodiment 21, wherein the epitope is in the segment corresponding to residues D78-L93.
23. The antibody or antigen-binding fragment of embodiment 22, wherein the epitope is in the segment corresponding to residues D78-N90.
24. The antibody or antigen-binding fragment of embodiment 8, wherein the epitope comprises residues H79 and N90.
25. The antibody or antigen-binding fragment of embodiment 24, wherein the epitope further comprises residue R83.
26. The antibody or antigen-binding fragment of embodiment 25, further comprising one or more of S85, F91, and L92.
27. The antibody of any of the preceding embodiments, which is a human or humanized antibody.
28. The antibody or antigen-binding fragment of any of the preceding embodiments, comprising a heavy chain variable region that is the product of or derived from a set of human genes comprising VH1_03, D3-10, and JH6 genes.
29. The antibody or antigen-binding fragment of any of the preceding embodiments, comprising a light-chain variable region that is the product of or derived from a set of human genes comprising VKI_L18 and JK4 genes.
30. The antibody or antigen-binding fragment of any of the preceding embodiments, which is a full-length antibody.
31. The antibody of embodiment 30, which is a human antibody of the IgG1, IgG2, or IgG3 isotype.
32. The antibody of embodiment 30, which is of the IgG4 isotype.
33. The antibody of embodiment 32, which comprises an S241 P mutation.
34. An antibody derivative or multispecific antibody molecule comprising the antibody or antigen-binding fragment of any of embodiments 1-33.
35. An isolated anti-hIL20 antibody or an antigen-binding fragment thereof, comprising the heavy-chain variable regions CDR2 and CDR3 of SEQ ID NO:8.
36. The antibody or antigen-binding fragment of embodiment 35, comprising the heavy-chain variable region CDR1 of SEQ ID NO:8.
37. The antibody or antigen-binding fragment of embodiment 36, comprising a heavy-chain variable region comprising the sequence of SEQ ID NO:8.
38. The antibody or antigen-binding fragment of embodiment 35, comprising the heavy-chain variable region CDR2 and CDR3 of SEQ ID NO:6.
39. The antibody or antigen-binding fragment of embodiment 38, comprising the heavy-chain variable region CDR1 of SEQ ID NO:6.
40. The antibody or antigen-binding fragment of embodiment 39, comprising a heavy-chain variable region comprising the sequence of SEQ ID NO:6.
41. The antibody or antigen-binding fragment of embodiment 35, comprising the heavy-chain variable region CDR2 and CDR3 of SEQ ID NO:7.
42. The antibody or antigen-binding fragment of embodiment 41, comprising the heavy-chain variable region CDR1 of SEQ ID NO:7.
43. The antibody or antigen-binding fragment of embodiment 42, comprising a heavy-chain variable region comprising the sequence of SEQ ID NO:7.
44. The antibody or antigen-binding fragment of any of embodiments 35-43, comprising the light-chain variable region CDR1, CDR2 and CDR3 of SEQ ID NO:9.
45. The antibody or antigen-binding fragment of embodiment 44, comprising a light-chain variable region comprising the sequence of SEQ ID NO:9.
46. An isolated human anti-IL20 antibody which competes with an antibody comprising a VH region comprising SEQ ID NO:6 and/or 7 and a VL region comprising SEQ ID NO:9 in binding to mature human IL20 (SEQ ID NO:1).
47. The antibody of embodiment 46, which further competes with an antibody comprising a VH region comprising SEQ ID NO:6 and/or 7 and a VL region comprising SEQ ID NO:9 in binding to mIL20 (SEQ ID NO:4), cIL20 (SEQ ID NO:5), or both.
48. The antibody of embodiment 46, which binds to an epitope comprising at least one residue in the segment corresponding to residues D78-H103 of mature human IL20 (SEQ ID NO:1), optionally excluding D78.
49. The antibody of embodiment 48, which binds to an epitope comprising residue H79, R83, S85, N90, F91 and/or L92.
50. The antibody of embodiment 46, which binds to the same epitope as an antibody comprising a VH region comprising SEQ ID NO:6 and/or 7 and a VL region comprising SEQ ID NO:9 in hIL20 (SEQ ID NO:1).
51. An antigen-binding fragment of the antibody of any of embodiments 46-50.
52. A method of producing an anti-IL20 antibody or antigen-binding fragment, comprising culturing a host cell producing the antibody or antigen-binding fragment of any of the preceding embodiments under suitable conditions, and recovering said antibody or antigen-binding fragment.
53. A composition comprising the antibody or antigen-binding fragment of any of the preceding embodiments, and a pharmaceutically acceptable carrier.
54. The composition of embodiment 53, further comprising a second anti-inflammatory agent.
55. The composition of embodiment 54, wherein the second anti-inflammatory agent is selected from an immunosuppressant, an analgesic, an anti-angiogenic agent, a corticosteroid, a B-cell depletion agent, a B-cell antagonist, a T-cell antagonist, a complement-inhibiting agent, an anti-cytokine agent, and an anti-cytokine receptor agent, and combinations thereof.
56. A method for treating an inflammatory or autoimmune disorder, comprising administering an effective amount of an anti-IL20 antibody or an antigen-binding fragment thereof, which antibody or antigen-binding fragment reduces human IL20 mediated activation of human IL20R1/hIL20R2 and IL22R1/hIL20R2 receptor complexes.
57. The method of embodiment 56, comprising administering a second anti-inflammatory agent before, simultaneously with, or after administration of the composition comprising the antibody or antigen-binding fragment.
58. The method of embodiment 57, wherein the second anti-inflammatory agent is selected from an immunosuppressant, an analgesic, an anti-angiogenic agent, a corticosteroid, a B-cell depletion agent, a B-cell antagonist, a T-cell antagonist, a complement-inhibiting agent, an anti-cytokine agent, and an anti-cytokine receptor agent, and combinations thereof.
59. The method of embodiment 58, wherein the second anti-inflammatory agent is methotrexate.
60. The method of any of embodiments 56-59, wherein the inflammatory or autoimmune disorder is rheumatoid arthritis, juvenile rheumatoid arthritis, psoriasis, psoriatic arthritis, ankylosing spondylitis, Sjögren's syndrome, multiple sclerosis, inflammatory bowel disease, systemic lupus erythematosus, lupus nephritis, or a combination of any thereof.
61. The method of embodiment 60, wherein the inflammatory or autoimmune disorder is rheumatoid arthritis.
62. The method of embodiment 60, wherein the inflammatory or autoimmune disorder is psoriasis.
63. The method of embodiment 60, wherein the inflammatory or autoimmune disorder is psoriatic arthritis.
64. The method of embodiment 60, wherein the inflammatory or autoimmune disorder is multiple sclerosis.
65. The method of embodiment 60, wherein the inflammatory or autoimmune disorder is inflammatory bowel disease.
66. The method of embodiment 60, wherein the inflammatory or autoimmune disorder is systemic lupus erythematosus.
67. The method of embodiment 60, wherein the inflammatory or autoimmune disorder is lupus nephritis.
68. The antibody or antigen-binding fragment of any of embodiments 1-51 for use in treating an inflammatory or autoimmune disorder.
69. A combination of the antibody or antigen-binding fragment of any of embodiments 1-51 with a second anti-inflammatory agent for use in treating an inflammatory or autoimmune disorder.
70. The combination of embodiment 69, wherein the second anti-inflammatory agent is administered before, simultaneously with, or after the antibody or antigen-binding fragment.
71. The combination of embodiment 70, wherein the second anti-inflammatory agent is methotrexate.
72. The use of the antibody or antigen-binding fragment of any of embodiments 1-51 in the preparation of a medicament for treating an inflammatory or autoimmune disorder.
73. The antibody or antigen-binding fragment, combination, or use of any of embodiments 68-72, wherein the inflammatory or autoimmune disorder is rheumatoid arthritis.
74. The antibody or antigen-binding fragment, combination, or use of any of embodiments 68-72, wherein the inflammatory or autoimmune disorder is psoriasis.
75. The antibody or antigen-binding fragment, combination, or use of any of embodiments 68-72, wherein the inflammatory or autoimmune disorder is psoriatic arthritis.
76. The antibody or antigen-binding fragment, combination, or use of any of embodiments 68-72, wherein the inflammatory or autoimmune disorder is multiple sclerosis.
77. The antibody or antigen-binding fragment, combination, or use of any of embodiments 68-72, wherein the inflammatory or autoimmune disorder is inflammatory bowel disease.
78. The antibody or antigen-binding fragment, combination, or use of any of embodiments 68-72, wherein the inflammatory or autoimmune disorder is systemic lupus erythematosus.
79. The antibody or antigen-binding fragment, combination, or use of any of embodiments 68-72, wherein the inflammatory or autoimmune disorder is lupus nephritis.
80. The antibody or antigen-binding fragment, combination, or use of any of embodiments 68-72, wherein the inflammatory or autoimmune disorder is juvenile rheumatoid arthritis.
81. The antibody or antigen-binding fragment, combination, or use of any of embodiments 68-72, wherein the inflammatory or autoimmune disorder is ankylosing spondylitis.
82. The antibody or antigen-binding fragment, combination, or use of any of embodiments 68-72, wherein the inflammatory or autoimmune disorder is Sjögren's syndrome.

The invention claimed is:

1. An isolated anti-human IL20 antibody or an antigen-binding fragment thereof comprising: a heavy chain variable region comprising a CDR1 sequence, a CDR2 sequence, and a CDR3 sequence as set forth in SEQ ID NO:6; and a light chain variable region comprising a CDR1 sequence, a CDR2 sequence, and a CDR3 sequence as set forth in SEQ ID NO:9.

2. The antibody or antigen-binding fragment of claim 1, wherein the CDR1, CDR2, and CDR3 sequences of the heavy chain variable region correspond to Kabat residues 31-35, 50-65, and 95-102 of SEQ ID NO:6, and wherein the CDR1, CDR2, and CDR3 sequences of the light chain variable region correspond to Kabat residues 24-34, 50-56, and 89-97 of SEQ ID NO:9.

3. The antibody or antigen-binding fragment of claim 1, wherein the light chain variable region comprises SEQ ID NO:9 and the heavy-chain variable sequence comprises SEQ ID NO:6.

4. An isolated anti-human IL20 antibody or an antigen-binding fragment thereof comprising a heavy chain variable region comprising the light chain variable sequence of SEQ ID NO:9 and the heavy-chain variable sequence of SEQ ID NO:6 or SEQ ID NO:7.

5. The antibody of claim 1, which is of the IgG4 isotype.

6. A pharmaceutical composition comprising at least about 80 mg/ml of the antibody of claim 1, and a pharmaceutically acceptable excipient, diluent, or carrier.

7. The antibody of claim 3, which is of the IgG4 isotype.

8. A pharmaceutical composition comprising at least about 80 mg/ml of the antibody of claim 3, and a pharmaceutically acceptable excipient, diluent, or carrier.

9. The antibody of claim 4, which is of the IgG4 isotype.

10. A pharmaceutical composition comprising at least about 80 mg/ml of the antibody of claim 4, and a pharmaceutically acceptable excipient, diluent, or carrier.

* * * * *

SEQUENCE LISTING

```
<160> NUMBER OF SEQ ID NOS: 46

<210> SEQ ID NO 1
<211> LENGTH: 152
<212> TYPE: PRT
<213> ORGANISM: Homo sapiens

<400> SEQUENCE: 1

Leu Lys Thr Leu Asn Leu Gly Ser Cys Val Ile Ala Thr Asn Leu Gln
1               5                   10                  15

Glu Ile Arg Asn Gly Phe Ser Glu Ile Arg Gly Ser Val Gln Ala Lys
            20                  25                  30

Asp Gly Asn Ile Asp Ile Arg Ile Leu Arg Arg Thr Glu Ser Leu Gln
        35                  40                  45

Asp Thr Lys Pro Ala Asn Arg Cys Cys Leu Leu Arg His Leu Leu Arg
    50                  55                  60

Leu Tyr Leu Asp Arg Val Phe Lys Asn Tyr Gln Thr Pro Asp His Tyr
```

```
                65                  70                  75                  80
Thr Leu Arg Lys Ile Ser Ser Leu Ala Asn Ser Phe Leu Thr Ile Lys
                85                  90                  95

Lys Asp Leu Arg Leu Cys His Ala His Met Thr Cys His Cys Gly Glu
            100                 105                 110

Glu Ala Met Lys Lys Tyr Ser Gln Ile Leu Ser His Phe Glu Lys Leu
        115                 120                 125

Glu Pro Gln Ala Ala Val Val Lys Ala Leu Gly Glu Leu Asp Ile Leu
    130                 135                 140

Leu Gln Trp Met Glu Glu Thr Glu
145                 150

<210> SEQ ID NO 2
<211> LENGTH: 176
<212> TYPE: PRT
<213> ORGANISM: Homo sapiens

<400> SEQUENCE: 2

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Glu
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175

<210> SEQ ID NO 3
<211> LENGTH: 177
<212> TYPE: PRT
<213> ORGANISM: Homo sapiens

<400> SEQUENCE: 3

Met Lys Leu Gln Cys Val Ser Leu Trp Leu Leu Gly Thr Ile Leu Ile
1               5                   10                  15

Leu Cys Ser Val Asp Asn His Gly Leu Arg Arg Cys Leu Ile Ser Thr
            20                  25                  30

Asp Met His His Ile Glu Glu Ser Phe Gln Glu Ile Lys Arg Ala Ile
        35                  40                  45

Gln Ala Lys Asp Thr Phe Pro Asn Val Thr Ile Leu Ser Thr Leu Glu
    50                  55                  60

Thr Leu Gln Ile Ile Lys Pro Leu Asp Val Cys Cys Val Thr Lys Asn
65                  70                  75                  80
```

```
Leu Leu Ala Phe Tyr Val Asp Arg Val Phe Lys Asp His Gln Glu Pro
                85                  90                  95

Asn Pro Lys Ile Leu Arg Lys Ile Ser Ser Ile Ala Asn Ser Phe Leu
            100                 105                 110

Tyr Met Gln Lys Thr Leu Arg Gln Cys Gln Glu Gln Arg Gln Cys His
        115                 120                 125

Cys Arg Gln Glu Ala Thr Asn Ala Thr Arg Val Ile His Asp Asn Tyr
    130                 135                 140

Asp Gln Leu Glu Val His Ala Ala Ile Lys Ser Leu Gly Glu Leu
145                 150                 155                 160

Asp Val Phe Leu Ala Trp Ile Asn Lys Asn His Glu Val Met Phe Ser
                165                 170                 175

Ala

<210> SEQ ID NO 4
<211> LENGTH: 176
<212> TYPE: PRT
<213> ORGANISM: Mus musculus

<400> SEQUENCE: 4

Met Lys Gly Phe Gly Leu Ala Phe Gly Leu Phe Ser Ala Val Gly Phe
1               5                   10                  15

Leu Leu Trp Thr Pro Leu Thr Gly Leu Lys Thr Leu His Leu Gly Ser
                20                  25                  30

Cys Val Ile Thr Ala Asn Leu Gln Ala Ile Gln Lys Glu Phe Ser Glu
            35                  40                  45

Ile Arg Asp Ser Val Gln Ala Glu Asp Thr Asn Ile Asp Ile Arg Ile
        50                  55                  60

Leu Arg Thr Thr Glu Ser Leu Lys Asp Ile Lys Ser Leu Asp Arg Cys
65                  70                  75                  80

Cys Phe Leu Arg His Leu Val Arg Phe Tyr Leu Asp Arg Val Phe Lys
                85                  90                  95

Val Tyr Gln Thr Pro Asp His His Thr Leu Arg Lys Ile Ser Ser Leu
            100                 105                 110

Ala Asn Ser Phe Leu Ile Ile Lys Lys Asp Leu Ser Val Cys His Ser
        115                 120                 125

His Met Ala Cys His Cys Gly Glu Glu Ala Met Glu Lys Tyr Asn Gln
    130                 135                 140

Ile Leu Ser His Phe Ile Glu Leu Glu Leu Gln Ala Ala Val Val Lys
145                 150                 155                 160

Ala Leu Gly Glu Leu Gly Ile Leu Leu Arg Trp Met Glu Glu Met Leu
                165                 170                 175

<210> SEQ ID NO 5
<211> LENGTH: 176
<212> TYPE: PRT
<213> ORGANISM: Macaca fascicularis

<400> SEQUENCE: 5

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
                20                  25                  30

Cys Val Ile Ala Thr Asn Leu Gln Glu Ile Arg Asn Gly Phe Ser Glu
            35                  40                  45

Ile Arg Gly Ser Val Gln Ala Lys Asp Gly Asn Ile Asp Ile Arg Ile
```

```
                   50                  55                  60
Leu Arg Arg Thr Glu Ser Leu Gln Asp Thr Lys Pro Ala Asp Gln Cys
 65                  70                  75                  80

Cys Leu Leu Arg His Leu Leu Arg Leu Tyr Leu Asp Arg Val Phe Lys
                     85                  90                  95

Asn Tyr Gln Thr Leu Asp His Tyr Thr Leu Arg Lys Ile Ser Ser Leu
                    100                 105                 110

Ala Asn Ser Phe Leu Thr Ile Lys Lys Asp Leu Arg Leu Cys His Ala
                    115                 120                 125

His Met Thr Cys His Cys Gly Glu Glu Ala Met Lys Lys Tyr Gly Gln
                    130                 135                 140

Ile Leu Ser His Phe Glu Glu Leu Glu Pro Gln Ala Ala Val Val Lys
145                 150                 155                 160

Ala Leu Gly Glu Leu Asp Ile Leu Leu Gln Trp Met Glu Glu Thr Glu
                    165                 170                 175

<210> SEQ ID NO 6
<211> LENGTH: 127
<212> TYPE: PRT
<213> ORGANISM: Homo sapiens

<400> SEQUENCE: 6

Gln Val Gln Leu Val Gln Ser Gly Ala Glu Val Lys Arg Pro Gly Ala
 1               5                  10                  15

Ser Val Lys Val Ser Cys Lys Ala Ser Gly Tyr Thr Phe Thr Asn Asp
                 20                  25                  30

Ile Ile His Trp Val Arg Gln Ala Pro Gly Gln Arg Leu Glu Trp Met
             35                  40                  45

Gly Trp Ile Asn Ala Gly Tyr Gly Asn Thr Gln Tyr Ser Gln Asn Phe
 50                  55                  60

Gln Asp Arg Val Ser Ile Thr Arg Asp Thr Ser Ala Ser Thr Ala Tyr
 65                  70                  75                  80

Met Glu Leu Ile Ser Leu Arg Ser Glu Asp Thr Ala Val Tyr Tyr Cys
                 85                  90                  95

Ala Arg Glu Pro Leu Trp Phe Gly Glu Ser Ser Pro His Asp Tyr Tyr
                100                 105                 110

Gly Met Asp Val Trp Gly Gln Gly Thr Thr Val Thr Val Ser Ser
                115                 120                 125

<210> SEQ ID NO 7
<211> LENGTH: 127
<212> TYPE: PRT
<213> ORGANISM: Homo sapiens

<400> SEQUENCE: 7

Gln Val Gln Leu Val Gln Ser Gly Ala Glu Val Lys Arg Pro Gly Ala
 1               5                  10                  15

Ser Val Lys Val Ser Cys Lys Ala Ser Gly Tyr Thr Phe Ser Ser His
                 20                  25                  30

Ile Met His Trp Val Arg Gln Ala Pro Gly Gln Arg Leu Glu Trp Met
             35                  40                  45

Gly Trp Ile Asn Ala Gly Tyr Gly Asn Thr Lys Tyr Ser Gln Asn Phe
 50                  55                  60

Gln Asp Arg Val Thr Ile Thr Arg Asp Thr Ser Ala Ser Thr Ala Tyr
 65                  70                  75                  80

Met Glu Leu Ile Ser Leu Arg Ser Glu Asp Thr Ala Val Tyr Tyr Cys
                 85                  90                  95
```

Ala Arg Glu Pro Leu Trp Phe Gly Glu Leu Ser Pro His Asp Tyr Tyr
            100                 105                 110

Gly Met Asp Val Trp Gly Gln Gly Thr Thr Val Thr Val Ser Ser
            115                 120                 125

<210> SEQ ID NO 8
<211> LENGTH: 127
<212> TYPE: PRT
<213> ORGANISM: Homo sapiens
<220> FEATURE:
<221> NAME/KEY: MISC_FEATURE
<222> LOCATION: (30)..(30)
<223> OTHER INFORMATION: X1 is T, S, or a conservative substitution of
      any thereof
<220> FEATURE:
<221> NAME/KEY: MISC_FEATURE
<222> LOCATION: (31)..(31)
<223> OTHER INFORMATION: X2 is N, S, or a conservative substitution of
      any thereof
<220> FEATURE:
<221> NAME/KEY: MISC_FEATURE
<222> LOCATION: (32)..(32)
<223> OTHER INFORMATION: X3 is D, H, or a conservative substitution of
      any thereof
<220> FEATURE:
<221> NAME/KEY: MISC_FEATURE
<222> LOCATION: (34)..(34)
<223> OTHER INFORMATION: X4 is I, M, or a conservative substitution of
      any thereof
<220> FEATURE:
<221> NAME/KEY: MISC_FEATURE
<222> LOCATION: (59)..(59)
<223> OTHER INFORMATION: X5 is K, Q, or a conservative substitution of
      any thereof
<220> FEATURE:
<221> NAME/KEY: MISC_FEATURE
<222> LOCATION: (69)..(69)
<223> OTHER INFORMATION: X6 is S, T, or a conservative substitution of
      any thereof
<220> FEATURE:
<221> NAME/KEY: MISC_FEATURE
<222> LOCATION: (106)..(106)
<223> OTHER INFORMATION: X7 is S, L, or a conservative substitution of
      any thereof

<400> SEQUENCE: 8

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Xaa Xaa Xaa
            20                  25                  30

Ile Xaa His Trp Val Arg Gln Ala Pro Gly Gln Arg Leu Glu Trp Met
        35                  40                  45

Gly Trp Ile Asn Ala Gly Tyr Gly Asn Thr Xaa Tyr Ser Gln Asn Phe
    50                  55                  60

Gln Asp Arg Val Xaa Ile Thr Arg Asp Thr Ser Ala Ser Thr Ala Tyr
65                  70                  75                  80

Met Glu Leu Ile Ser Leu Arg Ser Glu Asp Thr Ala Val Tyr Tyr Cys
                85                  90                  95

Ala Arg Glu Pro Leu Trp Phe Gly Glu Xaa Ser Pro His Asp Tyr Tyr
            100                 105                 110

Gly Met Asp Val Trp Gly Gln Gly Thr Thr Val Thr Val Ser Ser
            115                 120                 125

<210> SEQ ID NO 9
<211> LENGTH: 108
<212> TYPE: PRT
<213> ORGANISM: Homo sapiens

<400> SEQUENCE: 9

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg
            100                 105

<210> SEQ ID NO 10
<211> LENGTH: 98
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 11
<211> LENGTH: 31
<212> TYPE: DNA
<213> ORGANISM: Homo sapiens

<400> SEQUENCE: 11
gtattactat ggttcgggga gttattataa c                                    31

<210> SEQ ID NO 12
<211> LENGTH: 9
<212> TYPE: PRT
<213> ORGANISM: Homo sapiens

<400> SEQUENCE: 12

Val Leu Leu Trp Phe Gly Glu Leu Leu
1               5

<210> SEQ ID NO 13
<211> LENGTH: 63
<212> TYPE: DNA
<213> ORGANISM: Homo sapiens

<400> SEQUENCE: 13

```
attactacta ctactacggt atggacgtct gggggcaagg gaccacggtc accgtctcct    60
cag                                                                  63
```

<210> SEQ ID NO 14
<211> LENGTH: 20
<212> TYPE: PRT
<213> ORGANISM: Homo sapiens

<400> SEQUENCE: 14

Tyr Tyr Tyr Tyr Tyr Gly Met Asp Val Trp Gly Gln Gly Thr Thr Val
1               5                   10                  15

Thr Val Ser Ser
        20

<210> SEQ ID NO 15
<211> LENGTH: 95
<212> TYPE: PRT
<213> ORGANISM: Homo sapiens

<400> SEQUENCE: 15

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 16
<211> LENGTH: 38
<212> TYPE: DNA
<213> ORGANISM: Homo sapiens

<400> SEQUENCE: 16
gctcactttc ggcggaggga ccaaggtgga gatcaaac                            38

<210> SEQ ID NO 17
<211> LENGTH: 12
<212> TYPE: PRT
<213> ORGANISM: Homo sapiens

<400> SEQUENCE: 17

Leu Thr Phe Gly Gly Gly Thr Lys Val Glu Ile Lys
1               5                   10

<210> SEQ ID NO 18
<211> LENGTH: 123
<212> TYPE: PRT
<213> ORGANISM: homo sapiens

<400> SEQUENCE: 18

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Phe Ser Thr Asn
            20                  25                  30

Gly Val Gly Val Gly Trp Ile Arg Gln Pro Pro Gly Lys Ala Leu Glu

```
                35                  40                  45
Trp Leu Ala Leu Ile Tyr Trp Asn Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Leu Asp Thr Ala Thr Tyr Tyr
                 85                  90                  95

Cys Ala His Ser Pro Phe Ile Met Val Arg Gly Val Ile Ile Thr Phe
                100                 105                 110

Phe Asp Phe Trp Gly Gln Gly Thr Leu Val Thr
            115                 120

<210> SEQ ID NO 19
<211> LENGTH: 109
<212> TYPE: PRT
<213> ORGANISM: Homo sapiens

<400> SEQUENCE: 19

Val Ile Trp Met Thr Gln Ser Pro Ser Leu Ser Ala Ser Thr Gly
  1               5                  10                  15

Asp Arg Val Thr Ile Ser Cys Arg Met Ser Gln Gly Ile Ser Ser Tyr
                 20                  25                  30

Leu Ala Trp Tyr Gln Gln Lys Pro Gly Lys Ala Pro Glu Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Tyr Ser Phe Pro Leu
                 85                  90                  95

Thr Phe Gly Gly Gly Thr Lys Val Glu Ile Lys Arg Thr
            100                 105

<210> SEQ ID NO 20
<211> LENGTH: 123
<212> TYPE: PRT
<213> ORGANISM: Homo sapiens

<400> SEQUENCE: 20

Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Asn
                 20                  25                  30

Asn Tyr Tyr Trp Ala Trp Ile Arg Gln Pro Pro Gly Lys Gly Pro Glu
             35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Ala Ala Val Tyr Phe
                 85                  90                  95

Cys Ala Gly Leu Val Val Ile Pro Ala Ser Asp Tyr Tyr Tyr Gly
            100                 105                 110

Met Asp Val Trp Gly Gln Gly Thr Ser Val Thr
            115                 120

<210> SEQ ID NO 21
```

```
<211> LENGTH: 110
<212> TYPE: PRT
<213> ORGANISM: Homo sapiens

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys Arg Thr
            100                 105                 110

<210> SEQ ID NO 22
<211> LENGTH: 122
<212> TYPE: PRT
<213> ORGANISM: Homo sapiens

<400> SEQUENCE: 22

Gln Val Gln Val Val Gln Ser Gly Ala Glu Val Lys Lys Pro Gly Ala
1               5                   10                  15

Ser Val Arg Val Ser Cys Thr Ala Ser Gly Tyr Thr Phe Thr Asp Tyr
            20                  25                  30

Ala Ile His Trp Val Arg Gln Ala Pro Gly Gln Arg Leu Glu Trp Met
        35                  40                  45

Gly Trp Ile Asn Ala Gly Tyr Gly Asn Thr Lys Tyr Ser Gln Lys Phe
    50                  55                  60

Gln Gly Arg Val Thr Ile Thr Arg Asp Thr Ser Ala Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Ala Leu Ser Trp Phe Gly Glu Ser Gln Gly Phe
            100                 105                 110

Asp Tyr Trp Gly Gln Gly Thr Leu Val Thr
        115                 120

<210> SEQ ID NO 23
<211> LENGTH: 122
<212> TYPE: PRT
<213> ORGANISM: Homo sapiens

<400> SEQUENCE: 23

Gln Val Gln Leu Val Gln Ser Gly Ala Glu Val Lys Lys Pro Gly Ala
1               5                   10                  15

Ser Val Arg Val Ser Cys Thr Ala Ser Gly Tyr Thr Phe Pro Asn Tyr
            20                  25                  30

Ala Ile His Trp Val Arg Gln Ala Pro Gly Gln Arg Leu Glu Trp Met
        35                  40                  45

Gly Trp Ile Asn Ala Gly Tyr Gly Asn Thr Lys Tyr Ser Gln Lys Phe
    50                  55                  60

Gln Gly Arg Val Thr Ile Thr Arg Asp Thr Ser Ala Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Glu Gly Gly Val Leu Leu Trp Phe Gly Glu Ser Gln Gly Phe
                100                 105                 110

Asp Tyr Trp Gly Gln Gly Thr Leu Val Thr
                115                 120

<210> SEQ ID NO 24
<211> LENGTH: 108
<212> TYPE: PRT
<213> ORGANISM: Homo sapiens

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Gly Gln Gly Thr Lys Val Glu Ile Lys Arg Thr
                100                 105

<210> SEQ ID NO 25
<211> LENGTH: 476
<212> TYPE: PRT
<213> ORGANISM: Homo sapiens

<400> SEQUENCE: 25

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Arg
                20                  25                  30

Pro Gly Ala Ser Val Lys Val Ser Cys Lys Ala Ser Gly Tyr Thr Phe
            35                  40                  45

Thr Asn Asp Ile Ile His Trp Val Arg Gln Ala Pro Gly Gln Arg Leu
        50                  55                  60

Glu Trp Met Gly Trp Ile Asn Ala Gly Tyr Gly Asn Thr Gln Tyr Ser
65                  70                  75                  80

Gln Asn Phe Gln Asp Arg Val Ser Ile Thr Arg Asp Thr Ser Ala Ser
                85                  90                  95

Thr Ala Tyr Met Glu Leu Ile Ser Leu Arg Ser Glu Asp Thr Ala Val
                100                 105                 110

Tyr Tyr Cys Ala Arg Glu Pro Leu Trp Phe Gly Glu Ser Ser Pro His
            115                 120                 125

Asp Tyr Tyr Gly Met Asp Val Trp Gly Gln Gly Thr Thr Val Thr Val
        130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175
```

```
Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Leu Gly Thr
210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
            245                 250                 255

Pro Cys Pro Ala Pro Glu Leu Leu Gly Gly Pro Ser Val Phe Leu Phe
        260                 265                 270

Pro Pro Lys Pro Lys Asp Thr Leu Met Ile Ser Arg Thr Pro Glu Val
    275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
            325                 330                 335

Val Leu His Gln Asp Trp Leu Asn Gly Lys Glu Tyr Lys Cys Lys Val
        340                 345                 350

Ser Asn Lys Ala Leu Pro Ala Pro Ile Glu Lys Thr Ile Ser Lys Ala
    355                 360                 365

Lys Gly Gln Pro Arg Glu Pro Gln Val Tyr Thr Leu Pro Pro Ser Arg
370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
        420                 425                 430

Phe Phe Leu Tyr Ser Lys Leu Thr Val Asp Lys Ser Arg Trp Gln Gln
    435                 440                 445

Gly Asn Val Phe Ser Cys Ser Val Met His Glu Ala Leu His Asn His
450                 455                 460

Tyr Thr Gln Lys Ser Leu Ser Leu Ser Pro Gly Lys
465                 470                 475

<210> SEQ ID NO 26
<211> LENGTH: 552
<212> TYPE: PRT
<213> ORGANISM: Macaca fascicularis

<400> SEQUENCE: 26

Met Arg Ala Pro Ser Ser Pro Ala Leu Arg Pro Leu Leu Pro Pro Leu
1               5                   10                  15

Leu Leu Leu Leu Leu Ala Ala Pro Trp Gly Leu Ala Val Pro Cys Val
            20                  25                  30

Ser Gly Gly Leu Pro Lys Pro Ala Asn Ile Thr Phe Leu Ser Ile Asn
        35                  40                  45

Met Lys Asn Val Leu Gln Trp Asn Pro Pro Glu Cys Leu Gln Gly Val
    50                  55                  60

Lys Val Thr Tyr Thr Val Gln Tyr Phe Ile Tyr Gly Gln Lys Lys Trp
65                  70                  75                  80
```

-continued

```
Leu Asn Lys Ser Glu Cys Arg Asn Ile Asn Arg Thr Tyr Cys Asp Leu
                85                  90                  95
Ser Ala Glu Thr Ser Asp Tyr Glu His Gln Tyr Tyr Ala Lys Val Lys
            100                 105                 110
Ala Ile Trp Gly Thr Asn Cys Ser Lys Trp Ala Glu Ser Gly Arg Phe
        115                 120                 125
Tyr Pro Phe Leu Glu Thr Gln Ile Gly Pro Pro Glu Val Ala Leu Thr
    130                 135                 140
Thr Asp Glu Lys Ser Ile Ser Val Val Leu Thr Ala Pro Glu Lys Trp
145                 150                 155                 160
Lys Arg Asn Pro Glu Asp Leu Pro Val Ser Met Arg Gln Ile Tyr Ser
                165                 170                 175
Asn Leu Lys Tyr Asn Val Ser Val Ser Asn Thr Lys Ser Asn Arg Thr
            180                 185                 190
Trp Ser Gln Cys Val Thr Asn His Thr Leu Val Leu Thr Trp Leu Glu
        195                 200                 205
Pro Asn Thr Leu Tyr Cys Ile His Val Glu Ser Phe Val Pro Gly Pro
    210                 215                 220
Pro Arg Arg Ala Gln Pro Ser Glu Lys Gln Cys Ala Arg Thr Leu Lys
225                 230                 235                 240
Asp Gln Ser Ser Glu Phe Lys Ala Lys Ile Ile Phe Trp Tyr Val Leu
                245                 250                 255
Pro Val Ser Val Thr Val Phe Leu Phe Ser Val Met Gly Tyr Ser Ile
            260                 265                 270
Tyr Arg Tyr Ile His Val Gly Lys Glu Lys His Pro Ala Asn Leu Ile
        275                 280                 285
Leu Ile Tyr Gly Asn Glu Phe Asp Lys Arg Phe Phe Val Pro Ala Glu
    290                 295                 300
Lys Ile Val Ile Asn Phe Ile Thr Leu Asn Ile Ser Asp Asp Ser Lys
305                 310                 315                 320
Ile Ser His Gln Asp Met Ser Leu Leu Gly Lys Ser Ser Asp Val Ser
                325                 330                 335
Ser Leu Asn Asp Pro Gln Pro Ser Gly Asn Leu Lys Pro Pro Gln Glu
            340                 345                 350
Glu Glu Glu Val Lys His Leu Gly Tyr Ala Ser His Leu Met Glu Ile
        355                 360                 365
Val Cys Asp Ser Glu Glu Asn Ala Glu Gly Thr Ser Leu Thr Gln Gln
    370                 375                 380
Ala Ser Leu Ser Arg Thr Ile Pro Pro Asp Lys Thr Val Ile Glu Tyr
385                 390                 395                 400
Glu Cys Asp Val Arg Thr Thr Asp Ile Cys Ala Gly Pro Glu Glu Gln
                405                 410                 415
Glu Leu Arg Leu Gln Glu Glu Val Ser Thr Gln Gly Thr Leu Leu Glu
            420                 425                 430
Ser Gln Ala Ala Leu Ala Leu Leu Gly Pro Gln Thr Leu Gln Tyr Ser
        435                 440                 445
Tyr Thr Pro Gln Leu Gln Asp Leu Asp Pro Leu Thr Arg Glu His Thr
    450                 455                 460
Asp Ser Glu Glu Gly Pro Glu Glu Pro Ser Thr Thr Leu Val Asp
465                 470                 475                 480
Trp Asp Pro Gln Thr Gly Arg Leu Cys Ile Pro Ser Leu Ser Ser Phe
                485                 490                 495
Asp Gln Asp Ser Glu Gly Cys Glu Pro Ser Glu Gly Asp Gly Leu Gly
```

```
              500                 505                 510
Glu Glu Gly Leu Leu Ser Arg Leu Tyr Glu Pro Ala Pro Asp Arg
            515                 520                 525

Pro Pro Gly Glu Asn Glu Thr Tyr Leu Met Gln Phe Met Glu Glu Trp
        530                 535                 540

Gly Leu Tyr Val Gln Met Glu Asn
545                 550

<210> SEQ ID NO 27
<211> LENGTH: 311
<212> TYPE: PRT
<213> ORGANISM: Macaca fascicularis

<400> SEQUENCE: 27

Met Gln Thr Phe Thr Met Val Leu Gln Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Thr Val Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Pro Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Ile Pro Leu Val Leu Ala Leu Phe Ala Phe
225                 230                 235                 240

Val Gly Phe Met Leu Ile Leu Val Val Pro Leu Phe Val Trp Lys
                245                 250                 255

Met Gly Arg Leu Leu Gln Tyr Ser Cys Cys Pro Val Val Leu Pro
            260                 265                 270

Asp Thr Leu Lys Ile Thr Asn Ser Pro Gln Lys Leu Ile Ser Cys Arg
    275                 280                 285

Arg Glu Glu Val Asp Ala Cys Ala Thr Ala Val Met Ser Pro Glu Glu
            290                 295                 300

Leu Leu Arg Ala Trp Ile Ser
305                 310
```

<210> SEQ ID NO 28
<211> LENGTH: 574
<212> TYPE: PRT
<213> ORGANISM: Macaca fascicularis

<400> SEQUENCE: 28

Met Arg Thr Leu Leu Thr Ile Leu Ala Val Gly Ser Leu Ala Ala His
1               5                   10                  15

Ala Pro Glu Asp Pro Ser Asp Leu Leu Gln His Val Lys Phe Gln Ser
            20                  25                  30

Asn Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn His Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Asn Ser Leu Gln His Thr Ala Leu Lys Pro Pro Asp Val Thr Cys
        115                 120                 125

Ile Pro Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Glu Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ser Lys Lys Ser Ala Pro Tyr Met Cys Arg Val Arg Thr Leu Pro Asp
    210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Ala Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Pro Pro Gln Arg His Ser
305                 310                 315                 320

Leu Ser Glu Ile Thr Tyr Leu Gly Gln Pro Asp Ile Ser Ile Leu Gln
                325                 330                 335

Pro Ala Asn Val Pro Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
        355                 360                 365

Thr Pro Glu Ala Gln Leu Pro Phe Tyr Thr Pro Gln Ala Val Ser Lys
    370                 375                 380

Val Gln Pro Pro Ser Tyr Ala Pro Gln Ala Thr Pro Asp Ser Trp Pro

```
                385                 390                 395                 400
Pro Ser Tyr Gly Val Cys Val Glu Gly Ser Gly Lys Asp Ser Pro Thr
                    405                 410                 415
Val Thr Leu Ser Ser Pro Lys His Leu Arg Pro Lys Gly Gln Leu Gln
                420                 425                 430
Lys Glu Pro Pro Ala Gly Ser Cys Met Ser Gly Leu Ser Leu Gln
        435                 440                 445
Glu Val Thr Ser Leu Ala Met Glu Glu Ser Gln Glu Ala Lys Ser Leu
    450                 455                 460
His Gln Pro Leu Gly Val Cys Thr Asp Arg Thr Ser Asp Leu Asn Val
465                 470                 475                 480
Leu Asp Ser Gly Glu Glu Gly Thr Pro Gln Tyr Leu Lys Gly Gln Leu
                485                 490                 495
Pro Leu Leu Ser Ser Val Gln Ile Glu Gly His Pro Met Ser Leu Pro
                500                 505                 510
Leu His Pro Pro Ser Arg Pro Cys Ser Pro Ser Asp Gln Gly Pro Ser
            515                 520                 525
Pro Trp Gly Leu Leu Glu Ser Leu Val Cys Pro Lys Asp Glu Ala Lys
        530                 535                 540
Ser Leu Ala Pro Glu Thr Ser Asp Leu Glu Gln Pro Thr Glu Leu Asp
545                 550                 555                 560
Ser Leu Phe Arg Gly Leu Ala Leu Thr Val Gln Trp Glu Ser
                565                 570
```

```
<210> SEQ ID NO 29
<211> LENGTH: 30
<212> TYPE: DNA
<213> ORGANISM: Homo sapiens

<400> SEQUENCE: 29
agaattccac catgaggacg ctgctgacca                                          30

<210> SEQ ID NO 30
<211> LENGTH: 26
<212> TYPE: DNA
<213> ORGANISM: Homo sapiens

<400> SEQUENCE: 30
gctcgagaca gggaggaagc accaag                                              26

<210> SEQ ID NO 31
<211> LENGTH: 25
<212> TYPE: DNA
<213> ORGANISM: Homo sapiens

<400> SEQUENCE: 31
cgaattccct tggtttctgg ggaag                                               25

<210> SEQ ID NO 32
<211> LENGTH: 27
<212> TYPE: DNA
<213> ORGANISM: Homo sapiens

<400> SEQUENCE: 32
gctcgagcac aggaaacaaa aggcaaa                                             27

<210> SEQ ID NO 33
<211> LENGTH: 33
<212> TYPE: DNA
<213> ORGANISM: Homo sapiens
```

```
<400> SEQUENCE: 33
agaattctgg aaagaaacaa tgttctaggt caa                                    33

<210> SEQ ID NO 34
<211> LENGTH: 25
<212> TYPE: DNA
<213> ORGANISM: Homo sapiens

<400> SEQUENCE: 34
gctcgagctt cacctgggcc cttcc                                             25

<210> SEQ ID NO 35
<211> LENGTH: 35
<212> TYPE: DNA
<213> ORGANISM: Mus musculus

<400> SEQUENCE: 35
ccgaattcgc caccatgaag acactactga ccatc                                  35

<210> SEQ ID NO 36
<211> LENGTH: 33
<212> TYPE: DNA
<213> ORGANISM: Mus musculus

<400> SEQUENCE: 36
cttgcggccg ctcaggattc ccactgcaca gtc                                    33

<210> SEQ ID NO 37
<211> LENGTH: 30
<212> TYPE: DNA
<213> ORGANISM: Mus musculus

<400> SEQUENCE: 37
ttgaattcgc caccatgcac actcccggga                                        30

<210> SEQ ID NO 38
<211> LENGTH: 36
<212> TYPE: DNA
<213> ORGANISM: Mus musculus

<400> SEQUENCE: 38
ttgcggccgc ctagctttcc atttgtacat gtaacc                                 36

<210> SEQ ID NO 39
<211> LENGTH: 34
<212> TYPE: DNA
<213> ORGANISM: Mus musculus

<400> SEQUENCE: 39
ttggatccgc caccatgatt tcccagggag tctg                                   34

<210> SEQ ID NO 40
<211> LENGTH: 31
<212> TYPE: DNA
<213> ORGANISM: Mus musculus

<400> SEQUENCE: 40
ttgcggccgc tcaagtctgt gagatccaga c                                      31

<210> SEQ ID NO 41
<211> LENGTH: 30
<212> TYPE: DNA
<213> ORGANISM: Macaca fascicularis
```

```
<400> SEQUENCE: 41
agaattccac catgaggacg ctgctgacca                                    30

<210> SEQ ID NO 42
<211> LENGTH: 26
<212> TYPE: DNA
<213> ORGANISM: Macaca fascicularis

<400> SEQUENCE: 42
gctcgagaca gggaggaagc accaag                                        26

<210> SEQ ID NO 43
<211> LENGTH: 21
<212> TYPE: DNA
<213> ORGANISM: Macaca fascicularis

<400> SEQUENCE: 43
gtgggactga gcagtctgct g                                             21

<210> SEQ ID NO 44
<211> LENGTH: 21
<212> TYPE: DNA
<213> ORGANISM: Macaca fascicularis

<400> SEQUENCE: 44
aggcaaaagg aagtgttggc a                                             21

<210> SEQ ID NO 45
<211> LENGTH: 33
<212> TYPE: DNA
<213> ORGANISM: Macaca fascicularis

<400> SEQUENCE: 45
agaattctgg aaagaaacaa tgttctaggt caa                                33

<210> SEQ ID NO 46
<211> LENGTH: 25
<212> TYPE: DNA
<213> ORGANISM: Macaca fascicularis

<400> SEQUENCE: 46
gctcgagctt cacctgggcc cttcc                                         25
```